(12) United States Patent
Yeung et al.

(10) Patent No.: US 10,150,747 B2
(45) Date of Patent: Dec. 11, 2018

(54) COMPOUNDS FOR THE TREATMENT OF HEPATITIS C

(71) Applicant: BRISTOL-MYERS SQUIBB COMPANY, Princeton, NJ (US)

(72) Inventors: Kap-Sun Yeung, Madison, CT (US); John F. Kadow, Wallingford, CT (US); Rajesh Onkardas Bora, Bangalore (IN); Prakash Anjanappa, Bangalore (IN); Samayamunthula Venkata Satya Arun Kumar Gupta, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/551,017

(22) PCT Filed: Feb. 19, 2016

(86) PCT No.: PCT/US2016/018626
§ 371 (c)(1),
(2) Date: Aug. 14, 2017

(87) PCT Pub. No.: WO2016/137832
PCT Pub. Date: Sep. 1, 2016

(65) Prior Publication Data
US 2018/0022723 A1    Jan. 25, 2018

Related U.S. Application Data

(60) Provisional application No. 62/119,550, filed on Feb. 23, 2015.

(51) Int. Cl.
| | |
|---|---|
| *C07D 405/12* | (2006.01) |
| *C07D 405/14* | (2006.01) |
| *C07D 307/84* | (2006.01) |
| *C07D 413/14* | (2006.01) |
| *C07D 413/12* | (2006.01) |
| *C07D 417/12* | (2006.01) |
| *C07D 471/04* | (2006.01) |
| *C07B 59/00* | (2006.01) |

(52) U.S. Cl.
CPC .......... *C07D 307/84* (2013.01); *C07B 59/002* (2013.01); *C07D 405/12* (2013.01); *C07D 405/14* (2013.01); *C07D 413/12* (2013.01); *C07D 413/14* (2013.01); *C07D 417/12* (2013.01); *C07D 471/04* (2013.01); *C07B 2200/05* (2013.01)

(58) Field of Classification Search
CPC .. C07D 405/14; C07D 413/14; C07D 405/12; C07D 413/12
See application file for complete search history.

(56) References Cited

U.S. PATENT DOCUMENTS

| | | |
|---|---|---|
| 8,048,887 B2 | 11/2011 | Yeung et al. |
| 9,378,653 B2 | 6/2016 | Polonen |
| 9,738,653 B2 * | 8/2017 | Yeung ................ C07D 491/048 |

FOREIGN PATENT DOCUMENTS

WO  WO 2014/159559   * 10/2014

* cited by examiner

*Primary Examiner* — Deepak R Rao
(74) *Attorney, Agent, or Firm* — James Epperson

(57) ABSTRACT

The disclosure provides compounds of formula I, including their salts, as well as compositions and methods of using the compounds. The compounds have activity against hepatitis C virus (HCV) and may be useful in treating those infected with HCV.

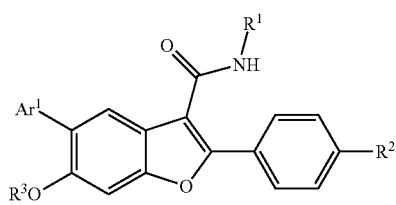

1 Claim, No Drawings

COMPOUNDS FOR THE TREATMENT OF HEPATITIS C

CROSS-REFERENCE TO RELATED APPLICATIONS

This application claims priority to Provisional Patent Application U.S. Ser. No. 62/119,550 filed Feb. 23, 2015, hereby incorporated by reference in its entirety.

BACKGROUND OF THE INVENTION

The disclosure generally relates to the novel compounds of formula I, including their salts, which have activity against hepatitis C virus (HCV) and are useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, showed an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during exteneded dosing of the combination regimens.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I

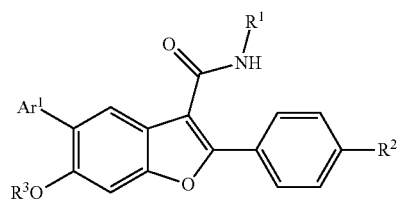

where:
$R^1$ is alkyl;
$R^2$ is halo;
$R^3$ is alkyl, haloalkyl, hydroxyalkyl, or alkoxyalkyl;
$R^4$ is

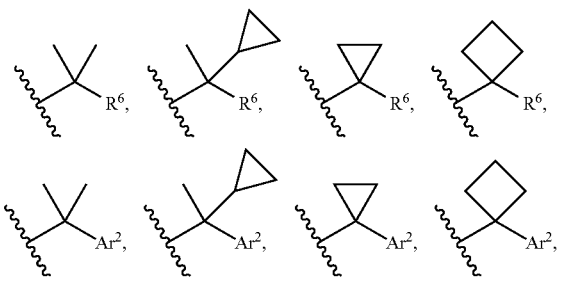

or [1.1.1]bicyclopentanyl;
R$^5$ is hydrogen;
R$^6$ is alkyl or cyano;
Ar$^1$ is phenyl or pyridinyl substituted with 1 CON(R$^4$)(R$^5$) and also with 0-3 substituents selected from cyano, halo, alkyl, haloalkyl, alkoxy, and haloalkoxy; and
Ar$^2$ is phenyl, pyridinyl, pyrimidinyl, pyridazinyl, pyrazinyl, pyrrolyl, furanyl, thienyl, pyrazolyl, oxazolyl, thiazolyl, triazolyl, oxadiazolyl, thiadiazolyl, or imidazopyridinyl;
or a pharmaceutically acceptable salt thereof.

Another aspect of the invention is a compound of formula I where
R$^1$ is methyl;
R$^2$ is fluoro;
R$^3$ is alkyl, haloalkyl, hydroxyalkyl, or alkoxyalkyl;
R$^4$ is

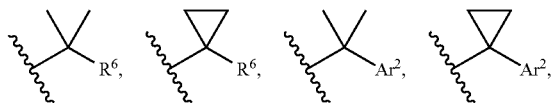

or [1.1.1]bicyclopentanyl;
R$^5$ is hydrogen;
R$^6$ is cyano;
Ar$^1$ is phenyl or pyridinyl substituted with 1 CON(R$^4$)(R$^5$) and also with 0-3 substituents selected from cyano, halo, alkyl, haloalkyl, alkoxy, and haloalkoxy; and
Ar$^2$ is pyrimidinyl, oxadiazolyl, thiadiazolyl, or imidazopyridinyl;
or a pharmaceutically acceptable salt thereof.

Another aspect of the invention is a compound of formula I where alkyl or alkoxy is deuterated.

Another aspect of the invention is a compound of formula I where R$^1$ is methyl.

Another aspect of the invention is a compound of formula I where R$^2$ is fluoro Another aspect of the invention is a compound of formula I where R$^3$ is alkyl or haloalkyl.

Another aspect of the invention is a compound of formula I where R$^3$ is deuterated alkyl or deuterated alkoxy.

Another aspect of the invention is a compound of formula I where R$^6$ is cyano.

Another aspect of the invention is a compound of formula I where R$^4$ is

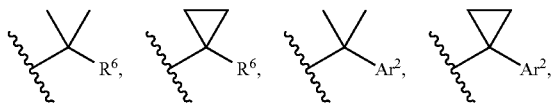

or [1.1.1]bicyclopentanyl and R$^6$ is cyano.

Another aspect of the invention is a compound of formula I where Ar$^1$ is phenyl or pyridinyl substituted with 1 CON(R$^4$)(R$^5$) and also with 0-3 substituents selected from cyano, halo, alkyl, haloalkyl, alkoxy, and haloalkoxy.

Another aspect of the invention is a compound of formula I where Ar$^1$ is phenyl or pyridinyl substituted with 1 CON(R$^4$)(R$^5$) and also with 0-3 substituents selected from cyano, halo, deuterated alkyl, and deuterated alkoxy.

Another aspect of the invention is a compound of formula I where Ar$^1$ is phenyl or pyridinyl substituted with 1 CON(R$^4$)(R$^5$) and with 1 deuterated alkoxy substituent.

Another aspect of the invention is a compound of formula I where Ar$^2$ is pyrimidinyl, oxadiazolyl, thiadiazolyl, or imidazopyridinyl.

Any scope of any variable, including R$^1$, R$^2$, R$^3$, R$^4$, R$^5$, R$^6$, Ar$^1$ and Ar$^2$, can be used independently with the scope of any other instance of a variable.

Unless specified otherwise, these terms have the following meanings. "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes all halogenated isomers from monohalo substituted to perhalo substituted in substituents defined with halo, for example, "Haloalkyl" and "haloalkoxy", "halophenyl", "halophenoxy." Ethylene means ethanediyl or —CH$_2$CH$_2$—; propylene means propanediyl or —CH$_2$CH$_2$CH$_2$—; butylene means butanediyl or —CH$_2$CH$_2$CH$_2$CH$_2$—; pentylene means pentanediyl or —CH$_2$CH$_2$CH$_2$CH$_2$CH$_2$—. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucuronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms. The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon or a ribavirin. Another aspect of the invention is where the interferon is selected from interferon alpha 2B, pegylated interferon alpha, consensus interferon, interferon alpha 2A, interferon lambda, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon or a ribavirin.

Another aspect of the invention is the method where the interferon is selected from interferon alpha 2B, pegylated interferon alpha, consensus interferon, interferon alpha 2A, interferon lambda, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, lozenges, and powders as well as liquid suspensions, syrups, elixirs, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regimen, however, will be determined by a physician using sound medical judgment.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regimen, however, will be determined by a physician using sound medical judgment.

Some examples of compounds suitable for compositions and methods are listed in Table 1.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/ Viropharma |
| NM-283 | Antiviral | NS5B Replicase Inhibitor | Idenix/Novartis |
| GL-59728 | Antiviral | NS5B Replicase Inhibitor | Gene Labs/ Novartis |
| GL-60667 | Antiviral | NS5B Replicase Inhibitor | Gene Labs/ Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |

TABLE 1-continued

| Brand Name | Physiological Class | Type of Inhibitor or Target | Source Company |
|---|---|---|---|
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |

TABLE 1-continued

| Brand Name | Physiological Class | Type of Inhibitor or Target | Source Company |
|---|---|---|---|
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Gilead (formerly from Pharmasset) |
| PSI-7977 sofosbuvir | Antiviral | Nucleotide NS5B Polymerase Inhibitor | Gilead (formerly from Pharmasset) |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/Bristol-Myers Squibb |
| asunaprevir | Antiviral | serine protease inhibitor | Bristol-Myers Squibb |
| BMS-791325 | Antiviral | NS5B Polymerase Inhibitor | Bristol-Myers Squibb |
| daclatasvir | Antiviral | HCV NS5A replication complex inhibitor | Bristol-Myers Squibb |
| GS-5885 | Antiviral | HCV NS5A replication complex inhibitor | Gilead |

Synthetic Methods

The compounds may be made by methods known in the art including those described below. Some reagents and intermediates are known in the art. Other reagents and intermediates can be made by methods known in the art using commercially available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "DMSO" for dimethylsulfoxide; "hr" for hours; "rt" or "RT" for room temperature, and "Rt" for retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine; TEA for triethylamine; DCM for dichloromethane Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "hr" for hour or hours, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Scheme 1.

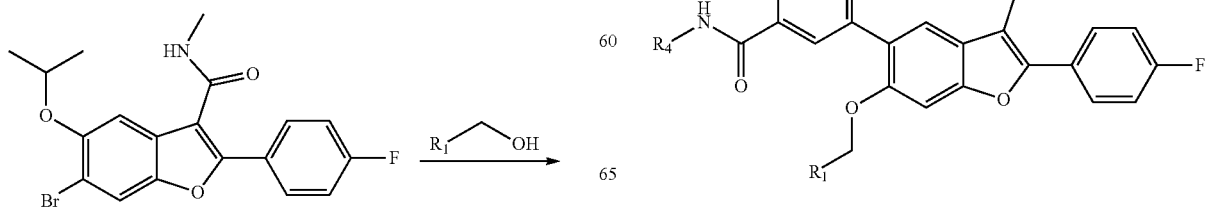

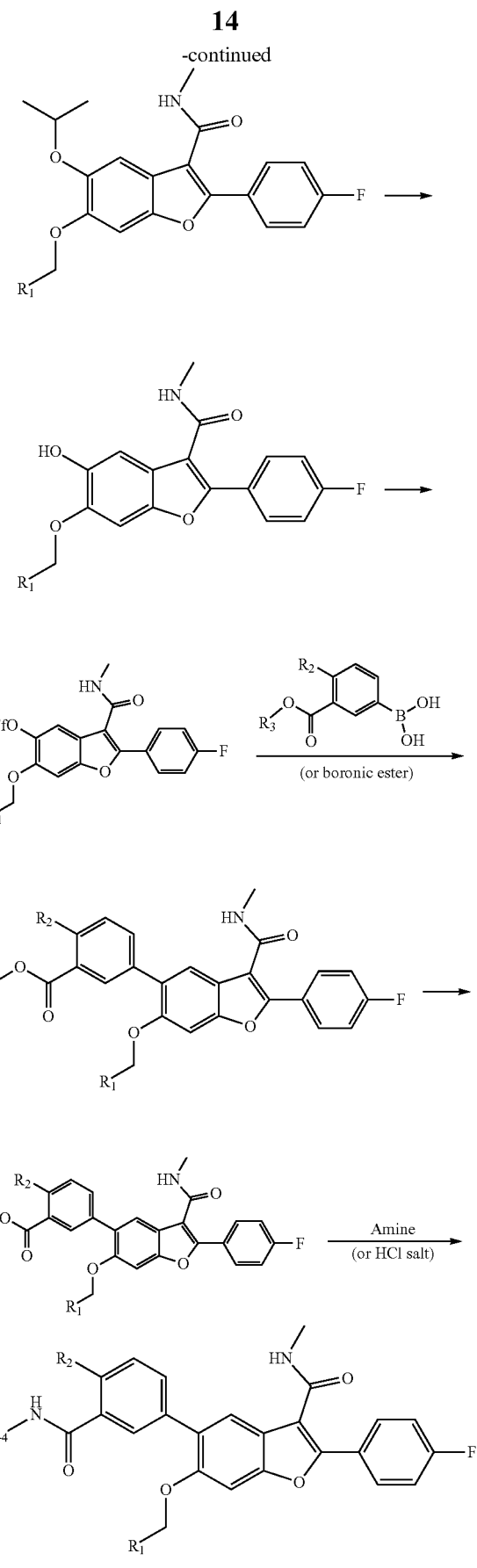

Scheme 2.
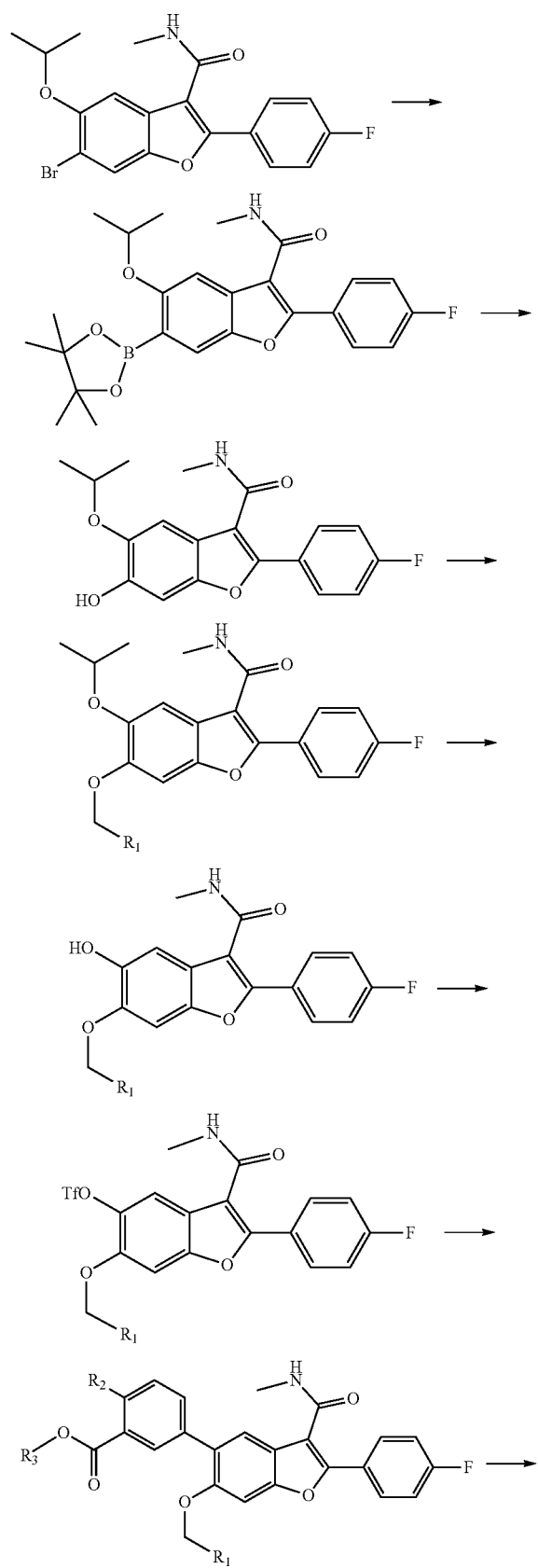
Scheme 3.
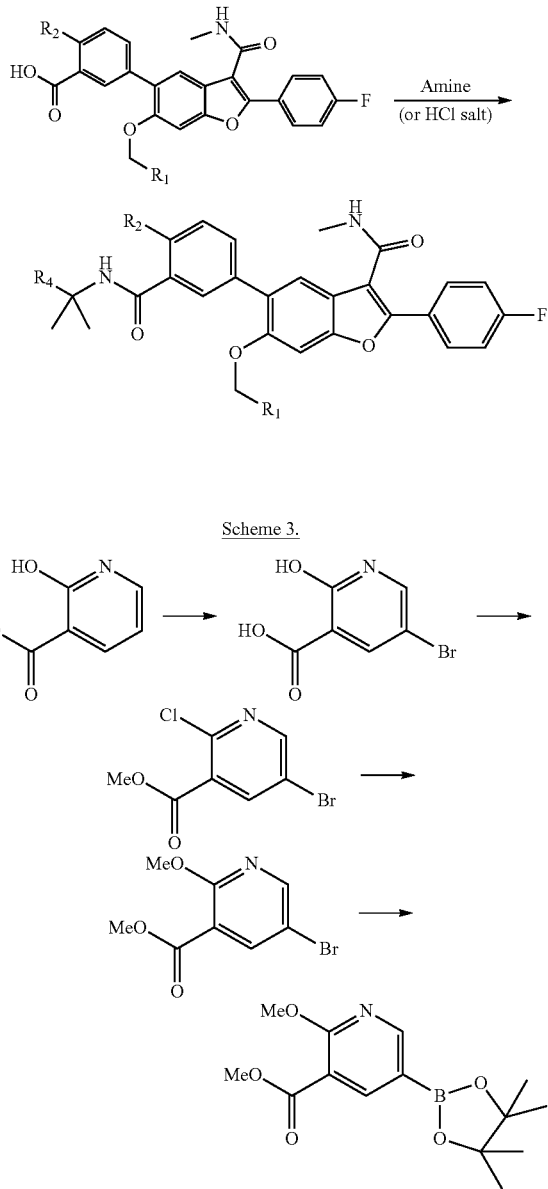
Scheme 4.
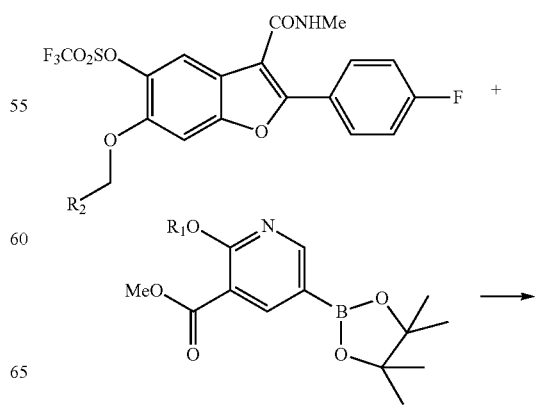

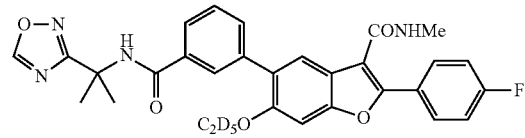
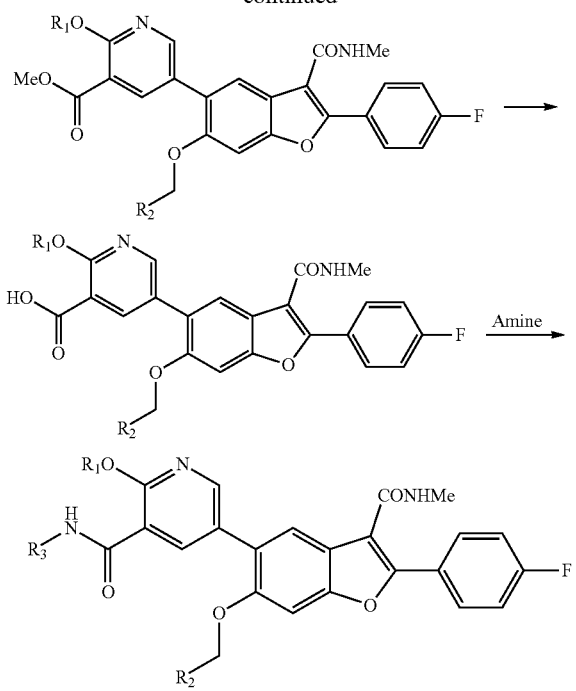
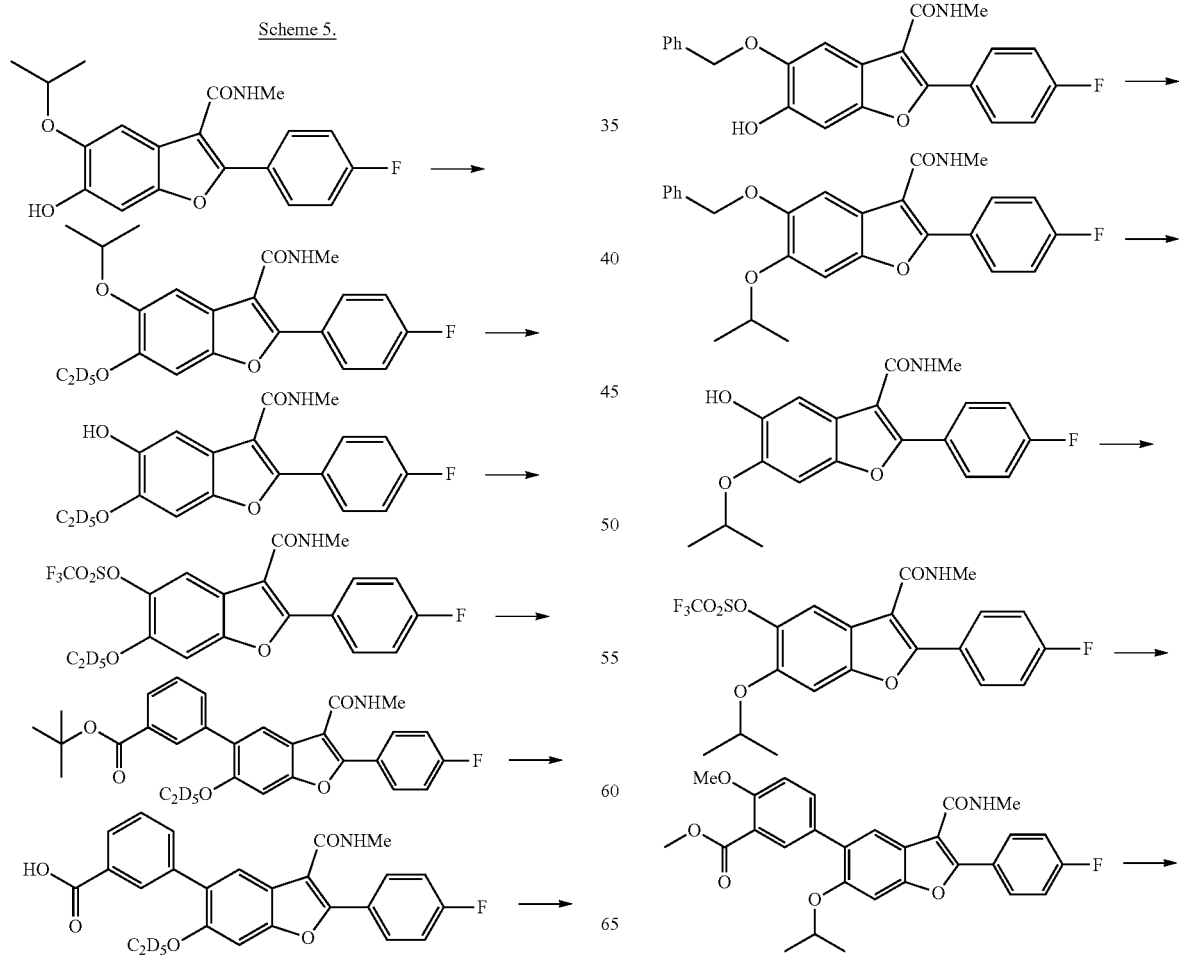

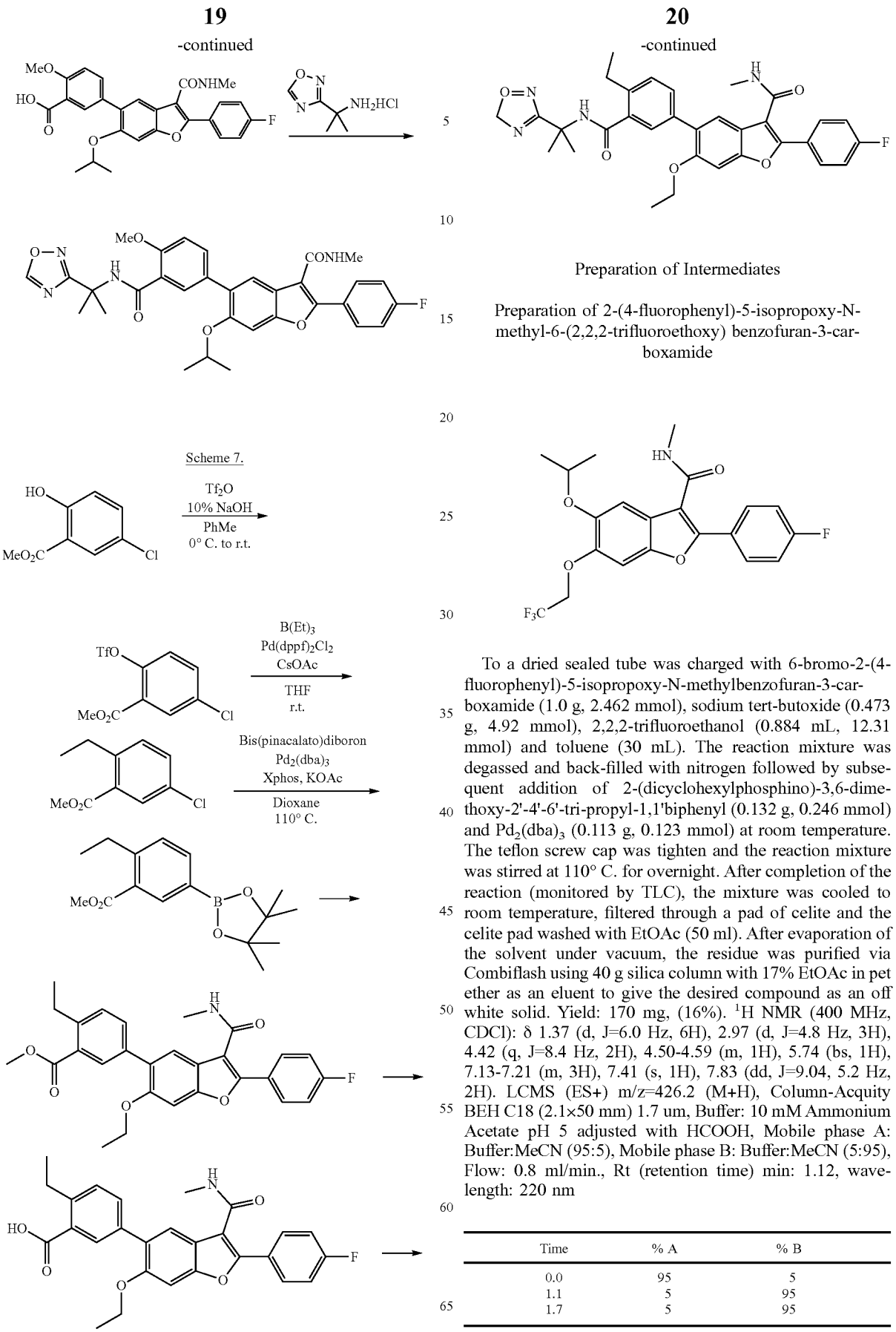

Preparation of Intermediates

Preparation of 2-(4-fluorophenyl)-5-isopropoxy-N-methyl-6-(2,2,2-trifluoroethoxy) benzofuran-3-carboxamide To a dried sealed tube was charged with 6-bromo-2-(4-fluorophenyl)-5-isopropoxy-N-methylbenzofuran-3-carboxamide (1.0 g, 2.462 mmol), sodium tert-butoxide (0.473 g, 4.92 mmol), 2,2,2-trifluoroethanol (0.884 mL, 12.31 mmol) and toluene (30 mL). The reaction mixture was degassed and back-filled with nitrogen followed by subsequent addition of 2-(dicyclohexylphosphino)-3,6-dimethoxy-2'-4'-6'-tri-propyl-1,1'biphenyl (0.132 g, 0.246 mmol) and Pd$_2$(dba)$_3$ (0.113 g, 0.123 mmol) at room temperature. The teflon screw cap was tighten and the reaction mixture was stirred at 110° C. for overnight. After completion of the reaction (monitored by TLC), the mixture was cooled to room temperature, filtered through a pad of celite and the celite pad washed with EtOAc (50 ml). After evaporation of the solvent under vacuum, the residue was purified via Combiflash using 40 g silica column with 17% EtOAc in pet ether as an eluent to give the desired compound as an off white solid. Yield: 170 mg, (16%). $^1$H NMR (400 MHz, CDCl): δ 1.37 (d, J=6.0 Hz, 6H), 2.97 (d, J=4.8 Hz, 3H), 4.42 (q, J=8.4 Hz, 2H), 4.50-4.59 (m, 1H), 5.74 (bs, 1H), 7.13-7.21 (m, 3H), 7.41 (s, 1H), 7.83 (dd, J=9.04, 5.2 Hz, 2H). LCMS (ES+) m/z=426.2 (M+H), Column-Acquity BEH C18 (2.1×50 mm) 1.7 um, Buffer: 10 mM Ammonium Acetate pH 5 adjusted with HCOOH, Mobile phase A: Buffer:MeCN (95:5), Mobile phase B: Buffer:MeCN (5:95), Flow: 0.8 ml/min., Rt (retention time) min: 1.12, wavelength: 220 nm

| Time | % A | % B |
|---|---|---|
| 0.0 | 95 | 5 |
| 1.1 | 5 | 95 |
| 1.7 | 5 | 95 |

Preparation of 2-(4-fluorophenyl)-5-hydroxy-N-methyl-6-(2,2,2-trifluoroethoxy)benzofuran-3-carboxamide

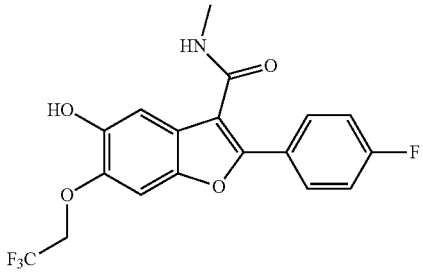 [SMILES: CNC(=O)c1c(-c2ccc(F)cc2)oc2cc(OCC(F)(F)F)c(OS(=O)(=O)C(F)(F)F)cc12]

Trichloroborane (1.0M in toluene) (1.199 mL, 1.199 mmol) was added to a stirred solution of 2-(4-fluorophenyl)-5-isopropoxy-N-methyl-6-(2,2,2-trifluoroethoxy)benzofuran-3-carboxamide (170 mg, 0.400 mmol) in DCM (20 mL) at −78° C. The reaction mixture was allowed to stir at 0° C. for 15 min. After completion (monitored by TLC), the reaction mixture was poured into ice-water, stirred for 10 min and extracted with DCM (50 ml×3). The combined DCM layers were washed with brine solution, dried over anhydrous Na$_2$SO$_4$ and concentrated under reduced pressure. The residue was triturated with pet ether and filtered to obtain the product as an off white solid. Yield: 130 mg, (85%). $^1$H NMR (300 MHz, CDCl$_3$): δ 3.03 (d, J=4.91 Hz, 3H) 4.51 (q, J=7.96 Hz, 2H) 5.61 (s, 1H), 5.83 (bs, 1H), 7.10 (s, 1H), 7.13-7.22 (m, 2H) 7.40 (s, 1H) 7.89-8.00 (m, 2H). LCMS (ES+) m/z=384.1 (M+H), Column-Acquity BEH C18 (2.1×50 mm) 1.7 um, Buffer: 10 mM Ammonium Acetate pH 5 adjusted with HCOOH, Mobile phase A: Buffer:MeCN (95:5), Mobile phase B: Buffer:MeCN (5:95), Flow: 0.8 ml/min., Rt min: 0.95, wavelength: 220 nm.

| Time | % A | % B |
|---|---|---|
| 0.0 | 95 | 5 |
| 1.1 | 5 | 95 |
| 1.7 | 5 | 95 |

Preparation of 2-(4-fluorophenyl)-3-(methylcarbamoyl)-6-(2,2,2-trifluoro-ethoxy)benzofuran-5-yl trifluoromethanesulfonate

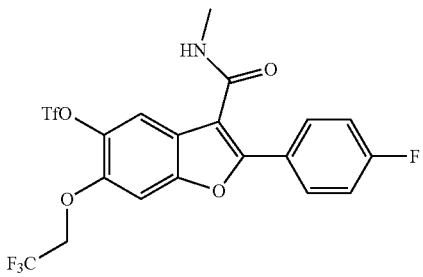

To a stirred solution of 2-(4-fluorophenyl)-5-hydroxy-N-methyl-6-(2,2,2-trifluoroethoxy)benzofuran-3-carboxamide (120 mg, 0.313 mmol) in DMF (7.5 mL) was added DMAP (38.2 mg, 0.313 mmol) followed by 1,1,1-trifluoro-N-phenyl-N-((trifluoromethyl)sulfonyl)methanesulfonamide (134 mg, 0.376 mmol). After being stirred at room temperature for overnight, the resulting reaction mixture was poured into water and extracted with EtOAc (50 ml×3). The combined organic layers were washed with saturated brine solution, dried over anhydrous Na$_2$SO$_4$ and concentrated in reduced pressure. The crude product was purified via Combiflash using a 12 g silica column with 26% EtOAc in pet ether as an eluent to afford the desired compound as an white solid. Yield: 135 mg, 84%. $^1$H NMR (300 MHz, CDCl$_3$): δ 3.01 (d, J=4.9 Hz, 3H), 4.51 (q, J=7.8 Hz, 2H), 5.77 (bs, 1H), 7.20-7.28 (m, 3H), 7.82-7.92 (m, 3H). LCMS (ES+) m/z=516.2 (M+H), Column-Acquity BEH C18 (2.1×50 mm) 1.7 um, Buffer: 10 mM Ammonium Acetate pH 5 adjusted with HCOOH, Mobile phase A: Buffer:MeCN (95:5), Mobile phase B: Buffer:MeCN (5:95), Flow: 0.8 ml/min., Rt min: 1.14, wavelength: 220 nm.

| Time | % A | % B |
|---|---|---|
| 0.0 | 95 | 5 |
| 1.1 | 5 | 95 |
| 1.7 | 5 | 95 |

Preparation of tert-butyl 3-(2-(4-fluorophenyl)-3-(methylcarbamoyl)-6-(2,2,2-trifluoroethoxy)benzofuran-5-yl)benzoate

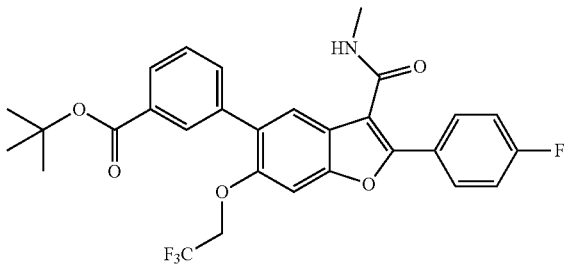 [SMILES: CNC(=O)c1c(-c2ccc(F)cc2)oc2cc(OCC(F)(F)F)c(-c3cccc(C(=O)OC(C)(C)C)c3)cc12]

2-(4-Fluorophenyl)-3-(methylcarbamoyl)-6-(2,2,2-trifluoroethoxy)benzofuran-5-yl trifluoro-methanesulfonate (100 mg, 0.194 mmol), (3-(tert-butoxycarbonyl)phenyl)boronic acid (47.4 mg, 0.213 mmol), Cs$_2$CO$_3$ (126 mg, 0.388 mmol), dioxane (10 mL) and water (1.0 mL) were added into a sealed tube. The reaction mixture was degassed and back-filled with N$_2$ followed by addition of tetrakis(triphenylphosphine)palladium(0) (22.42 mg, 0.019 mmol) at room temperature. The teflon screw cap of the tube was tighten, and the reaction mixture heated to 110° C. and stir it for overnight. After completion of the reaction (monitored by TLC), the mixture was cooled to room temperature, filtered through a pad of celite and the celite pad washed with EtOA (50 ml). After evaporation of the solvent under vacuum, the residue was purified via Combiflash using a 40 g silica column with 28% EtOAc in pet ether as an eluent to give the desired compound as an white solid. Yield: 100 mg, (95%). $^1$H NMR (400 MHz, CDCl$_3$): δ 1.61 (s, 9H), 3.01 (d, J=4.9 Hz, 3H), 4.31 (q, J=8.0 Hz, 2H), 5.83 (br. s., 1H), 7.14-7.21 (m, 3H), 7.48 (t, J=7.7 Hz, 1H), 7.63-7.71 (m, 1H), 7.78 (s, 1H) 7.89-7.96 (m, 2H), 7.98-8.04 (m, 1H), 8.14 (t, J=1.5 Hz, 1H). LCMS (ES+) m/z=544.3 (M+H), Column-Acquity BEH C18 (2.1×50 mm) 1.7 um, Buffer: 10 mM Ammonium Acetate pH 5 adjusted with HCOOH, Mobile phase A: Buffer:MeCN (95:5), Mobile phase B: Buffer: MeCN (5:95), Flow: 0.8 ml/min, Rt min: 1.24, wavelength: 220 nm.

| Time | % A | % B |
| --- | --- | --- |
| 0.0 | 95 | 5 |
| 1.1 | 5 | 95 |
| 1.7 | 5 | 95 |

Preparation of 3-(2-(4-fluorophenyl)-3-(methylcarbamoyl)-6-(2,2,2-trifluoroethoxy)benzofuran-5-yl) benzoic acid

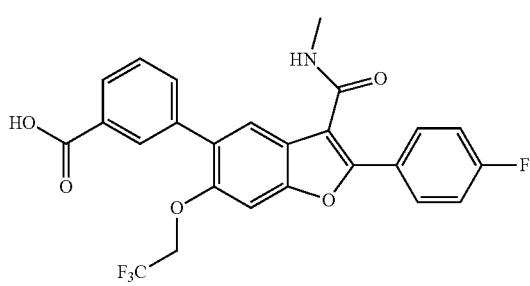 [SMILES: CNC(=O)c1c(-c2ccc(F)cc2)oc2cc(OCC(F)(F)F)c(-c3cccc(C(=O)O)c3)cc12]

To a stirred solution of tert-butyl 3-(2-(4-fluorophenyl)-3-(methylcarbamoyl)-6-(2,2,2-trifluoroethoxy)benzofuran-5-yl)benzoate (80 mg, 0.147 mmol) in DCM (2.5 mL) at 0° C. was added TFA (0.227 mL, 2.94 mmol) slowly. The reaction mixture was allowed to stir at room temperature for 2 hr (=hours). After completion, the reaction mixture was concentrated under reduced pressure. The residue was triturated with pet ether to provide the product as a white solid. Yield: 70 mg, 97%. $^1$H NMR (300 MHz, DMSO-$d_6$): δ 2.83 (d, J=4.6 Hz, 3H), 4.89 (q, J=8.8 Hz, 2H), 7.33-7.44 (m, 2H) 7.54-7.62 (m, 2H), 7.68 (s, 1H), 7.73-7.80 (m, 1H), 7.92-8.02 (m, 3H), 8.12 (t, J=1.5 Hz, 1H), 8.48 (d, J=4.7 Hz, 1H), 13.12 (bs, 1H). LCMS (ES+) m/z=488.3 (M+H), Column-Acquity BEH C18 (2.1×50 mm) 1.7 um, Buffer: 10 mM Ammonium Acetate pH 5 adjusted with HCOOH, Mobile phase A: Buffer:MeCN (95:5), Mobile phase B: Buffer: MeCN (5:95), Flow: 0.8 ml/min, Rt min: 0.82, wavelength: 220 nm.

| Time | % A | % B |
| --- | --- | --- |
| 0.0 | 95 | 5 |
| 1.1 | 5 | 95 |
| 1.7 | 5 | 95 |

Preparation of methyl 5-(2-(4-fluorophenyl)-3-(methylcarbamoyl)-6-(2,2,2-trifluoroethoxy)benzofuran-5-yl)-2-methoxybenzoate

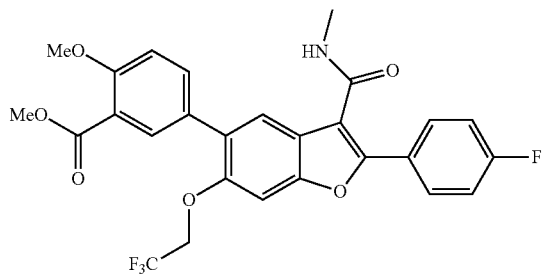 [SMILES: CNC(=O)c1c(-c2ccc(F)cc2)oc2cc(OCC(F)(F)F)c(-c3ccc(OC)c(C(=O)OC)c3)cc12]

To a dried sealed tube was charged with 2-(4-fluorophenyl)-3-(methylcarbamoyl)-6-(2,2,2-trifluoroethoxy)benzofuran-5-yl trifluoromethanesulfonate (100 mg, 0.194 mmol), methyl 2-methoxy-5-(4,4,5,5-tetramethyl-1,3,2-dioxaborolan-2-yl)benzoate (62.4 mg, 0.213 mmol), $K_3PO_4$ (82 mg, 0.388 mmol), dioxane (2.0 mL) and water (0.2 mL) under a $N_2$ atmosphere. The reaction mixture was degassied and back-filled with $N_2$ followed by addition of $PdCl_2$(dppf)-$CH_2Cl_2$ (15.85 mg, 0.019 mmol) at room temperature. The teflon screw cap of the tube was tighten and the reaction mixture heated to stir at 110° C. for overnight. After completion of the reaction (monitored by TLC), the mixture was cooled to room temperature, filtered through a pad of celite and the celite pad washed with EtOAc (50 ml). After evaporation of the solvent under vacuum, the residue was purified via Combiflash using a 24 g silica column with 45% EtOAc in pet ether as an eluent to give the desired compound as a white solid. Yield: 98 mg, (95%). $^1$H NMR (400 MHz, CDCl$_3$): δ 3.01 (d, J=4.9 Hz, 3H), 3.91 (s, 3H), 3.97 (s, 3H), 4.30 (q, J=8.1 Hz, 2H), 5.83 (bs, 1H), 7.05 (d, J=8.6 Hz, 1H) 7.14 (s, 1H), 7.21 (d, J=8.5 Hz, 2H), 7.67 (dd, J=8.6, 2.4 Hz, 1H), 7.77 (s, 1H), 7.92 (dd, 5.2 Hz, 2H), 8.00 (d, J=2.38 Hz, 1H). $^{19}$F NMR (376.6 MHz, CDCl$_3$): δ: −73.54, −109.71. LCMS (ES+) m/z=532.1 (M+H), Column-Acquity BEH C18 (2.1×50 mm) 1.7 um, Buffer: 10 mM Ammonium Acetate pH 5 adjusted with HCOOH, Mobile phase A: Buffer:MeCN (95:5), Mobile phase B: Buffer:MeCN (5:95), Flow: 0.8 ml/min, Rt min: 1.09, wavelength: 220 nm.

| Time | % A | % B |
| --- | --- | --- |
| 0.0 | 95 | 5 |
| 1.1 | 5 | 95 |
| 1.7 | 5 | 95 |

Preparation of 5-(2-(4-fluorophenyl)-3-(methylcarbamoyl)-6-(2,2,2-trifluoro-ethoxy)benzofuran-5-yl)-2-methoxybenzoic acid

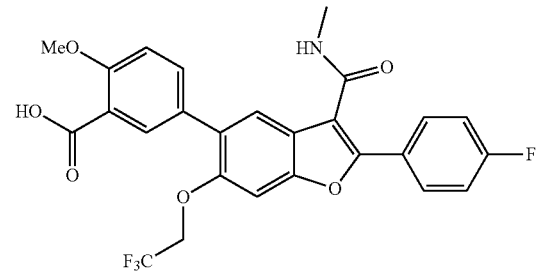 [SMILES: CNC(=O)c1c(-c2ccc(F)cc2)oc2cc(OCC(F)(F)F)c(-c3ccc(OC)c(C(=O)O)c3)cc12]

Sodium hydroxide (1.0M in water) (0.847 mL, 0.847 mmol) was added to a solution of methyl 5-(2-(4-fluorophenyl)-3-(methylcarbamoyl)-6-(2,2,2-trifluoroethoxy)benzofuran-5-yl)-2-methoxybenzoate (90 mg, 0.169 mmol) in MeOH (10 mL) and THF (10 mL) at room temperature. After being stirred at room temperature for overnight, the reaction mixture was concentrated under reduced pressure. The residue was diluted with water, acidified using 1.5N HCl to pH~3 and then stirred for 10 min. The solid was filtered, washed with water and dried under suction to provide the desired compound as a white solid. Yield: 73 mg, (83%). $^1$H NMR (400 MHz, DMSO-d$_6$): δ 2.83 (d, J=4.6 Hz, 3H), 3.87 (s, 3H), 4.87 (q, J=8.8 Hz, 2H) 7.21 (d, J=8.78 Hz, 1H), 7.32-7.44 (m, 2H), 7.53 (s, 1H), 7.57-7.69 (m, 2H), 7.82 (d, J=2.4 Hz, 1H), 7.92-8.02 (m, 2H), 8.45 (d, J=4.6 Hz, 1H), 12.63 (bs, 1H). LCMS (ES+) m/z=518.3 (M+H), Column-Acquity BEH C18 (2.1×50 mm) 1.7 um, Buffer: 10 mM Ammonium Acetate pH 5 adjusted with HCOOH, Mobile phase A: Buffer:MeCN (95:5), Mobile phase B: Buffer:MeCN (5:95), Flow: 0.8 ml/min, Rt min: 0.80, wavelength: 220 nm.

| Time | % A | % B |
|---|---|---|
| 0.0 | 95 | 5 |
| 1.1 | 5 | 95 |
| 1.7 | 5 | 95 |

Preparation of tert-butyl 2-fluoro-5-(2-(4-fluorophenyl)-3-(methylcarbamoyl)-6-(2,2,2-tri-fluoroethoxy)benzofuran-5-yl)benzoate

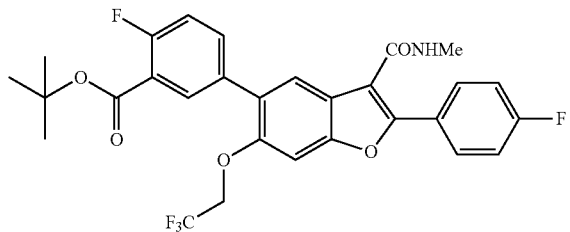

A mixture of 2-(4-fluorophenyl)-3-(methylcarbamoyl)-6-(2,2,2-trifluoroethoxy)benzofuran-5-yl trifluoromethanesulfonate (100 mg, 0.194 mmol), tert-butyl 2-fluoro-5-(4,4,5,5-tetramethyl-1,3,2-dioxaborolan-2-yl)benzoate (68.8 mg, 0.213 mmol) and Cs$_2$CO$_3$ (126 mg, 0.388 mmol) in a mixture of dioxane (10 mL) and water (1 mL) in a sealed tube capped with a rubber septum at ambient temperature was degassed and back filled with N$_2$, followed by addition of tetrakis (triphenylphosphine)palladium(0) (22.42 mg, 0.019 mmol). The sealed tube was tightly closed with a teflon screw cap and the reaction mixture heated to 110° C. and maintained at same temperature for 16 hr. After cooling the reaction mixture to ambient temperature, the mixture was filtered through a celite pad, which was then washed with EtOAc and the filtrate collected concentrated under reduced pressure. The crude product obtained was purified via Combiflash column chromatography using a 24 g silica gel column with 30% EtOAc in petroleum (pet.) ether as an eluent to afford tert-butyl 2-fluoro-5-(2-(4-fluorophenyl)-3-(methylcarbamoyl)-6-(2,2,2-trifluoroethoxy)benzofuran-5-yl)benzoate as an off white solid. Yield: 70 mg, (64.22%). LCMS: (ES+) m/z=562.1 (M+H)$^+$. Column-Acquity BEH C18 (2.1×50 mm) 1.7 um, Mobile phase A: 10 mM AmmoniumAcetate pH-5 adjusted with HCOOH:MeCN (95:5), Mobile phase B: 10 mM AmmoniumAcetate pH-5 adjusted with HCOOH:MeCN (5:95), Flow: 0.8 ml/min. Rt: 1.22 min, wavelength: 220 nm.

| LCMS | | |
|---|---|---|
| Time | % A | % B |
| 0.0 | 95 | 5 |
| 1.1 | 5 | 95 |
| 1.7 | 5 | 95 |

Preparation of 2-fluoro-5-(2-(4-fluorophenyl)-3-(methylcarbamoyl)-6-(2,2,2-trifluoro ethoxy)benzofuran-5-yl)benzoic acid

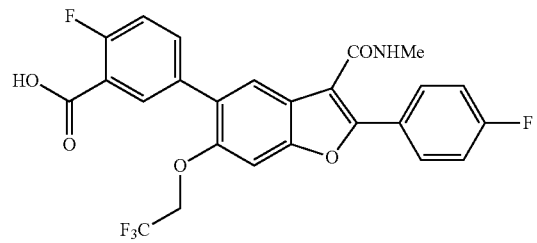

Trifluoroacetic acid (TFA) (0.288 mL, 3.74 mmol) was added slowly to a stirred solution of tert-butyl 2-fluoro-5-(2-(4-fluorophenyl)-3-(methylcarbamoyl)-6-(2,2,2-trifluoroethoxy)benzofuran-5-yl)benzoate (70 mg, 0.125 mmol) in dichloromethane (DCM) (2.5 mL) at 0° C. The reaction mixture was allowed to warm to ambient temperature and stirred for 5 hr. After completion of the reaction, the mixture was concentrated completely under reduced pressure in a rotavapour and the residue triturated with pet. ether to obtained 2-fluoro-5-(2-(4-fluorophenyl)-3-(methylcarbamoyl)-6-(2,2,2-trifluoroethoxy)benzofuran-5-yl)benzoic acid as an off white solid. Yield: 60 mg, (95.23% yield). LCMS: (ES+) m/z=506.2 (M+H)$^+$, Column-Acquity BEH C18 (2.1×50 mm) 1.7 um, Mobile phase A: 10 mM AmmoniumAcetate pH-5 adjusted with HCOOH:MeCN (95:5), Mobile phase B: 10 mM AmmoniumAcetate pH-5 adjusted with HCOOH:MeCN (5:95), Flow: 0.8 ml/min. Rt: 0.80 min, wavelength: 220 nm.

| LCMS | | |
|---|---|---|
| Time | % A | % B |
| 0.0 | 95 | 5 |
| 1.1 | 5 | 95 |
| 1.7 | 5 | 95 |

Preparation of 5-bromo-2-hydroxynicotinic acid

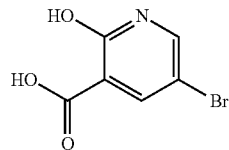 [SMILES: O=C(O)c1cc(Br)cnc1O]

To a stirred ice-cooled solution of 2-hydroxynicotinic acid (10 g, 71.9 mmol) in DMF (100 mL) was added bromine (5.56 mL, 108 mmol) in DMF (20 mL) slowly for 1 hr. The reaction mixture was allowed to stir at room temperature for 3 hr. After completion of the reaction, the reaction mixture was slowly added to ice water (1.5 L), and the mixture stirred for 15 min. The obtained solid was filtered, washed with water and dried under suction to obtain 5-bromo-2-hydroxynicotinic acid as a white solid. Yield: 10.5 g, (67.17%). $^1$H NMR (300 MHz, DMSO-$d_6$) δ=13.68 (bs, 1H), 8.35 (d, J=2.7 Hz, 1H), 8.26 (d, J=2.7 Hz, 1H). LCMS: (ES+) m/z observed=218.2 (M+H)$^+$, Column-Acquity BEH C18 (2.1×50 mm) 1.7 um, Buffer: 10 mM AmmoniumAcetate pH-5 adjusted with HCOOH, Mobile phase A: Buffer:MeCN (95:5), Mobile phase B: Buffer:MeCN (5:95), Flow: 0.8 ml/min. Rt: 0.36 min, wavelength: 220 nm.

| LCMS | | |
|---|---|---|
| Time | % A | % B |
| 0.0 | 95 | 5 |
| 1.1 | 5 | 95 |
| 1.7 | 5 | 95 |

Preparation of methyl 5-bromo-2-chloronicotinate

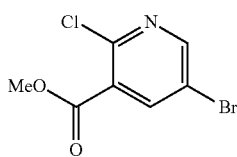

POCl$_3$ (50 mL) was added slowly through an addition funnel to ice-cooled 5-bromo-2-hydroxynicotinic acid (10 g, 45.9 mmol). The reaction mixture was heated to 95° C. and stirred at the same temperature for 16 hr. After cooling to room temperature, the reaction mixture was concentrated under reduced pressure to remove POCl$_3$. To the residue was added toluene (100 ml), and the mixture evaporated under reduced pressure to remove residual POCl$_3$. The obtained residue was diluted with DCM (100 mL) and cooled. MeOH (50 mL) was added slowly through an addition funnel to the mixture under nitrogen. The resulting mixture was then stirred at room temperature for 2 hr. After completion of the reaction, the reaction mixture was concentrated under reduced pressure. The residue thus obtained was diluted with water, neutralized by using saturated aq. Na$_2$CO$_3$ solution, and extracted with EtOAc (50 ml×3). The combined organic layers were washed with brine, dried over Na$_2$SO$_4$, filtered and concentrated under reduced pressure. The crude product was purified via Combiflash column chromatography using a 40 g silica gel column with 7% EtOAc in pet. ether as an eluent to afford methyl 5-bromo-2-chloronicotinate as a white solid. Yield: 8.5 g, (74%). $^1$H NMR (400 MHz, CDCl$_3$) δ ppm=8.57 (d, J=2.4 Hz, 1H), 8.29 (d, J=2.4 Hz, 1H), 3.91 (s, 3H). LCMS: (ES+) m/z observed=252.1 (M+H)$^+$, Column-Acquity BEH C18 (2.1×50 mm) 1.7 um, Buffer: 10 mM AmmoniumAcetate pH-5 adjusted with HCOOH, Mobile phase A: Buffer:MeCN (95:5), Mobile phase B: Buffer:MeCN (5:95), Flow: 0.8 ml/min. Rt: 0.86 min, wavelength: 220 nm.

| LCMS | | |
|---|---|---|
| Time | % A | % B |
| 0.0 | 95 | 5 |
| 1.1 | 5 | 95 |
| 1.7 | 5 | 95 |

Preparation of methyl 5-bromo-2-methoxynicotinate

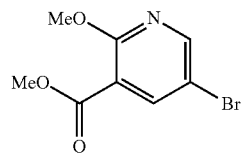

To a stirred solution of methyl 5-bromo-2-chloronicotinate (4.0 g, 15.97 mmol) in MeOH (50 mL) at ambient temperature under a nitrogen atmosphere was slowly added sodium methoxide (30% in MeOH) (28.8 g, 160 mmol). After addition, the reaction mixture was stirred at room temperature for 3 hr. After completion of the reaction (monitored by TLC), the reaction mixture was diluted with water and the product extracted with EtOAc (75 ml×3). The combined organic layers were washed with saturated brine solution, dried over Na$_2$SO$_4$ and concentrated under reduced pressure to obtained pure methyl 5-bromo-2-methoxynicotinate as a white solid. Yield: 2.2 g, (56%). $^1$H NMR (400 MHz, CDCl$_3$) δ ppm=8.34 (d, J=2.8 Hz, 1H), 8.24 (d, J=2.4 Hz, 1H), 4.02 (s, 3H), 3.90 (s, 3H). LCMS: (ES+) m/z observed=248.2 (M+H)$^+$, Column-Acquity BEH C18 (2.1×50 mm) 1.7 um, Buffer: 10 mM AmmoniumAcetate pH-5 adjusted with HCOOH, Mobile phase A: Buffer: MeCN (95:5), Mobile phase B: Buffer:MeCN (5:95), Flow: 0.8 ml/min. Rt: 0.85 min, wavelength: 220 nm.

| LCMS | | |
|---|---|---|
| Time | % A | % B |
| 0.0 | 95 | 5 |
| 1.1 | 5 | 95 |
| 1.7 | 5 | 95 |

Preparation of methyl 2-methoxy-5-(4,4,5,5-tetramethyl-1,3,2-dioxaborolan-2-yl)nicotinate

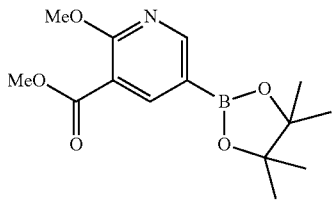 [SMILES: COC(=O)c1cc(B2OC(C)(C)C(C)(C)O2)cnc1OC]

A mixture of methyl 5-bromo-2-methoxynicotinate (1.9 g, 7.72 mmol), 4,4,4',4',5,5,5',5'-octamethyl-2,2'-bi(1,3,2-dioxaborolane) (2.353 g, 9.27 mmol), potassium acetate (1.516 g, 15.44 mmol) in 1,4-dioxane (100 mL) in a sealed tube capped with rubber septum at ambient temperature under a nitrogen atmosphere was degassed and back filled with nitrogen, and then $PdCl_2(dppf)\cdot CH_2Cl_2$ adduct (0.631 g, 0.772 mmol) was added to the mixture. The reaction mixture was heated to 100° C. and stirred at the same temperature for 3 hr. After cooling to room temperature, the completion of the reaction was confirmed by TLC. The reaction mixture was filtered through a celite pad, which was washed with EtOAc. The filtrate was concentrated under reduced pressure. The crude product was purified via Combiflash column chromatography using a 40 g silica gel column with 20% EtOAc in pet. ether as an eluent to afford methyl 2-methoxy-5-(4,4,5,5-tetramethyl-1,3,2-dioxaborolan-2-yl)nicotinate as a white solid. Yield: 1.5 g, (66.37%). $^1$H NMR (400 MHz, $CDCl_3$) δ=8.65 (d, J=2.0 Hz, 1H), 8.49 (d, J=2.0 Hz, 1H), 4.07 (s, 3H), 3.89 (s, 3H), 1.34 (s, 12H). LCMS: (ES+) m/z=294.3 $(M+H)^+$, Column-Acquity BEH C18 (2.1×50 mm) 1.7 um, Buffer: 10 mM AmmoniumAcetate pH-5 adjusted with HCOOH, Mobile phase A: Buffer:MeCN (95:5), Mobile phase B: Buffer:MeCN (5:95), Flow: 0.8 ml/min. Rt: 1.07 min, wavelength: 220 nm.

| LCMS | | |
| --- | --- | --- |
| Time | % A | % B |
| 0.0 | 95 | 5 |
| 1.1 | 5 | 95 |
| 1.7 | 5 | 95 |

Preparation of methyl 5-(6-ethoxy-2-(4-fluorophenyl)-3-(methylcarbamoyl)benzofuran-5-yl)-2-methoxynicotinate

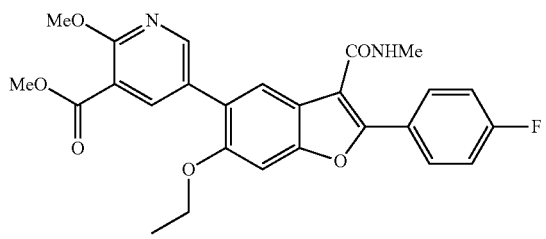

A mixture of 6-ethoxy-2-(4-fluorophenyl)-3-(methylcarbamoyl)benzofuran-5-yl trifluoromethanesulfonate (300 mg, 0.650 mmol), methyl 2-methoxy-5-(4,4,5,5-tetramethyl-1,3,2-dioxaborolan-2-yl)nicotinate (210 mg, 0.715 mmol) and $Cs_2CO_3$ (424 mg, 1.300 mmol) in a mixture of dioxane (20 mL)/water (2.0 mL) in a sealed tube capped with a rubber septum at room temperature was degassed and back filled with nitrogen, and then tetrakis(triphenylphosphine)palladium(0) (75 mg, 0.065 mmol) was added to the mixture. The reaction mixture was stirred at 110° C. for 18 hr. After cooling to room temperature, the completion of the reaction was confirmed by TLC. The reaction mixture was filtered through a celite pad, which was then washed with EtOAc. The filtrate was concentrated under reduced pressure. The crude product obtained was purified via Combiflash using a 24 g silica gel column with 46% EtOAc in pet. ether as an eluent to afford methyl 5-(6-ethoxy-2-(4-fluorophenyl)-3-(methylcarbamoyl)benzofuran-5-yl)-2-methoxynicotinate as a white solid. Yield: 240 mg, (77.17%). LCMS: (ES+) m/z=479.3 $(M+H)^+$, Column-Acquity BEH C18 (2.1×50 mm) 1.7 um, Buffer: 10 mM Ammonium Acetate pH-5 adjusted with HCOOH, Mobile phase A: Buffer:MeCN (95:5), Mobile phase B: Buffer:MeCN (5:95), Flow: 0.8 ml/min. Rt: 1.15 min, wavelength: 220 nm.

| LCMS | | |
| --- | --- | --- |
| Time | % A | % B |
| 0.0 | 95 | 5 |
| 1.1 | 5 | 95 |
| 1.7 | 5 | 95 |

Preparation of 5-(6-ethoxy-2-(4-fluorophenyl)-3-(methylcarbamoyl)benzofuran-5-yl)-2-methoxynicotinic acid

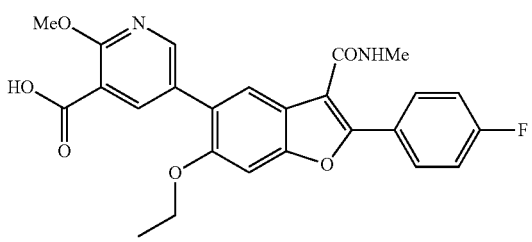

A sodium hydroxide solution (1.0 M in water) (2.508 mL, 2.508 mmol) was added to a stirred solution of methyl 5-(6-ethoxy-2-(4-fluorophenyl)-3-(methylcarbamoyl)benzofuran-5-yl)-2-methoxynicotinate (240 mg, 0.502 mmol) in MeOH (15 mL)/THF (15 mL) at room temperature and the reaction mixture was then stirred at room temperature for 18 hr. After completion of the reaction (monitored by TLC), the reaction mixture was concentrated under reduced pressure. The residue was diluted with water, acidified by using 1.5 N HCl to pH~3 under ice-cold condition. The mixture was stirred for 5 min and the solid filtered to afford pure 5-(6-ethoxy-2-(4-fluorophenyl)-3-(methylcarbamoyl)benzofuran-5-yl)-2-methoxynicotinic acid as a white solid. Yield: 190 mg, (82.32%). LCMS: (ES+) m/z=465.2 $(M+H)^+$, Column-Ascentis Express C18 (50×2.1 mm-2.7 μm), Mobile phase A: 2% MeCN-98% $H_2O$-10 mM NH$_4$COOH, Mobile phase B: 98% MeCN-2% H$_2$O-10 mM NH$_4$COOH, Flow: 1.0 ml/Min, Rt: 1.78 min, wavelength: 220 nm.

| LCMS | | |
|---|---|---|
| Time | % A | % B |
| 0.0 | 100 | 0 |
| 1.7 | 0 | 100 |
| 3.4 | 0 | 100 |

Preparation of 6-(ethoxy-1,1,2,2,2-d$_5$)-2-(4-fluorophenyl)-5-isopropoxy-N-methylbenzofuran-3-carboxamide

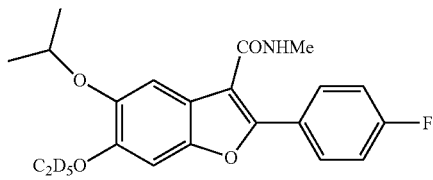

To a stirred solution of 2-(4-fluorophenyl)-6-hydroxy-5-isopropoxy-N-methylbenzofuran-3-carboxamide (200 mg, 0.582 mmol) in acetonitrile (30 mL) at room temperature was added potassium carbonate (161 mg, 1.165 mmol) followed by iodoethane-d$_5$ (141 mg, 0.874 mmol). The reaction mixture was stirred at room temperature for 16 hr. After completion of the reaction (monitored by TLC), the reaction mixture was filtered through a Buchner funnel and the filtrate concentrated under reduced pressure. The crude product was recrystalized from EtOAc and pet. ether to obtained the desired compound as an off white solid. Yield: 175 mg, (79.90%). LCMS: (ES+) m/z=377.4 (M+H)$^+$, Column-ACQUITY UPLC BEH C8 (50×2.1 mm; 1.7 µm), Mobile phase A: 10 mM Ammonium Acetate pH-5 adjusted with HCOOH:MeCN (95:5), Mobile phase B: 10 mM Ammonium Acetate pH-5 adjusted with HCOOH:MeCN (5:95), Flow: 0.8 ml/min, Rt: 1.09 min, wavelength: 220 nm.

| LCMS | | |
|---|---|---|
| Time | % A | % B |
| 0.0 | 95 | 5 |
| 1.1 | 5 | 95 |
| 1.7 | 5 | 95 |

Preparation of 6-(ethoxy-1,1,2,2,2-d$_5$)-2-(4-fluorophenyl)-5-hydroxy-N-methylbenzofuran-3-carboxamide

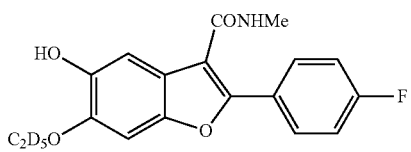

A solution of trichloroborane (1.0M in DCM) (1.594 mL, 1.594 mmol) was added to a solution of 6-(ethoxy-1,1,2,2,2-d$_5$)-2-(4-fluorophenyl)-5-isopropoxy-N-methylbenzofuran-3-carboxamide (150 mg, 0.398 mmol) in DCM (20 mL) at −78° C. The reaction mixture was allowed to stir at 0° C. for 5 min. After completion of the reaction (monitored by TLC), the reaction mixture was concentrated under reduced pressure to remove volatiles. The residue was diluted with ice cooled water, stirred for 5 min, the obtained solid filtered and dried under suction to afford the desired compound as a white solid. Yield: 120 mg, (90.22%). LCMS: (ES+) m/z=335.4 (M+H)$^+$, Column-ACQUITY UPLC BEH C8 (50×2.1 mm; 1.7 µm), Mobile phase A: 10 mM Ammonium Acetate pH-5 adjusted with HCOOH:MeCN (95:5), Mobile phase B: 10 mM Ammonium Acetate pH-5 adjusted with HCOOH:MeCN (5:95), Flow: 0.8 ml/min, Rt: 0.88 min, wavelength: 220 nm.

| LCMS | | |
|---|---|---|
| Time | % A | % B |
| 0.0 | 95 | 5 |
| 1.1 | 5 | 95 |
| 1.7 | 5 | 95 |

Preparation of 6-(ethoxy-1,1,2,2,2-d$_5$)-2-(4-fluorophenyl)-3-(methylcarbamoyl)benzofuran-5-yl trifluoromethanesulfonate

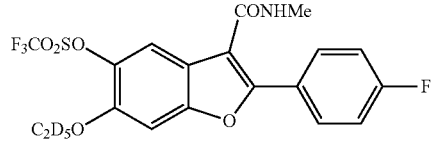

DMAP (36.5 mg, 0.299 mmol) followed by 1,1,1-trifluoro-N-phenyl-N-((trifluoromethyl)sulfonyl)methanesulfonamide (128 mg, 0.359 mmol) were added to a stirred solution of 6-(ethoxy-1,1,2,2,2-d$_5$)-2-(4-fluorophenyl)-5-hydroxy-N-methylbenzofuran-3-carboxamide (100 mg, 0.299 mmol) in DMF (10 mL) at room temperature under a nitrogen atmosphere. The reaction mixture was stirred at room temperature for 16 hr. After completion of the reaction (monitored by TLC), the reaction mixture was diluted with water and the product extracted with EtOAc (25 ml×3). The combined organic layers were washed with saturated brine solution, dried over Na$_2$SO$_4$ and concentrated under reduced pressure. The residue obtained was purified via Combiflash using a 24 g silica gel column with 20% EtOAc in pet. ether as an eluent to afford the desired compound as a white solid. Yield: 80 mg, (57.53%). LCMS: (ES+) m/z=467 (M+H)$^+$, Column-Acentis Express C18 (50×2.1 mm; 2.7 um), Buffer: 10 mM Ammonium Formate in Water, Mobile phase A: Buffer:MeCN (98:2), Mobile phase B: Buffer:MeCN (2:98), Flow: 1.0 ml/min, Rt: 2.43 min, wavelength: 220 nm.

| LCMS | | |
|---|---|---|
| Time | % A | % B |
| 0.0 | 100 | 0 |
| 1.7 | 0 | 100 |

| LCMS | | |
|---|---|---|
| Time | % A | % B |
| 3.0 | 0 | 100 |
| 3.2 | 100 | 0 |

Preparation of tert-Butyl 3-(6-(ethoxy-1,1,2,2,2-d₅)-2-(4-fluorophenyl)-3-(methylcarbamoyl)benzofuran-5-yl)benzoate

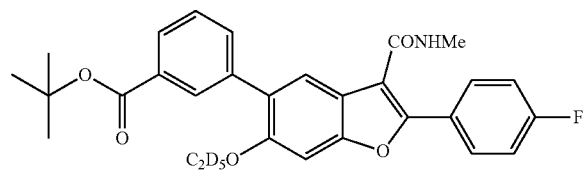

A mixture of 6-(ethoxy-1,1,2,2,2-d₅)-2-(4-fluorophenyl)-3-(methylcarbamoyl)benzofuran-5-yl trifluoromethanesulfonate (70 mg, 0.150 mmol), (3-(tert-butoxycarbonyl)phenyl)boronic acid (40.0 mg, 0.180 mmol) and Cs$_2$CO$_3$ (98 mg, 0.300 mmol) in dioxane (10 mL)/water (1.0 mL) in a sealed tube capped with a rubber septum at room temperature was degassed and back filled with nitrogen, and then tetrakis(triphenylphosphine)palladium(0) (17.34 mg, 0.015 mmol) was added to the mixture. The reaction mixture was heated to 100° C. and stirred at same temperature for 16 hr. After cooling to room temperature, completion of the reaction was confirmed by TLC. The reaction mixture was filtered through a celite pad, which was then washed with EtOAc. The filtrate was concentrated under reduced pressure, and the crude product purified via Combiflash using a 12 g silica gel column with 24% EtOAc in pet. ether as an eluent to afford the desired compound as a white solid. Yield: 65 mg, (87.57%). ¹H NMR (300 MHz, CHLOROFORM-d) δ ppm=8.19 (t, J=1.6 Hz, 1H), 8.01-7.99 (m, 1H), 7.99-7.94 (m, 2H), 7.72-7.70 (m, 2H), 7.48 (t, J=7.7 Hz, 1H), 7.19 (t, J=8.7 Hz, 2H), 7.13 (s, 1H), 5.88 (b s, 1H), 3.03 (d, J=4.9 Hz, 3H), 1.63 (s, 9H). LCMS: (ES+) m/z=495.4 (M+H)⁺, Column-ACQUITY UPLC BEH C8 (50×2.1 mm; 1.7 μm), Moblie phase A: 10 mM Ammonium Acetate pH-5 adjusted with HCOOH:MeCN (95:5), Mobile phase B: 10 mM Ammonium Acetate pH-5 adjusted with HCOOH:MeCN (5:95), Flow: 0.8 ml/min, Rt: 1.31 min, wavelength: 220 nm.

| LCMS | | |
|---|---|---|
| Time | % A | % B |
| 0.0 | 95 | 5 |
| 1.1 | 5 | 95 |
| 1.7 | 5 | 95 |

Preparation of 3-(6-(Ethoxy-1,1,2,2,2-d₅)-2-(4-fluorophenyl)-3-(methylcarbamoyl)benzofuran-5-yl) benzoic acid

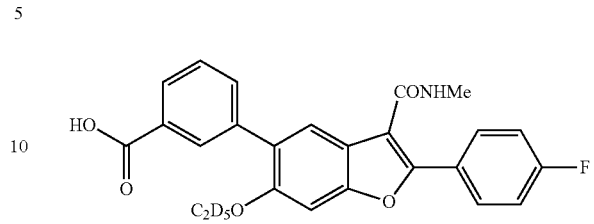

To a stirred solution of tert-butyl 3-(6-(ethoxy-1,1,2,2,2-d₅)-2-(4-fluorophenyl)-3-(methylcarbamoyl)benzofuran-5-yl)benzoate (65 mg, 0.131 mmol) in DCM (2.5 mL) cooled to ice-water temperature was added TFA (0.496 mL, 6.44 mmol) slowly. The reaction mixture was allowed to stir at room temperature for 2 hr. After completion of the reaction (monitored by TLC), the reaction mixture was concentrated completely under reduced pressure. The desired compound obtained as an off white solid was used for the subsequent step. Yield: 50 mg, (86.77%). LCMS: (ES+) m/z=439.2 (M+H)⁺, Column-Acentis Express C18 (50×2.1 mm; 2.7 um), Buffer: 10 mM Ammonium Formate in Water, Mobile phase A: Buffer:MeCN (98:2), Mobile phase B: Buffer:MeCN (2:98), Flow: 1.0 ml/min, Rt: 1.91 min, wavelength: 220 nm.

| Time | % A | % B |
|---|---|---|
| 0.0 | 100 | 0 |
| 1.7 | 0 | 100 |
| 3.4 | 0 | 100 |

Preparation of 6-bromo-2-(4-fluorophenyl)-5-hydroxy-N-methylbenzofuran-3-carboxamide

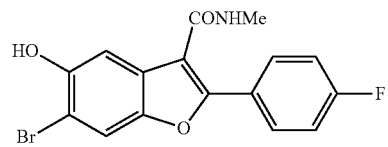

A solution of trichloroborane (1.0 M in DCM) (2.95 mL, 2.95 mmol) was added to a solution of of 6-bromo-2-(4-fluorophenyl)-5-isopropoxy-N-methylbenzofuran-3-carboxamide (300 mg, 0.738 mmol) in DCM (25 mL) at −78° C. The reaction mixture was allowed to stir at 0° for 5 min. After completion of the reaction (monitored by TLC), the reaction mixture was concentrated under reduced pressure to remove volatiles. The residue was diluted with ice cooled water, stirred for 5 min, the obtained solid filtered and dried under suction to afford 6-bromo-2-(4-fluorophenyl)-5-hydroxy-N-methylbenzofuran-3-carboxamide as a white solid. Yield: 250 mg, (92%). LCMS: (ES+) m/z=364.2 (M+H)⁺, Column-ACQUITY UPLC BEH C8 (50×2.1 mm; 1.7 μm), Mobile phase A: 10 mM Ammonium Acetate pH-5 adjusted with HCOOH:MeCN (95:5), Mobile phase B: 10 mM Ammonium Acetate pH-5 adjusted with HCOOH:MeCN (5:95), Flow: 0.8 ml/min, Rt: 0.94 min, wavelength: 220 nm.

| LCMS | | |
|---|---|---|
| Time | % A | % B |
| 0.0 | 95 | 5 |
| 1.1 | 5 | 95 |
| 1.7 | 5 | 95 |

Preparation of 5-(benzyloxy)-6-bromo-2-(4-fluorophenyl)-N-methylbenzofuran-3-carboxamide

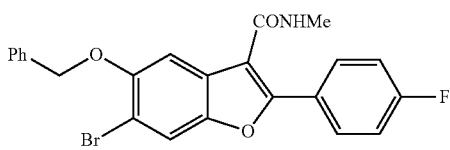

To a stirred mixture of 6-bromo-2-(4-fluorophenyl)-5-hydroxy-N-methylbenzofuran-3-carboxamide (200 mg, 0.549 mmol) and $K_2CO_3$ (152 mg, 1.098 mmol) in acetonitrile (30 mL) at room temperature was added benzyl bromide (0.098 mL, 0.824 mmol). The reaction mixture was stirred at room temperature for over 16 hr. After completion of the reaction (monitored by TLC), the reaction mixture was concentrated under reduced pressure. The residue was diluted with water, stirred for 10 min, and the solid filtered and dried under suction to afford 5-(benzyloxy)-6-bromo-2-(4-fluorophenyl)-N-methylbenzofuran-3-carboxamide as an off white solid. Yield: 220 mg, (88.35%). LCMS: (ES+) m/z=454.3 (M+H)$^+$, Column-ACQUITY UPLC BEH C8 (50×2.1 mm; 1.7 μm), Mobile phase A: 10 mM Ammonium Acetate pH-5 adjusted with HCOOH:MeCN (95:5), Mobile phase B: 10 mM Ammonium Acetate pH-5 adjusted with HCOOH:MeCN (5:95), Flow: 0.8 ml/min, Rt: 1.26 min, wavelength: 220 nm.

| LCMS | | |
|---|---|---|
| Time | % A | % B |
| 0.0 | 95 | 5 |
| 1.1 | 5 | 95 |
| 1.7 | 5 | 95 |

Preparation of 5-(benzyloxy)-2-(4-fluorophenyl)-6-hydroxy-N-methylbenzofuran-3-carboxamide

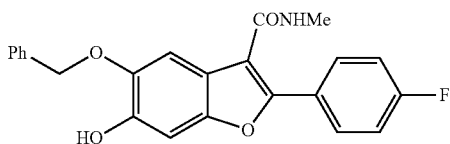

A mixture of 5-(benzyloxy)-6-bromo-2-(4-fluorophenyl)-N-methylbenzofuran-3-carboxamide (200 mg, 0.440 mmol) and KOH (99 mg, 1.761 mmol) in dioxane (10 mL)/water (10 mL) in a sealed tube capped with a rubber septum at room temperature was degassed and back filled with nitrogen (this was repeated twice). After which, 2-di-tert-butylphosphino-2',4',6'-triisopropyl biphenyl (18.69 mg, 0.044 mmol) and $Pd_2(dba)_3$ (20.16 mg, 0.022 mmol) were added to the mixture. The tube was tightly closed with a teflon cap and the reaction mixture heated to 100° C. and stirred at same temperature for 16 hr. After cooling to room temperature, completion of the reaction was confirmed by TLC. The reaction mixture was diluted with water, and acidify to pH~3.0 using 1.5N aq. HCl in ice-cold condition. The product was extracted with EtOAc (50 ml×3). The combined organic layers were washed with saturated brine solution, dried over $Na_2SO_4$ and concentrated under reduced pressure. The crude product obtained was purified via Combiflash using a 24 g silica gel column with 35% EtOAc in pet. ether as an eluent to afford 5-(benzyloxy)-2-(4-fluorophenyl)-6-hydroxy-N-methylbenzofuran-3-carboxamide as an off white solid. Yield: 110 mg, (63.95%). LCMS: (ES+) m/z=392.4 (M+H)$^+$, Column-ACQUITY UPLC BEH C8 (50×2.1 mm; 1.7 μm), Mobile phase A: 10 mM Ammonium Acetate pH-5 adjusted with HCOOH:MeCN (95:5), Mobile phase B: 10 mM Ammonium Acetate pH-5 adjusted with HCOOH:MeCN (5:95), Flow: 0.8 ml/min, Rt: 1.01 min, wavelength: 220 nm.

| LCMS | | |
|---|---|---|
| Time | % A | % B |
| 0.0 | 95 | 5 |
| 1.1 | 5 | 95 |
| 1.7 | 5 | 95 |

Preparation of 5-(benzyloxy)-2-(4-fluorophenyl)-6-isopropoxy-N-methylbenzofuran-3-carboxamide

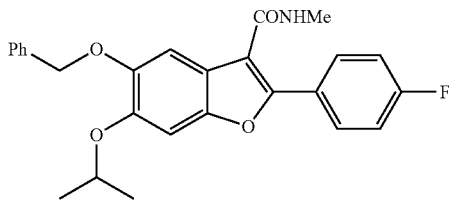

To a stirred solution of 5-(benzyloxy)-2-(4-fluorophenyl)-6-hydroxy-N-methylbenzofuran-3-carboxamide (100 mg, 0.255 mmol) in acetonitrile (20 mL) at room temperature was added potassium carbonate (70.6 mg, 0.511 mmol) followed by 2-bromopropane (0.029 mL, 0.307 mmol). The reaction mixture was heated to 70° C. and stirred at the same temperature for 16 hr. After cooled to room temperature, completion of the reaction was confirmed by TLC. The reaction mixture was concentrated under reduced pressure. The residue was diluted with water, stirred for 10 min and the solid filtered. The crude compound was triturated with pet. ether to obtained 5-(benzyloxy)-2-(4-fluorophenyl)-6-isopropoxy-N-methylbenzofuran-3-carboxamide as an off white solid. Yield: 105 mg, (94.80%). $^1$H NMR (400 MHz, DMSO-$d_6$) δ ppm=8.32 (d, J=4.4 Hz, 1H), 7.91-7.87 (m, 2H), 7.50 (d, J=7.3 Hz, 2H), 7.44-7.32 (m, 5H), 7.23 (s, 1H), 5.13 (s, 2H), 4.65 (quin, J=6.1 Hz, 1H), 2.83 (d, J=4.6 Hz, 3H), 1.31 (d, J=6.0 Hz, 6H). LCMS: (ES+) m/z=434.2 (M+H)$^+$, Column-Acentis Express C18 (50×2.1 mm; 2.7 um), Buffer: 10 mM Ammonium Formate in Water, Mobile phase A: Buffer:MeCN (98:2), Mobile phase B: Buffer:MeCN (2:98), Flow: 1.0 ml/min. Rt: 2.45 min, wavelength: 220 nm.

| LCMS | | |
|---|---|---|
| Time | % A | % B |
| 0.0 | 100 | 0 |
| 1.7 | 0 | 100 |
| 3.0 | 0 | 100 |
| 3.2 | 100 | 0 |

Preparation of 2-(4-fluorophenyl)-5-hydroxy-6-isopropoxy-N-methylbenzofuran-3-carboxamide

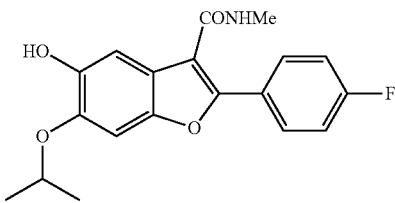

To a stirred solution of 5-(benzyloxy)-2-(4-fluorophenyl)-6-isopropoxy-N-methylbenzofuran-3-carboxamide (100 mg, 0.231 mmol) in ethyl acetate (15 mL) at room temperature was added palladium on carbon (10%, 20 mg, 0.019 mmol). The reaction mixture was stirred at room temperature under hydrogen pressure (using a rubber bladder filled with hydrogen) for 2 hr. After completion of the reaction (monitored by TLC), the reaction mixture was filtered through a celite pad, which was then washed with EtOAc. The filtrate was concentrated under reduced pressure to obtained 2-(4-fluorophenyl)-5-hydroxy-6-isopropoxy-N-methylbenzofuran-3-carboxamide as an off white solid. Yield: 70 mg, (88.60%). $^1$H NMR (300 MHz, CHLOROFORM-d) δ ppm=7.97 (dd, J=5.3, 9.0 Hz, 2H), 7.30-7.29 (m, 1H), 7.17 (t, J=8.7 Hz, 2H), 7.07 (s, 1H), 5.85 (br. s., 1H), 5.74 (s, 1H), 4.67 (td, J=6.1, 12.2 Hz, 1H), 3.04 (d, J=4.9 Hz, 3H), 1.46 (d, J=6.1 Hz, 6H). LCMS: (ES+) m/z=344.4 (M+H)$^+$, Column-ACQUITY UPLC BEH C8 (50×2.1 mm; 1.7 μm), Mobile phase A: 10 mM Ammonium Acetate pH-5 adjusted with HCOOH:MeCN (95:5), Mobile phase B: 10 mM Ammonium Acetate pH-5 adjusted with HCOOH:MeCN (5:95), Flow: 0.8 ml/min, Rt: 0.94 min, wavelength: 220 nm.

| LCMS | | |
|---|---|---|
| Time | % A | % B |
| 0.0 | 95 | 5 |
| 1.1 | 5 | 95 |
| 1.7 | 5 | 95 |

Preparation of 2-(4-fluorophenyl)-6-isopropoxy-3-(methylcarbamoyl)benzofuran-5-yl tri-fluoromethanesulfonate

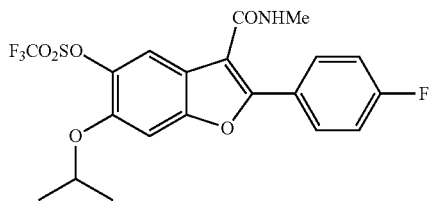

DMAP (49.8 mg, 0.408 mmol) followed by 1,1,1-trifluoro-N-phenyl-N-((trifluoromethyl) sulfonyl)methanesulfonamide (87 mg, 0.245 mmol) were added to a stirred solution of 2-(4-fluorophenyl)-5-hydroxy-6-isopropoxy-N-methylbenzofuran-3-carboxamide (70 mg, 0.204 mmol) in DMF (5.0 mL) at room temperature. The reaction mixture was stirred at room temperature for 16 hr. After completion of the reaction (monitored by TLC), the reaction mixture was poured into water and extracted with EtOAc (75 ml×3). The combined organic layers were washed with saturated brine solution, dried over anhydrous Na$_2$SO$_4$, filtered and concentrated under reduced pressure. The crude product obtained was purified via Combiflash using a 12 g silica gel column with 22% EtOAc in pet. ether as an eluent to obtain 2-(4-fluorophenyl)-6-isopropoxy-3-(methylcarbamoyl)benzofuran-5-yl trifluoromethanesulfonate as white solid. Yield: 75 mg, (77.38%). LCMS: (ES+) m/z=476.3 (M+H)$^+$, Column-Acentis Express C18 (50×2.1 mm; 2.7 um), Buffer: 10 mM Ammonium Formate in Water, Mobile phase A: Buffer:MeCN (98:2), Mobile phase B: Buffer:MeCN (2:98), Flow: 1.0 ml/min. Rt: 2.39 min, wavelength: 220 nm.

| LCMS | | |
|---|---|---|
| Time | % A | % B |
| 0.0 | 100 | 0 |
| 1.7 | 0 | 100 |
| 3.4 | 0 | 100 |

Preparation of methyl 5-(2-(4-fluorophenyl)-6-isopropoxy-3-(methylcarbamoyl)benzo furan-5-yl)-2-methoxybenzoate

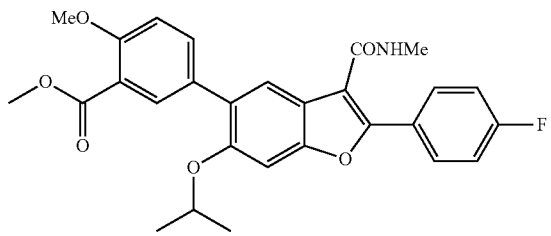

A mixture of 2-(4-fluorophenyl)-6-isopropoxy-3-(methylcarbamoyl)benzofuran-5-yl trifluoromethanesulfonate (55 mg, 0.116 mmol), methyl 2-methoxy-5-(4,4,5,5-tetramethyl-1,3,2-dioxaborolan-2-yl)benzoate (40.6 mg, 0.139 mmol) and cesium carbonate (75 mg, 0.231 mmol) in dioxane (10 mL)/water (1.0 mL) in a pressure tube capped with a rubber septum at room temperature was degassed and back filled with nitrogen. After which, tetrakis(triphenyl phosphine)palladium(0) (13.37 mg, 0.012 mmol) was added to the reaction mixture. The reaction mixture was heated to 100° C. and stirred at same temperature for 16 hr. After cooling to room temperature, completion of the reaction was confirmed by TLC. The reaction mixture was filtered through a celite pad, which was then washed with EtOAc. The filtrate was concentrated under reduced pressure, and the crude product purified via Combiflash using a 12 g silica gel column with 55% EtOAc in pet. ether as an eluent to afford methyl 5-(2-(4-fluorophenyl)-6-isopropoxy-3-(methylcarbamoyl)benzofuran-5-yl)-2-methoxybenzoate as an off white solid. Yield: 45 mg, (78.94%). $^1$H NMR (300 MHz, CHLOROFORM-d) δ ppm=8.04 (d, J=2.3 Hz, 1H), 7.95 (dd, J=5.4, 8.9 Hz, 2H), 7.72-7.67 (m, 2H), 7.22-7.17 (m, 2H), 7.14 (s, 1H), 7.04 (d, J=8.6 Hz, 1H), 5.86 (bs, 1H), 4.50 (quin, J=6.1 Hz, 1H), 3.98 (s, 3H), 3.93 (s, 3H), 3.02 (d, J=4.9 Hz, 3H), 1.32 (d, J=6.0 Hz, 6H). LCMS: (ES+) m/z=492.4 (M+H)$^+$, Column-ACQUITY UPLC BEH C8 (50×2.1 mm; 1.7 μm), Mobile phase A: 10 mM Ammonium Acetate pH-5 adjusted with HCOOH:MeCN (95:5), Mobile phase B: 10 mM Ammonium Acetate pH-5 adjusted with HCOOH:MeCN (5:95), Flow: 0.8 ml/min, Rt: 1.14 min, wavelength: 220 nm.

| LCMS | | |
|---|---|---|
| Time | % A | % B |
| 0.0 | 95 | 5 |
| 1.1 | 5 | 95 |
| 1.7 | 5 | 95 |

Preparation of 5-(2-(4-fluorophenyl)-6-isopropoxy-3-(methylcarbamoyl)benzofuran-5-yl)-2-methoxybenzoic acid

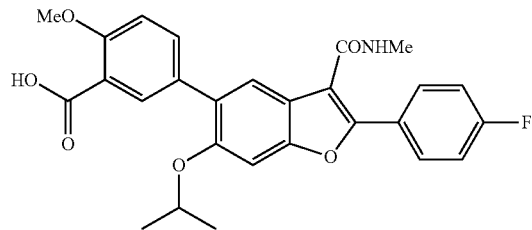

A sodium hydroxide solution (1.0 M in water) (0.458 mL, 0.458 mmol) was added to a stirred solution of methyl 5-(2-(4-fluorophenyl)-6-isopropoxy-3-(methylcarbamoyl) benzofuran-5-yl)-2-methoxybenzoate (45 mg, 0.092 mmol) in MeOH (5 mL)/THF (5 mL) at room temperature. The reaction mixture was stirred at room temperature for 16 hr. After completion of the reaction (monitored by TLC), the reaction mixture was concentrated under reduced pressure. The residue was diluted with water, acidified by using 1.5N HCl to the pH~3 under ice-cold condition. The mixture was stirred for 5 min and filtered to afford 5-(2-(4-fluorophenyl)-6-isopropoxy-3-(methyl carbamoyl)benzofuran-5-yl)-2-methoxybenzoic acid as a white solid. Yield: 37 mg, (83%). $^1$H NMR (300 MHz, DMSO-d$_6$) δ ppm=12.60 (bs, 1H), 8.42 (d, J=5.1 Hz, 1H), 7.99-7.92 (m, 2H), 7.84 (s, 1H), 7.67 (d, J=8.7 Hz, 1H), 7.46 (s, 2H), 7.37 (t, J=8.9 Hz, 2H), 7.19 (d, J=8.5 Hz, 1H), 4.72-4.67 (m, 1H), 3.87 (s, 3H), 2.82 (d, J=4.4 Hz, 3H), 1.25 (d, J=5.9 Hz, 6H). LCMS: (ES+) m/z=478.4 (M+H)$^+$, Column-ACQUITY UPLC BEH C8 (50×2.1 mm; 1.7 μm), Mobile phase A: 10 mM Ammonium Acetate pH-5 adjusted with HCOOH:MeCN (95:5), Mobile phase B: 10 mM Ammonium Acetate pH-5 adjusted with HCOOH:MeCN (5:95), Flow: 0.8 ml/min, Rt: 0.81 min, wavelength: 220 nm.

| LCMS | | |
|---|---|---|
| Time | % A | % B |
| 0.0 | 95 | 5 |
| 1.1 | 5 | 95 |
| 1.7 | 5 | 95 |

Preparation of methyl 5-(6-ethoxy-2-(4-fluorophenyl)-3-(methylcarbamoyl)benzofuran-5-yl)-2-ethylbenzoate

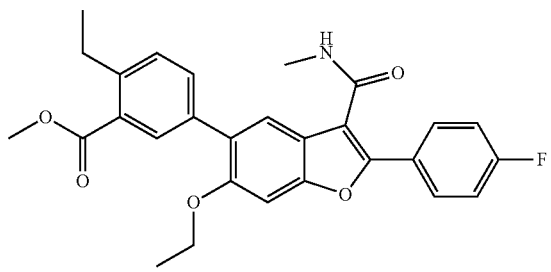 [SMILES: CCOc1cc2oc(-c3ccc(F)cc3)c(C(=O)NC)c2cc1-c1ccc(CC)c(C(=O)OC)c1]

To a solution of 6-ethoxy-2-(4-fluorophenyl)-3-(methylcarbamoyl)benzofuran-5-yl trifluoro methanesulfonate (0.1 g, 0.217 mmol) and methyl 2-ethyl-5-(4,4,5,5-tetramethyl-1,3,2-dioxaborolan-2-yl)benzoate (0.094 g, 0.325 mmol) (prepared from methyl 5-chloro-2-hydroxybenzoate in three steps as described in Scheme 7) in 1,4-dioxane (4 mL)/water (0.5 mL) was added potassium phosphate, dibasic (0.094 g, 0.542 mmol) and degassed for 5 min. The mixture was then added PdCl$_2$(dppf)-CH$_2$Cl$_2$ adduct (8.85 mg, 0.0108 mmol), and degassed again for 5 min. The resulting reaction mixture was stirred at 85° C. for 4 hrs. The mixture was passed through a pad of celite and the celite bed washed with EtOAc (50) ml. The organic layer was dried over Na$_2$SO$_4$, filtered and concentrated. The crude product was purified by Combiflash using a 18 g silica gel column and 25% EtOAc in petroleum ether as an eluant to obtain methyl 5-(6-ethoxy-2-(4-fluorophenyl)-3-(methylcarbamoyl)benzofuran-5-yl)-2-ethylbenzoate as a white solid. Yield: 0.03 g (29%). LCMS: (ES+) m/z=476.14 (M+H)$^+$. Column-Ascentis Express C18 (50×2.1 mm-2.7 μm). Mobile phase A: 10 mM NH$_4$COOH (in water pH 4.5). Mobile phase B: MeCN. Flow: 1 ml/min., Rt min: 2.41, wavelength: 220 nm, and gradient:

| Time | % A | % B |
|---|---|---|
| 0.0 | 100.0 | 0.0 |
| 1.7 | 0.0 | 100.0 |
| 3.4 | 0.0 | 100.0 |

Preparation of 5-(6-ethoxy-2-(4-fluorophenyl)-3-(methylcarbamoyl)benzofuran-5-yl)-2-ethyl benzoic acid

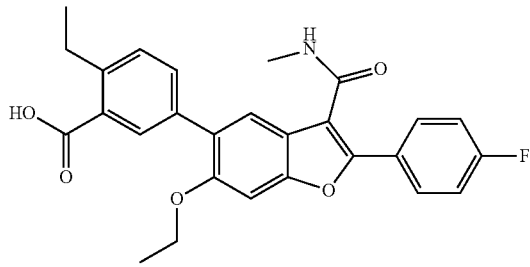 [SMILES: CCOc1cc2oc(-c3ccc(F)cc3)c(C(=O)NC)c2cc1-c1ccc(CC)c(C(=O)O)c1]

To a mixture of methyl 5-(6-ethoxy-2-(4-fluorophenyl)-3-(methylcarbamoyl)benzofuran-5-yl)-2-ethylbenzoate (0.03 g, 0.063 mmol) in THF (2 mL)./MeOH (2 mL) was added NaOH (7.57 mg, 0.189 mmol) and water (1 mL). The resulting reaction mixture was stirred at 25° C. for 2 hrs. The mixture was evaporated to remove the organic solvent and the pH was adjusted to 2.0 with 1.5 N HCl. The solid precipitated out was filtered and dried under vacuum to give 5-(6-ethoxy-2-(4-fluorophenyl)-3-(methylcarbamoyl)benzofuran-5-yl)-2-ethylbenzoic acid as a white solid. Yield: 0.028 g (96%). LCMS: (ES+) m/z=462.2 (M+H)$^+$. Column-Ascentis Express C18 (50×2.1 mm-2.7 μm) M (=Mobile) phase A: 2% MeCN-98% H$_2$O-10 mM NH$_4$COOH, Mphase B: 98% MeCN-2% H$_2$O-10 mM NH$_4$COOH Flow=1 ml/min, Rt min: 2.04, wavelength: 220 nm., with gradient:

| Time | % A | % B |
| --- | --- | --- |
| 0.0 | 100.0 | 0.0 |
| 1.7 | 0.0 | 100.0 |
| 3.4 | 0.0 | 100.0 |

Preparation of 2-(4-fluorophenyl)-5-isopropoxy-N-methyl-6-propoxybenzofuran-3-carboxamide

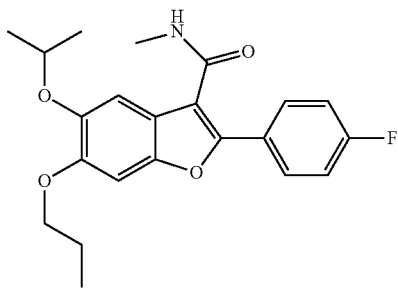 [SMILES: CCCOc1cc2oc(-c3ccc(F)cc3)c(C(=O)NC)c2cc1OC(C)C]

To a solution of 2-(4-fluorophenyl)-6-hydroxy-5-isopropoxy-N-methylbenzofuran-3-carbox-amide (0.2 g, 0.582 mmol) in DMF (4 mL) was added cesium carbonate (0.380 g, 1.165 mmol) followed by 1-iodopropane (0.068 mL, 0.699 mmol). The reaction mixture was allowed to stir at 25° C. for 1 hour. To the reaction mixture was added water (50 ml), and extracted with ethyl acetate (3×25 ml). The combined organic extracts were dried Na$_2$SO$_4$, filtered and the filtrate concentrated under vacuum to provide 2-(4-fluorophenyl)-5-isopropoxy-N-methyl-6-propoxybenzofuran-3-carboxamide as a white solid. Yield: 0.21 g (94%). LCMS: (ES+) m/z=(M+H)$^+$386.4. Column-ACQUITY UPLC BEH C18 (50×2.1 mm; 1.7 μm). M phase A: 0.1% TFA in water, M phase B: Acetonitrile. Flow: 0.8 ml/Min. Rt min: 1.07, wavelength: 220 nm., with gradient:

| Time | % A | % B |
| --- | --- | --- |
| 0 | 98 | 2 |
| 1.0 | 2 | 98 |
| 1.6 | 2 | 98 |

$^1$H NMR (400 MHz, CHLOROFORM-d) δ ppm=7.89-7.85 (m, 2H), 7.33 (s, 1H), 7.17-7.13 (t, J=8.8, 2H), 7.04 (s, 1H), 5.78 (br. s., 1H), 4.48-4.45 (td, J=6.1, 12.2 Hz, 1H), 4.00-3.97 (t, J=6.6 Hz, 2H), 3.00 (d, J=4.9 Hz, 3H), 1.91-1.86 (m, 2H), 1.36 (d, J=6.1 Hz, 6H), 1.12 (t, J=7.4 Hz, 3H).

Preparation of 2-(4-fluorophenyl)-5-hydroxy-N-methyl-6-propoxybenzofuran-3-carboxamide

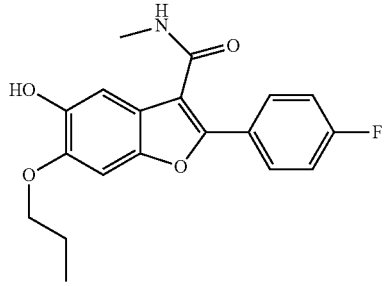 [SMILES: CCCOc1cc2oc(-c3ccc(F)cc3)c(C(=O)NC)c2cc1O]

To a solution of 2-(4-fluorophenyl)-5-isopropoxy-N-methyl-6-propoxybenzofuran-3-carboxamide (0.21 g, 0.545 mmol) in DCM (2 mL) at −78° C. was slowly added boron trichloride (1.635 mL, 1.635 mmol) dropwise, and the reaction was then allowed to stir at 0° C. for 2 hours. After completion of the reaction, the mixture was quenched with ice-cold water at the same temperature and extracted with DCM (2×10 ml). The combined organic extracts were dried over Na$_2$SO$_4$, filtered and the filtrate concentrated to give 2-(4-fluorophenyl)-5-hydroxy-N-methyl-6-propoxybenzofuran-3-carboxamide as a white solid. Yield: 0.180 g, (96%).
$^1$H NMR (400 MHz, CHLOROFORM-d) δ ppm=7.95-7.92 (m, 2H), 7.26 (s, 1H), 7.16 (d, J=8.8, 2H), 7.028 (s, 1H), 5.85 (br. s., 1H), (4.08 (t, J=6.6 Hz, 2H), 3.02 (d, J=4.9 Hz, 3H), 1.93-1.88 (sxt, J=7.1 Hz, 2H), 1.11 (t, J=7.4 Hz, 3H). LCMS: (ES+) m/z=344.3 (M+H)$^+$. Column-ACQUITY UPLC BEH C18 (50×2.1 mm; 1.7 μm). M phase A: 0.1% TFA in water, M phase B: Acetonitrile. Flow: 0.8 ml/Min. Rt min: 0.92, wavelength: 220 nm., with gradient:

| Time | % A | % B |
| --- | --- | --- |
| 0 | 98 | 2 |
| 1.0 | 2 | 98 |
| 1.6 | 2 | 98 |

Preparation of 2-(4-fluorophenyl)-3-(methylcarbamoyl)-6-propoxybenzofuran-5-yl trifluoromethanesulfonate

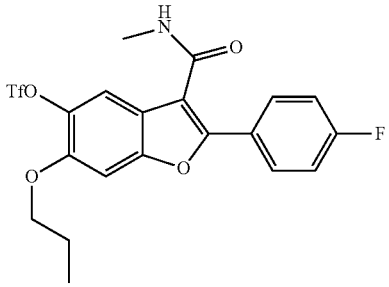 [SMILES: CCCOc1cc2oc(-c3ccc(F)cc3)c(C(=O)NC)c2cc1OS(=O)(=O)C(F)(F)F]

To a mixture of 2-(4-fluorophenyl)-5-hydroxy-N-methyl-6-propoxybenzofuran-3-carboxamide (0.18 g, 0.524 mmol) in DMF (4 mL) was added DMAP (0.192 g, 1.573 mmol). 1,1,1-Trifluoro-N-phenyl-N-(trifluoromethyl)sulfonylmethane sulfonamide (0.206 g, 0.577 mmol) was added to the mixture portion-wise. The mixture was stirred at 25° C. for 12 hours. The reaction was quenched with ice-cold water, the solid formed was filtered and dried under suction to give 2-(4-fluorophenyl)-3-(methylcarbamoyl)-6-propoxybenzofuran-5-yl trifluoromethanesulfonate as a white solid: 0.210 g (84%). $^1$H NMR (400 MHz, CHLOROFORM-d) δ ppm=7.86-7.82 (m, 2H), 7.74 (s, 1H), 7.21-7.17 (m, 2H), 7.14 (s, 1H), 5.74 (br. s., 1H), 4.08 (t, J=6.5 Hz, 2H), 2.99-2.97 (d, J=4.9 Hz, 3H), 1.95-1.89 (m, 2H), 1.12 (t, J=7.4 Hz, 3H). LCMS: (ES+) m/z=476.2 (M+H)$^+$. Column-ACQUITY UPLC BEH C18 (50×2.1 mm; 1.7 μm). M phase A: 0.1% TFA in water, M phase B: Acetonitrile. Flow: 0.8 ml/Min., Rt min: 1.12, wavelength: 220 nm., with gradient:

| Time | % A | % B |
|---|---|---|
| 0 | 98 | 2 |
| 1.0 | 2 | 98 |
| 1.6 | 2 | 98 |

Preparation of methyl 5-(2-(4-fluorophenyl)-3-(methylcarbamoyl)-6-propoxybenzofuran-5-yl)-2-methoxybenzoate

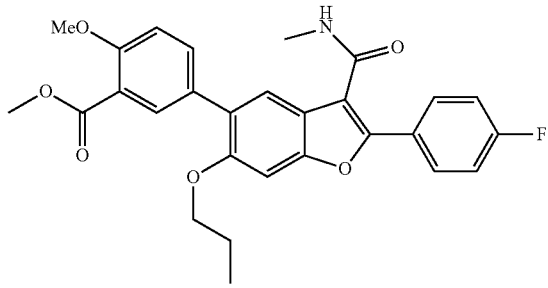 [SMILES: CCCOc1cc2oc(-c3ccc(F)cc3)c(C(=O)NC)c2cc1-c1ccc(OC)c(C(=O)OC)c1]

To a mixture of 2-(4-fluorophenyl)-3-(methylcarbamoyl)-6-propoxybenzofuran-5-yl trifluoromethanesulfonate (0.15 g, 0.316 mmol) and methyl 2-methoxy-5-(4,4,5,5-tetramethyl-1,3,2-dioxaborolan-2-yl)benzoate (0.138 g, 0.473 mmol) in dioxane (4 mL)/water (0.5 mL) was added cesium carbonate (0.257 g, 0.789 mmol) and the mixture degassed for 5 min. Tetrakis(triphenylphosphine)palladium (0) (0.018 g, 0.016 mmol) was added to the mixture, which was then degassed again for 5 min. The resulting reaction mixture was stirred at 90° C. The reaction mixture was filtered through a celite pad and the celite washed thoroughly with ethyl acetate (50 ml). The filtrate was washed with water (50 ml), and the organic layer was then dried over Na$_2$SO$_4$, filtered and the filtrate was concentrated. The crude mixture was purified by silica gel chromatography using 25% EtOAc in pet. ether as an eluent to obtain methyl 5-(2-(4-fluorophenyl)-3-(methylcarbamoyl)-6-propoxybenzofuran-5-yl)-2-methoxybenzoate as a yellow solid. Yield: 70 mg (45%). $^1$H NMR (400 MHz, CHLOROFORM-d) δ ppm=8.03 (d, J=2.4 Hz, 1H), 7.95-7.91 (m, 2H), 7.68-7.65 (m, 2H), 7.19-7.15 (m, 2H), 7.09 (s, 1H), 7.03 (d, J=8.7 Hz, 1H), 5.85 (br. s., 1H), 4.14-4.09 (m, 5H), 3.90 (s, 3H), 3.01 (d, J=4.9 Hz, 3H), 1.80-1.75 (m, 2H), 1.01 (t, J=7.4 Hz, 3H). LCMS: (ES+) m/z observed=491.9. Column-ACQUITY UPLC BEH C8 (50×2.1 mm; 2.7 μm). M phase A: 5 mM Ammonium Acetate:MeCN (95:5). M phaseB: 5 mM Ammonium Acetate:MeCN (5:95). Flow: 0.8 ml/Min., Rt min: 2.46, wavelength: 220 nm., with gradient:

| Time | % A | % B |
|---|---|---|
| 0.0 | 100.0 | 0.0 |
| 1.7 | 0.0 | 100.0 |
| 3.0 | 0.0 | 100.0 |
| 3.2 | 100.0 | 0.0 |

Preparation of 5-(2-(4-fluorophenyl)-3-(methylcarbamoyl)-6-propoxybenzofuran-5-yl)-2-methoxybenzoic acid

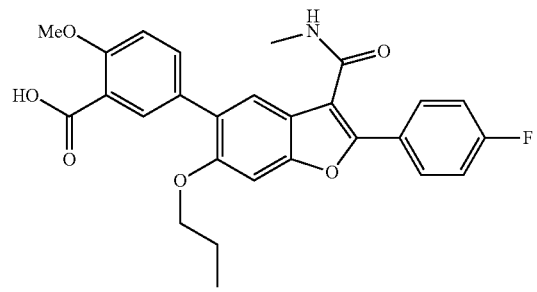 [SMILES: CCCOc1cc2oc(-c3ccc(F)cc3)c(C(=O)NC)c2cc1-c1ccc(OC)c(C(=O)O)c1]

To a solution of methyl 5-(2-(4-fluorophenyl)-3-(methylcarbamoyl)-6-propoxybenzofuran-5-yl)-2-methoxybenzoate (0.07 g, 0.142 mmol) in THF (2 mL) and MeOH (2 mL) was added NaOH (0.017 g, 0.427 mmol) and water (1 mL). The resulting reaction mixture was stirred at 25° C. for 2 hrs. The solvent was removed under vacuum, and the residue diluted with water (20 ml) and acidified with 1.5N HCl solution. The solid formed was filtered and dried to give 5-(2-(4-fluorophenyl)-3-(methylcarbamoyl)-6-propoxybenzofuran-5-yl)-2-methoxybenzoic acid as a white solid. Yield: 55 mg, (81%). LCMS: for (ES−) m/z=475.9 (M+H)$^-$ found. Column-ACQUITY UPLC BEH C8 (50×2.1 mm; 2.7 μm). M phase A: 5 mM Ammonium Acetate: MeCN (95:5). M phase B: 5 mM Ammonium Acetate:MeCN (5:95). Flow: 0.8 ml/min. Rt min: 1.96, wavelength: 220 nm., and gradient:

| Time | % A | % B |
| --- | --- | --- |
| 0.0 | 100.0 | 0.0 |
| 1.7 | 0.0 | 100.0 |
| 3.0 | 0.0 | 100.0 |
| 3.2 | 100.0 | 0.0 |

Preparation of 2-(4-fluorophenyl)-6-isobutoxy-5-isopropoxy-N-methylbenzofuran-3-carboxamide

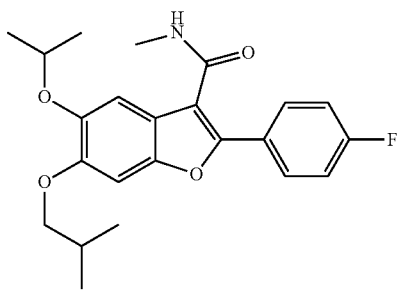 [SMILES: CNC(=O)c1c(-c2ccc(F)cc2)oc2cc(OCC(C)C)c(OC(C)C)cc12]

To a solution of 2-(4-fluorophenyl)-6-hydroxy-5-isopropoxy-N-methylbenzofuran-3-carboxamide (0.2 g, 0.582 mmol) in DMF (4 mL) was added cesium carbonate (0.380 g, 1.165 mmol) followed by 1-iodo-2-methylpropane (0.081 mL, 0.699 mmol). The reaction mixture was heated to 50° C. and allowed to stir at this same temperature for 12 hours. To the reaction mixture was added water and then extracted with ethylacetate (3×10) ml. The organic layer was dried over $Na_2SO_4$, filtered, and the filtrate concentrated. The crude product was purified by Combiflash silica gel column chromatography using 30% EtOAc in Petroleum ether as an eluant and to give 2-(4-fluorophenyl)-6-isobutoxy-5-isopropoxy-N-methylbenzofuran-3-carboxamide as a white solid. Yield: 0.22 g (95%). $^1$H NMR (400 MHz, CHLOROFORM-d) δ ppm=7.90-7.85 (m, 2H), 7.33 (s, 1H), 7.18-7.13 (m, 2H), 7.04 (s, 1H), 5.78 (br, s, 1H), 4.47 (quin, J=6.1 Hz, 1H), 3.78 (d, J=6.5 Hz, 2H), 3.00 (d, J=4.9 Hz, 3H), 2.19 (td, J=6.7, 13.3 Hz, 1H), 1.35 (d, J=6.1 Hz, 6H), 1.07 (d, J=6.7 Hz, 6H). LCMS: (ES+) m/z=400.2 (M+H)$^+$. Column-ACQUITY UPLC BEH C18 (50×2.1 mm; 1.7 μm). M phase A: 0.1% TFA in water. M phase B: Acetonitrile. Flow: 0.8 ml/min., Rt min: 1.14, wavelength: 220 nm., and gradient:

| Time | % A | % B |
| --- | --- | --- |
| 0 | 98 | 2 |
| 1.0 | 2 | 98 |
| 1.6 | 2 | 98 |

Preparation of 2-(4-fluorophenyl)-5-hydroxy-6-isobutoxy-N-methylbenzofuran-3-carboxamide

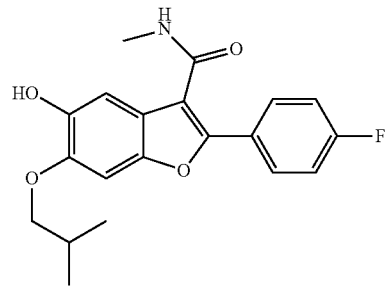 [SMILES: CNC(=O)c1c(-c2ccc(F)cc2)oc2cc(OCC(C)C)c(O)cc12]

To a solution of 2-(4-fluorophenyl)-6-isobutoxy-5-isopropoxy-N-methylbenzofuran-3-carboxamide (0.21 g, 0.526 mmol) in DCM (2 mL) at −78° C. was added boron trichloride (1.577 mL, 1.577 mmol) dropwise and slowly. The reaction was allowed to stir at 0° C. for 2 hours, and then quenched with ice-cold water at the same temperature. The mixture was extracted with DCM (2×100) ml. The organic layer was dried over $Na_2SO_4$ and concentrated to give 2-(4-fluorophenyl)-5-hydroxy-6-isobutoxy-N-methylbenzofuran-3-carboxamide as a pale yellow solid. Yield: 0.18 g (96%). $^1$H NMR (400 MHz, CHLOROFORM-d) δ ppm=7.95-7.92 (m, 2H), 7.27-7.25 (m, 1H), 7.16-7.12 (m, 2H), 7.02 (s, 1H), 5.63 (s, 1H), 3.88 (d, J=6.5 Hz, 2H), 3.02 (d, J=4.9 Hz, 3H), 2.23-2.16 (td, J=6.7, 13.3 Hz, 1H), 1.12 (d, J=6.8 Hz, 6H). LCMS: for (ES+) m/z=358.1 (M+H)$^+$. Column-ACQUITY UPLC BEH C18 (50×2.1 mm; 1.7 μm). M phase A: 0.1% TFA in water. M phase B: Acetonitrile. Flow: 0.8 ml/min., Rt min: 0.97, wavelength: 220 nm., and gradient:

| Time | % A | % B |
| --- | --- | --- |
| 0 | 98 | 2 |
| 1.0 | 2 | 98 |
| 1.6 | 2 | 98 |

Preparation of 2-(4-fluorophenyl)-6-isobutoxy-3-(methylcarbamoyl)benzofuran-5-yl trifluoromethanesulfonate

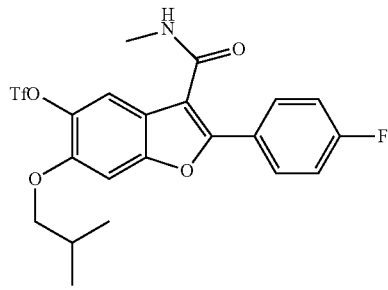 [SMILES: CNC(=O)c1c(-c2ccc(F)cc2)oc2cc(OCC(C)C)c(OS(=O)(=O)C(F)(F)F)cc12]

To a solution of 2-(4-fluorophenyl)-5-hydroxy-6-isobutoxy-N-methylbenzofuran-3-carboxamide (0.18 g, 0.504 mmol) in DMF (4 mL) was added DMAP (0.185 g, 1.511 mmol) followed by 1,1,1-trifluoro-N-phenyl-N-(trifluoromethyl)sulfonylmethane sulfonamide (0.198 g, 0.554 mmol) portionwise. The reaction was continued stirring at 25° C. for 12 hours. The reaction mixture was quenched with ice water, the solid formed was filtered and dried under suction to get 2-(4-fluorophenyl)-6-isobutoxy-3-(methylcarbamoyl) benzofuran-5-yl trifluoromethanesulfonate as a white solid. Yield: 0.09 g (37%). $^1$H NMR (400 MHz, CHLOROFORM-d) δ=7.86-7.82 (m, 2H), 7.74 (s, 1H), 7.22-7.17 (m, 2H), 7.14 (s, 1H), 5.75 (br. s., 1H), 3.86 (d, J=6.4 Hz, 2H), 2.98 (d, J=4.9 Hz, 3H), 2.23-2.21 (m, 1H), 1.10 (d, J=6.8 Hz, 6H). LCMS: (ES+) m/z=490.2 (M+H)$^+$. Column-ACQUITY UPLC BEH C18 (50×2.1 mm; 1.7 μm). M phase A: 0.1% TFA in water M phase B: Acetonitrile. Flow: 0.8 ml/min., Rt min: 1.15, wavelength: 220 nm., and gradient:

| Time | % A | % B |
|------|-----|-----|
| 0    | 98  | 2   |
| 1.0  | 2   | 98  |
| 1.6  | 2   | 98  |

Preparation of methyl 5-(2-(4-fluorophenyl)-6-isobutoxy-3-(methylcarbamoyl) benzofuran-5-yl)-2-methoxybenzoate

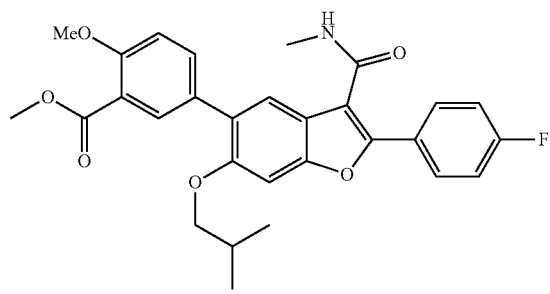 [SMILES: CNC(=O)c1c(-c2ccc(F)cc2)oc2cc(OCC(C)C)c(-c3ccc(OC)c(C(=O)OC)c3)cc12]

To a solution of 2-(4-fluorophenyl)-6-isobutoxy-3-(methylcarbamoyl)benzofuran-5-yl trifluoro methanesulfonate (0.08 g, 0.163 mmol) and methyl 2-methoxy-5-(4,4,5,5-tetramethyl-1,3,2-dioxaborolan-2-yl)benzoate (0.072 g, 0.245 mmol) in 1,4-dioxane (4 mL)/water (0.5 mL) was added cesium carbonate (0.133 g, 0.409 mmol), and the mixture degassed for 5 min. Tetrakis(triphenylphosphine) palladium(0) (9.44 mg, 0.0082 mmol) was added to the mixture, which was then degassed again for 5 min. The resulting reaction mixture was stirred at 90° C. for 2 hours. The reaction mixture was passed through a celite pad, and the pad was washed thoroughly with ethyl acetate (50 ml). To the organic layer was washed with water (50 ml). The organic layer was dried over Na$_2$SO$_4$, filtered and the filtrate was concentrated. The crude product was purified by Combiflash silica gel chromatography using 15% EtOAc in Petroleum ether as an eluant using to get methyl 5-(2-(4-fluorophenyl)-6-isobutoxy-3-(methylcarbamoyl)benzofuran-5-yl)-2-methoxybenzoate as a white solid. Yield: 0.05 (61%). LCMS: (ES+) m/z=506.3 (M+H)$^+$. Column-ACQUITY UPLC BEH C18 (50×2.1 mm; 1.7 μm). M phase A: 0.1% TFA in water. M phase B: Acetonitrile. Flow: 0.8 ml/min., Rt min: 1.12, wavelength: 220 nm., and gradient:

| Time | % A | % B |
|------|-----|-----|
| 0    | 98  | 2   |
| 1.0  | 2   | 98  |
| 1.6  | 2   | 98  |

Preparation of 5-(2-(4-fluorophenyl)-6-isobutoxy-3-(methylcarbamoyl)benzofuran-5-yl)-2-methoxybenzoic acid

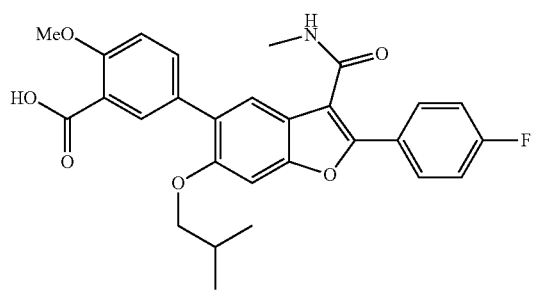 [SMILES: CNC(=O)c1c(-c2ccc(F)cc2)oc2cc(OCC(C)C)c(-c3ccc(OC)c(C(=O)O)c3)cc12]

To a solution of methyl 5-(2-(4-fluorophenyl)-6-isobutoxy-3-(methylcarbamoyl)benzofuran-5-yl)-2-methoxybenzoate (0.05 g, 0.099 mmol) in a mixture of THF (2 mL) and MeOH (2 mL) was added NaOH (0.012 g, 0.297 mmol) and water (1 mL). The resulting reaction mixture was stirred at 25° C. for 2 hrs. The solvent was removed under vacuum, and the residue diluted with water (5 ml) and acidified to pH 2.0 with 1.5N HCl solution. The solid formed was filtered and dried to give 5-(2-(4-fluorophenyl)-6-isobutoxy-3-(methylcarbamoyl)benzofuran-5-yl)-2-methoxybenzoic acid as a white solid. Yield: 0.028 g, (58%). $^1$H NMR (400 MHz, DMSO-d$_6$) δ ppm=8.41 (d, J=4.6 Hz, 1H), 7.98-7.94 (m, 2H), 7.86 (d, J=2.4 Hz, 1H), 7.67 (dd, J=2.4, 8.6 Hz, 1H), 7.48 (s, 1H), 7.42 (s, 1H), 7.40-7.34 (m, 2 H), 7.20 (d, J=8.8 Hz, 1H), 3.87 (s, 5H), 2.83 (d, J=4.6 Hz, 3H), 2.00-1.96 (m, 1H), 0.94 (d, J=6.7 Hz, 6H). LCMS: (ES+) m/z=492.3 (M+H)$^+$. Column-ACQUITY UPLC BEH C18 (50×2.1 mm; 1.7 μm). M phase A: 0.1% TFA in water. M phase B: Acetonitrile. Flow: 0.8 ml/min., Rt min: 1.04, wavelength: 220 nm., and gradient:

| Time | % A | % B |
|------|-----|-----|
| 0    | 98  | 2   |
| 1.0  | 2   | 98  |
| 1.6  | 2   | 98  |

Preparation of 2-(4-fluorophenyl)-5-isopropoxy-N-methyl-6-(4,4,5,5-tetramethyl-1,3,2-dioxaborolan-2-yl)benzofuran-3-carboxamide

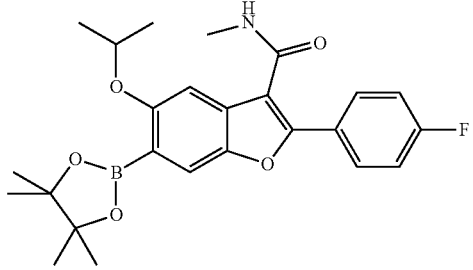 [SMILES: CNC(=O)c1c(-c2ccc(F)cc2)oc2cc(B3OC(C)(C)C(C)(C)O3)c(OC(C)C)cc12]

To a mixture of 6-bromo-2-(4-fluorophenyl)-5-isopropoxy-N-methylbenzofuran-3-carboxamide (4.0 g, 9.85 mmol) and bis(pinacolato)diboron (3.75 g, 14.77 mmol) in dioxane (100 mL) in a 250 ml round-bottomed flask was added potassium acetate (2.416 g, 24.62 mmol) and the mixture degassed for 5 min. PdCl$_2$(dppf)-CH$_2$Cl$_2$ adduct (0.402 g, 0.492 mmol) was added to the mixture, which was then degassed again for 5 min. The resulting reaction mixture was stirred at 90° C. for 12 hours. The TLC analysis showed formation of product. The reaction mixture was filtered through a celite bed, and the celite bed washed with EtOAc (50) ml. The organic layer was then dried over Na$_2$SO$_4$, filtered and concentrated. The crude product was purified by Combiflash silica gel column chromatography using 30% EtOAc in Petroleum ether as an eluant to give 2-(4-fluorophenyl)-5-isopropoxy-N-methyl-6-(4,4,5,5-tetramethyl-1,3,2-dioxaborolan-2-yl)benzofuran-3-carboxamide as a white solid. Yield: 3.6 g (81%). LCMS: (ES+) m/z=454 (M+H)$^+$. Column-ACQUITY UPLC BEH C18 (50λ2.1 mm; 1.7 μm). M phase A: 0.1% TFA in water, M phase B: Acetonitrile. Flow: 0.8 ml/min., Rt min: 1.14, wavelength: 220 nm., and gradient:

| Time | % A | % B |
|---|---|---|
| 0 | 98 | 2 |
| 1.0 | 2 | 98 |
| 1.6 | 2 | 98 |

Preparation of 2-(4-fluorophenyl)-6-hydroxy-5-isopropoxy-N-methyl-benzofuran-3-carboxamide

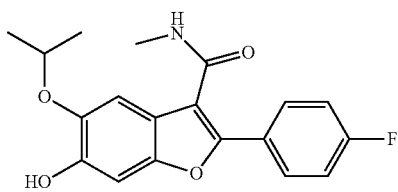 [SMILES: CNC(=O)c1c(-c2ccc(F)cc2)oc2cc(O)c(OC(C)C)cc12]

To a solution of 2-(4-fluorophenyl)-5-isopropoxy-N-methyl-6-(4,4,5,5-tetramethyl-1,3,2-dioxa borolan-2-yl)benzofuran-3-carboxamide (3.6 g, 7.94 mmol) in ethyl acetate (80 mL) was added hydrogen peroxide (24.34 mL, 238 mmol) dropwise and slowly for 15 min. Then the reaction was stirred at 25° C. for 12 hours. The TLC showed formation of product. The aqueous layer was separated. Aqueous sodium thiosulphate was added slowly to the ethyl acetate layer under cooling condition. After quenching the organic layer was separated. The aqueous layer was extracted with (2×100 ml) ethyl acetate, and the organic layer separated. The combined organic layers were concentrated under reduced pressure at 40° C. to obtain a pale yellow liquid. The crude product was purified by Combiflash silica gel column chromatography using 25% EtOAc in Petroleum ether as an eluant to give 2-(4-fluorophenyl)-6-hydroxy-5-isopropoxy-N-methyl-benzofuran-3-carboxamide as a pale yellow solid. Yield: 1.2 g (44%). $^1$H NMR (400 MHz, CHLOROFORM-d) δ=7.83-7.78 (m, 2H), 7.34 (s, 1H), 7.19-7.13 (m, 2H), 7.09-7.07 (m, 1H), 5.99 (s, 1H), 5.77-5.71 (m, 1H), 4.68 (spt, J=6.1 Hz, 1H), 2.97 (d, J=4.9 Hz, 3H), 1.42-1.38 (m, 6H). LCMS: (ES+) m/z=344.1 (M+H)$^+$. Column-ACQUITY UPLC BEH C18 (50×2.1 mm; 1.7 μm). M phase A: 0.1% TFA in water. M phase B: Acetonitrile. Flow: 0.8 ml/min., Rt min: 0.90, wavelength: 220 nm., and gradient:

| Time | % A | % B |
|---|---|---|
| 0 | 98 | 2 |
| 1.0 | 2 | 98 |
| 1.6 | 2 | 98 |

Preparation of 6-ethoxy-2-(4-fluorophenyl)-5-isopropoxy-N-methyl-benzofuran-3-carboxamide

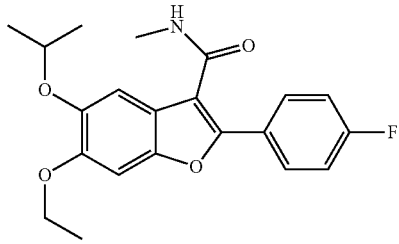 [SMILES: CCOc1cc2oc(-c3ccc(F)cc3)c(C(=O)NC)c2cc1OC(C)C]

To a solution of 2-(4-fluorophenyl)-6-hydroxy-5-isopropoxy-N-methylbenzofuran-3-carboxamide (1.2 g, 3.49 mmol) in DMF (5 mL) was added cesium carbonate (1.708 g, 5.24 mmol) followed by ethyl iodide (0.282 mL, 3.49 mmol). The reaction mixture was then stirred at 25° C. for 12 hours. The reaction mixture was quenched with water and extracted with ethyl acetate (2×100 ml). The combined organic extracts were dried over Na$_2$SO$_4$, filtered and concentrated to give 6-ethoxy-2-(4-fluorophenyl)-5-isopropoxy-N-methyl-benzofuran-3-carboxamide as a pale yellow solid. Yield: 1.1 g (85%). $^1$H NMR (400 MHz, CHLOROFORM-d) δ ppm=7.87 (dd, J=5.4, 8.9 Hz, 2H), 7.34 (s, 1H), 7.15 (t, J=8.8 Hz, 2H), 7.04 (s, 1H), 5.78 (bs, 1H), 4.51-4.45 (m, 1H), 4.11 (q, J=7.0 Hz, 2H), 3.00 (d, J=4.7 Hz, 3H), 1.53-1.49 (m, 3H), 1.36 (d, J=6 Hz, 6H). LCMS: (ES+) m/z=372.4 (M+H)$^+$. Column-ACQUITY UPLC BEH C8 (50×2.1 mm; 1.7 μm). Buffer: 10 mM Ammonium Acetate pH-5 adjusted with HCOOH, M phase A: Buffer:MeCN (95:5). M phase B: Buffer:MeCN (5:95). Flow: 0.8 ml/min., Rt min: 1.11, wavelength: 220 nm., and gradient:

| Time | % A | % B |
|---|---|---|
| 0 | 95 | 5 |
| 1.1 | 5 | 95 |
| 1.7 | 5 | 95 |

Preparation of 6-ethoxy-2-(4-fluorophenyl)-5-hydroxy-N-methylbenzofuran-3-carboxamide

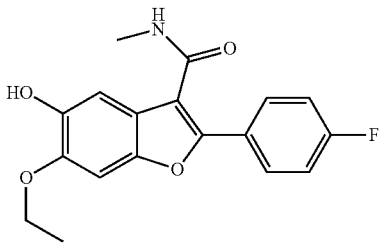 [SMILES: CCOc1cc2oc(-c3ccc(F)cc3)c(C(=O)NC)c2cc1O]

To a solution of 6-ethoxy-2-(4-fluorophenyl)-5-isopropoxy-N-methylbenzofuran-3-carboxamide (1.1 g, 2.96 mmol) in DCM (50 mL) at −78° C. was added boron trichloride (8.89 mL, 8.89 mmol) dropwise. The reaction mixture was slowly allowed to stir at 0° C. for 3 hours, and then quenched with ice-cold water at the same temperature. The mixture was extracted with DCM (2×100 ml). The combined organic extracts were dried over $Na_2SO_4$, filtered and concentrated to give 6-ethoxy-2-(4-fluorophenyl)-5-hydroxy-N-methylbenzofuran-3-carboxamide as a pale yellow solid. Yield: 0.95 g (97%). LCMS: (ES+) m/z=330.1 $(M+H)^+$. Column-ACQUITY UPLC BEH C18 (50×2.1 mm; 1.7 μm). M phase A: 0.1% TFA in water. M phase B: Acetonitrile. Flow: 0.8 ml/min., Rt min: 0.86, wavelength: 220 nm., and gradient:

| Time | % A | % B |
|---|---|---|
| 0 | 98 | 2 |
| 1.0 | 2 | 98 |
| 1.6 | 2 | 98 |

Preparation of 6-ethoxy-2-(4-fluorophenyl)-3-(methylcarbamoyl)benzofuran-5-yl trifluoromethanesulfonate

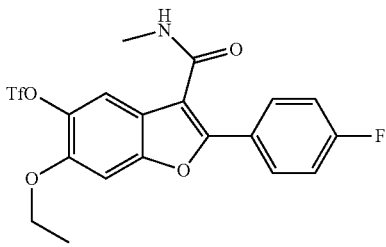 [SMILES: CCOc1cc2oc(-c3ccc(F)cc3)c(C(=O)NC)c2cc1OS(=O)(=O)C(F)(F)F]

To a solution of 6-ethoxy-2-(4-fluorophenyl)-5-hydroxy-N-methylbenzofuran-3-carboxamide (0.95 g, 2.88 mmol) in DMF (12 mL) was added DMAP (1.057 g, 8.65 mmol) and then 1,1,1-trifluoro-N-phenyl-N-(trifluoromethyl)sulfonyl-methanesulfonamide (1.134 g, 3.17 mmol) portionwise. The reaction was stirred at 25° C. for 12 hours. The reaction mixture was quenched with ice-cold water, the solid formed was filtered and dried under suction to give 6-ethoxy-2-(4-fluorophenyl)-3-(methylcarbamoyl)benzofuran-5-yl trifluoromethanesulfonate as a white solid. Yield: 1.2 g (90%). LCMS: (ES+) m/z=462.2 $(M+H)^+$. Column-ACQUITY UPLC BEH C8 (50×2.1 mm; 1.7 μm). M phase A: 5 mM Ammonium Acetate:MeCN (95:5). M phase B: 5 mM Ammonium Acetate:MeCN (5:95). Flow: 0.8 ml/m., Rt min: 1.18, wavelength: 220 nm., and gradient:

| Time | % A | % B |
|---|---|---|
| 0 | 95 | 5 |
| 1.1 | 5 | 95 |
| 1.7 | 5 | 95 |

Preparation of methyl 5-(6-ethoxy-2-(4-fluorophenyl)-3-(methylcarbamoyl)benzofuran-5-yl)-2-(methoxy-$d_3$)benzoate

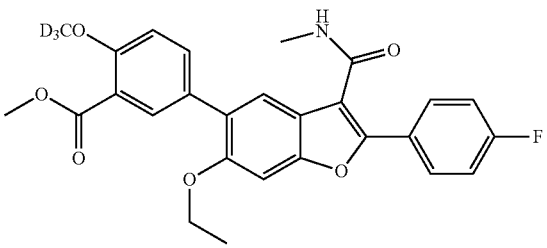

A mixture of 6-ethoxy-2-(4-fluorophenyl)-3-(methylcarbamoyl)benzofuran-5-yl trifluoromethanesulfonate (0.15 g, 0.325 mmol), methyl 2-(methoxy-$d_3$)-5-(4,4,5,5-tetramethyl-1,3,2-dioxaborolan-2-yl)benzoate (0.192 g, 0.650 mmol) (prepared from methyl 5-bromo-2-hydroxybenzoate in two steps using the conditions: (i) NaH, $CD_3I$, DMF, 0° C.; (ii) bis(pinacolato)diboron, KOAc, $Pd(dppf)Cl_2$, dioxane, 90° C.) and cesium carbonate (0.265 g, 0.813 mmol) in 1,4-dioxane (15 mL)/water (0.3 mL) was degasified for 5 min. Tetrakis(triphenylphosphine)palladium(0) (0.019 g, 0.016 mmol) was added to the mixture, which was then degassed again for 5 min. The resulting reaction mixture was stirred at 110° C. for 2 hrs. The reaction mixture was filtered through a celite bed and the bed washed with EtOAc (50 ml). The organic layer was dried over $Na_2SO_4$, filtered and concentrated. The crude product was purified by Combiflash silica gel column chromatography using 50% EtOAc in Petroleum ether as an eluant to give methyl 5-(6-ethoxy-2-(4-fluorophenyl)-3-(methylcarbamoyl)benzofuran-5-yl)-2-(methoxy-$d_3$)benzoate as a white solid product. Yield: 0.155 g (99%). $^1$H NMR (300 MHz, CHLOROFORM-d) δ ppm=8.03 (d, J=2.3 Hz, 1H), 7.93 (dd, J=5.2, 8.8 Hz, 2H), 7.71-7.66 (m, 2H), 7.18 (t, J=8.6 Hz, 2H), 7.10 (s, 1H), 7.02 (d, J=8.6 Hz, 1H), 5.89-5.82 (m, 1H), 4.15-4.06 (m, 2H), 3.91 (s, 3H), 3.01 (d, J=5.0 Hz, 3H), 1.39 (t, J=6.9 Hz, 3H). LCMS: (ES+) m/z=481.3 $(M+H)^+$. Column-ACQUITY UPLC BEH C8 (50×2.1 mm; 1.7 μm). M phase A: 5 mM Ammonium Acetate:MeCN (95:5). M phase B: 5 mM Ammonium Acetate:MeCN (5:95). Flow: 0.8 ml/min., Rt min: 1.13, wavelength: 220 nm., and gradient:

| Time | % A | % B |
|---|---|---|
| 0 | 95 | 5 |
| 1.1 | 5 | 95 |
| 1.7 | 5 | 95 |

Preparation of 5-(6-ethoxy-2-(4-fluorophenyl)-3-(methylcarbamoyl)benzofuran-5-yl)-2-(methoxy-d$_3$) benzoic acid

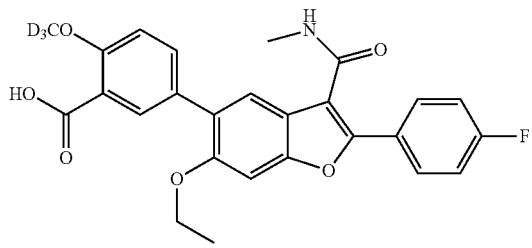

To a solution of methyl 5-(6-ethoxy-2-(4-fluorophenyl)-3-(methylcarbamoyl)benzofuran-5-yl)-2-(methoxy-d$_3$)benzoate (0.155 g, 0.323 mmol) in THF (2 mL) and methanol (3 mL) was added NaOH (0.013 g, 0.323 mmol) and water (1 mL). The resulting reaction mixture was stirred at 25° C. for 12 hours. The volatiles were removed under vacuum, and the residue acidified to pH=2. The solid was filtered and dried to obtain 5-(6-ethoxy-2-(4-fluorophenyl)-3-(methylcarbamoyl)benzofuran-5-yl)-2-(methoxy-d$_3$)benzoic acid as a yellow solid. Yield: 130 mg (86%). $^1$H NMR (300 MHz, DMSO-d$_6$) δ ppm=8.43 (d, J=4.6 Hz, 2H), 7.96 (dd, J=5.5, 8.8 Hz, 2H), 7.64 (d, J=8.5 Hz, 1H), 7.47-7.33 (m, 4H), 7.15 (d, J=8.6 Hz, 1H), 4.13 (q, J=7.1 Hz, 2H), 2.82 (d, J=4.5 Hz, 3H), 1.30 (t, J=6.9 Hz, 3H). LCMS: (ES+) m/z=467.04 (M+H)$^+$. Column-ACQUITY UPLC BEH C8 (50×2.1 mm; 1.7 μm). M phase A: 5 mM Ammonium Acetate: MeCN (95:5). M phase B: 5 mM Ammonium Acetate:MeCN (5:95). Flow: 0.8 ml/min., Rt min: 0.81, wavelength: 220 nm., and gradient:

| Time | % A | % B |
|---|---|---|
| 0 | 95 | 5 |
| 1.1 | 5 | 95 |
| 1.7 | 5 | 95 |

Preparation of methyl 5-(2-(4-fluorophenyl)-3-(methylcarbamoyl)-6-(2,2,2-trifluoroethoxy)benzofuran-5-yl)-2-methoxynicotinate

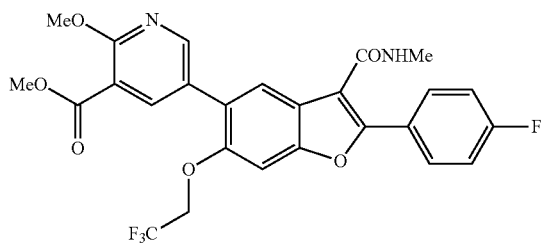

A stirred solution of 2-(4-fluorophenyl)-3-(methylcarbamoyl)-6-(2,2,2-trifluoroethoxy)benzofuran-5-yl trifluoromethanesulfonate (100 mg, 0.194 mmol), methyl 2-methoxy-5-(4,4,5,5-tetramethyl-1,3,2-dioxaborolan-2-yl) nicotinate (85 mg, 0.291 mmol) and Cs$_2$CO$_3$ (190 mg, 0.582 mmol) in dioxan (3 mL) in a microwave vessel was purged with nitrogen for 5 min. Water (0.2 ml) and (PPh$_3$)$_4$Pd(0) (22.43 mg, 0.019 mmol) were added to the mixture, which was then heated in microwave at 100° C. for 2 hr. After completion of the reaction, the solvent was evaporated and the crude compound was purified by Combiflash using a 12 g silica gel column with EtOAc/n-hexane (30:70) as an eluent to afford methyl 5-(2-(4-fluorophenyl)-3-(methylcarbamoyl)-6-(2,2,2-trifluoroethoxy)benzofuran-5-yl)-2-methoxynicotinate. Yield: 70 mg (68%). LCMS: Column-ACQUITY UPLC BEH C18 (50×2.1 mm; 1.7 μm), M (=Mobile) phase A: 0.1% TFA in water, M phase B: Acetonitrile, Flow: 0.8 ml/min. RT min: 1.00, wavelength: 220 nm.

| Time | % A | % B |
|---|---|---|
| 0.0 | 98 | 2 |
| 1.0 | 2 | 98 |
| 1.6 | 2 | 98 |

Preparation of 5-(2-(4-fluorophenyl)-3-(methylcarbamoyl)-6-(2,2,2-trifluoroethoxy) benzofuran-5-yl)-2-methoxynicotinic acid

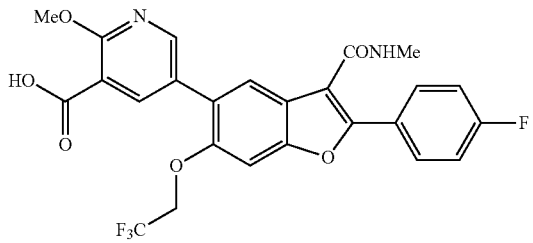

To a stirred solution of methyl 5-(2-(4-fluorophenyl)-3-(methylcarbamoyl)-6-(2,2,2-trifluoroethoxy)benzofuran-5-yl)-2-methoxynicotinate (70 mg, 0.131 mmol) in methanol (5 ml)/water (2 ml) was added NaOH (21.04 mg, 0.526 mmol). The mixture was stirred at 50° C. for 30 min. After completion of the reaction, the organic solvent was evaporated, and the pH of the mixture was adjusted to 4 with acetic acid. The mixture was extracted with ethyl acetate (15 ml×2). The combined organic extracts were dried over Na$_2$SO$_4$, filtered, and evaporated to afford 5-(2-(4-fluorophenyl)-3-(methylcarbamoyl)-6-(2,2,2-trifluoroethoxy)benzofuran-5-yl)-2-methoxynicotinic acid. Yield: 50 mg (74%). LCMS: (ES+) m/z=519.1 (M+H)$^+$, Column-ACQUITY UPLC BEH C18 (50×2.1 mm; 1.7 μm), M phase A: 0.1% TFA in water, M phase B: Acetonitrile, Flow: 0.8 ml/min, Rt min: 0.93, wavelength: 220 nm.

| Time | % A | % B |
|---|---|---|
| 0.0 | 98 | 2 |
| 1.0 | 2 | 98 |
| 1.6 | 2 | 98 |

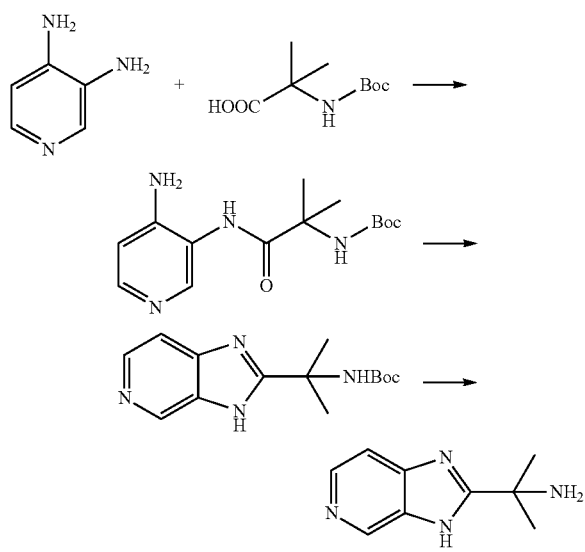

Preparation of tert-butyl (1-((4-aminopyridin-3-yl)amino)-2-methyl-1-oxopropan-2-yl)carbamate

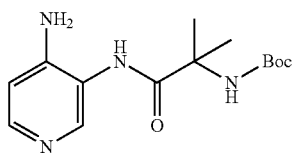 [SMILES: CC(C)(C)OC(=O)NC(C)(C)C(=O)Nc1cnccc1N]

To a stirred solution of pyridine-3,4-diamine (1.0 g, 9.16 mmol) and 2-((tert-butoxycarbonyl)amino)-2-methylpropanoic acid (2.23 g, 11.00 mmol) in DMF (50 mL) was added 2-(1H-benzo[d][1,2,3]triazol-1-yl)-1,1,3,3-tetramethylisouronium tetrafluoroborate (TBTU) (3.53 g, 11.00 mmol) and diisopropylethylamine (DIPEA) (3.55 g, 27.5 mmol). The resulting reaction mixture was stirred at an ambient temperature for overnight. After completion of the reaction, the reaction was quenched with water and extracted with DCM (100 ml). The organic layer was washed with brine, water and concentrated to give tert-butyl (1-((4-aminopyridin-3-yl)amino)-2-methyl-1-oxopropan-2-yl)carbamate as a liquid. Yield: 1.5 g (60%). $^1$H NMR (400 MHz, DMSO-$d_6$) δ ppm 9.08 (s, 1H), 8.00 (s, 1H), 7.73 (d, J=4.8 Hz, 1H), 7.15 (bs, 2H), 5.01 (bs, 2H), 1.38 (s, 15H). LCMS: (ES+) m/z=295.4 (M+H)$^+$, Column-ACQUITY UPLC BEH C8 (50×2.1 mm; 1.7 μm), M phase A: 5 mM Ammonium Acetate: MeCN (95:5), M phase B: 5 mM Ammonium Acetate: MeCN (5:95), Flow: 0.8 ml/min, Rt min: 0.64, wavelength: 220 nm.

| Time | % A | % B |
|------|-----|-----|
| 0.0  | 95  | 5   |
| 1.1  | 5   | 95  |
| 1.7  | 5   | 95  |

Preparation of tert-butyl (2-(3H-imidazo[4,5-c]pyridin-2-yl)propan-2-yl)carbamate

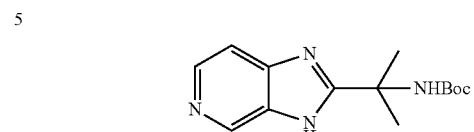

A solution of tert-butyl (1-((4-aminopyridin-3-yl)amino)-2-methyl-1-oxopropan-2-yl)carbamate (0.1 g, 0.340 mmol) in AcOH (0.051 g, 0.849 mmol) and DMF (1 mL) was stirred at 65° C. for overnight. After completion of the reaction, heating was stopped. The reaction mixture was diluted with DCM and basified with 10% NaOH solution, and extracted with 10% MeOH:CHCl$_3$. The organic layer was dried over Na$_2$SO$_4$, filtered, and evaporated to give tert-butyl (2-(3H-imidazo[4,5-c]pyridin-2-yl)propan-2-yl)carbamate as a pale yellow solid. Yield: 0.1 g. LCMS: (ES+) m/z=277.2 (M+H)$^+$, Column-Ascentis Express C18 (50×2.1 mm-2.7 μm), M phase A: 2% MeCN-98% H2O-10 mM NH$_4$COOH, M phase B: 98% MeCN-2% H2O-10 mM NH$_4$COOH, Flow=1 mL/min, Time (min.): Rt min: 1.71, wavelength: 220 nm.

| Time | % B   |
|------|-------|
| 0.0  | 0.0   |
| 1.7  | 100.0 |
| 3.0  | 100.0 |
| 3.0  | 0.0   |

Preparation of 2-(3H-imidazo[4,5-c]pyridin-2-yl)propan-2-amine

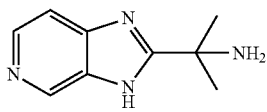

To a stirred solution of tert-butyl (2-(3H-imidazo[4,5-c]pyridin-2-yl)propan-2-yl)carbamate (0.1 g, 0.340 mmol) in MeOH (2 mL) was added a solution of 4M HCl in dioxan (2 mL, 8.00 mmol). The mixture was stirred at room temperature for overnight. After completion of the reaction, the solvent was evaporated and the crude product triturated in n-hexane to afford 2-(3H-imidazo[4,5-c]pyridin-2-yl)propan-2-amine hydrochloride salt as a pale yellow colored solid (the equivalent of HCl was not determined). Yield: 50 mg. $^1$H NMR (400 MHz, DMSO-$d_6$) δ ppm 9.54 (s, 1H), 9.08 (s, 2H), 8.63 (d, J=6.4 Hz, 1H), 8.50 (bs, 1H), 8.18 (d, J=6.4 Hz, 1H), 1.82 (s, 6H). LCMS: (ES+) m/z=177 (M+H)$^+$, Column-ACQUITY UPLC BEH C8 (50×2.1 mm; 1.7 μm), M phase A: 5 mM Ammonium Acetate: MeCN (95:5), M phase B: 5 mM Ammonium Acetate:MeCN (5:95), Flow: 0.8 ml/min, Rt min: 1.79, wavelength: 220 nm.

| Time | % A | % B |
| --- | --- | --- |
| 0.0 | 95 | 5 |
| 1.1 | 5 | 95 |
| 1.7 | 5 | 95 |

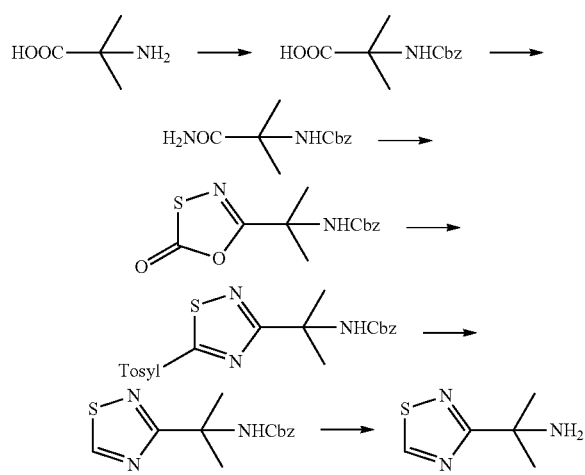

Preparation of 2-(((benzyloxy)carbonyl)amino)-2-methylpropanoic acid

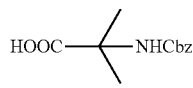 [SMILES: CC(C)(NC(=O)OCc1ccccc1)C(=O)O]

To a stirred solution of 2-amino-2-methylpropanoic acid, HCl (2.0 g, 14.33 mmol) in water (30 ml) at 10° C. was added Na$_2$CO$_3$ (4.56 g, 43.0 mmol) followed by a solution of benzyl carbonochloridate (2.037 mL, 14.33 mmol) in dioxan (20 ml). The resulting white suspension was stirred at room temperature for overnight. After completion of the reaction, the mixture was extracted with diethyl ether (25 ml×2). The aqueous layer was acidified using 1 N HCl and the mixture extracted with ethyl acetate (50 ml×2). The combined organic extracts were dried over Na$_2$SO$_4$, filtered and evaporated to afford 2-(((benzyloxy)carbonyl)amino)-2-methylpropanoic acid. Yield: 3.0 g (88%) LCMS: (ES−) m/z=236 (M−H)$^−$, Column-Ascentis Express C18 (50×2.1 mm-2.7 μm), M phase A: 0.1% HCOOH in water, M phase B: MeCN, Flow=1 mL/min, Rt=1.80 min. Wavelength: 220 nm.

| Time | % A | % B |
| --- | --- | --- |
| 0.0 | 100 | 0 |
| 1.7 | 0 | 100 |
| 3.2 | 0 | 100 |

Preparation of benzyl (1-amino-2-methyl-1-oxopropan-2-yl)carbamate

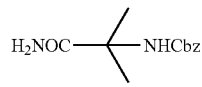

To a stirred solution of 2-(((benzyloxy)carbonyl)amino)-2-methylpropanoic acid (3.0 g, 12.64 mmol) in acetonitrile (30 ml) at 10° C. was added pyridine (2.023 g, 25.3 mmol) followed by Boc anhydride (2.76 g, 12.64 mmol) and NH$_4$CO$_3$ (4.24 g, 63.2 mmol). The resulting white suspension was stirred at room temperature for overnight. After completion of the reaction, the solvent was evaporated, and the residue was added ice-cold water while stirring. The white solid obtained was dried under vacuum to afford benzyl (1-amino-2-methyl-1-oxopropan-2-yl)carbamate. Yield: 2.0 g (67%). LCMS: (ES+) m/z=237 (M+H)$^+$, Column-Ascentis Express C18 (50×2.1 mm-2.7 μm), M phase A: 5% MeCN-95% H$_2$O-10 mM NH$_4$OOCCH$_3$, M phase B: 95% MeCN-5% H$_2$O-10 mM NH$_4$OOCCH$_3$, Flow=1 mL/MINmin, Time (min.): Rt min: 1.60, wavelength: 220 nm.

| Time | % B |
| --- | --- |
| 0.0 | 0.0 |
| 1.7 | 100.0 |
| 3.4 | 100.0 |

Preparation of benzyl (2-(2-oxo-1,3,4-oxathiazol-5-yl)propan-2-yl)carbamate

To a stirred solution of benzyl (1-amino-2-methyl-1-oxopropan-2-yl)carbamate (1.0 g, 4.23 mmol) in toulene (20 ml) was added carbonochloridic hypochlorous thioanhydride (1.109 g, 8.46 mmol). The resulting clear solution was stirred at 80° C. for 3 hr. After completion of the reaction, the solvent was evaporated to afford benzyl (2-(2-oxo-1,3,4-oxathiazol-5-yl)propan-2-yl)carbamate as a brown colored solid. Yield: 1.2 g. LCMS: (ES+) m/z=295 (M+H)$^+$, Column-Zorbax SB AQ (4.6×50 mm; 3.5 um), Buffer: 0.1% HCOOH in water, Mobile phase A: Buffer:MeCN (98:2), Mobile phase B: Buffer:MeCN (2:98), Flow: 1.0 ml/min. Rt: 3.19 min, wavelength: 220 nm.

| Time | % A | % B |
| --- | --- | --- |
| 0.0 | 100 | 0.0 |
| 2.7 | 0.0 | 100.0 |
| 4.0 | 0.0 | 100.0 |

Preparation of benzyl (2-(5-tosyl-1,2,4-thiadiazol-3-yl)propan-2-yl)carbamate

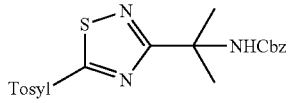

To a stirred solution of benzyl (2-(2-oxo-1,3,4-oxathiazol-5-yl)propan-2-yl)carbamate (1.2 g, 4.08 mmol) in 1,2 dichlorobenzene (10 mL) was added tosyl cyanide (1.478 g, 8.15 mmol). The reaction mixture was stirred at 160° C. for 3 hr. After completion of the reaction, heating was stopped and the solvent evaporated. The crude compound was purified by Combiflash using a silica gel column with 15-20% EtOAc/n-hexane as a mobile phase to afford benzyl (2-(5-tosyl-1,2,4-thiadiazol-3-yl)propan-2-yl)carbamate. Yield: 600 mg (34%). LCMS: (ES+) m/z=432 (M+H)$^+$, Column-Zorbax SB AQ (4.6×50 mm; 3.5 um), Buffer: 0.1% HCOOH in water, Mobile phase A: Buffer:MeCN (98:2), Mobile phase B: Buffer:MeCN (2:98), Flow: 1.0 ml/min., Rt: 3.53 min, wavelength: 220 nm.

| Time | % A | % B |
| --- | --- | --- |
| 0.0 | 100 | 0.0 |
| 2.7 | 0.0 | 100.0 |
| 4.0 | 0.0 | 100.0 |

Preparation of benzyl (2-(1,2,4-thiadiazol-3-yl)propan-2-yl)carbamate

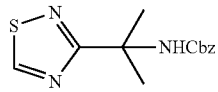 [SMILES: CC(C)(NC(=O)OCc1ccccc1)c1ncsn1]

To a stirred solution of benzyl (2-(5-tosyl-1,2,4-thiadiazol-3-yl)propan-2-yl)carbamate (300 mg, 0.695 mmol) in ethanol (10 mL) was added NaBH$_4$ (52.8 mg, 1.390 mmol). The resulting solution was stirred at room temperature for 2 hr. After completion of the reaction, the solvent was evaporated and the residue quenched with ice-cold water. The white precipitates were filtered and dried to afford benzyl (2-(1,2,4-thiadiazol-3-yl)propan-2-yl)carbamate. Yield: 200 mg. $^1$H NMR (400 MHz, DMSO-d$_6$) δ ppm: 10.15 (s, 1H), 7.85 (bs, 1H). 7.30 (m, 5H), 5.14 (s, 2H), 1.61 (s, 6H). LCMS: (ES+) m/z=278.4 (M+H)$^+$, Column-ACQUITY UPLC BEH C8 (50×2.1 mm; 1.7 μm) M phase A: 5 mM Ammonium Acetate:MeCN (95:5), M phase B: 5 mM Ammonium Acetate:MeCN (5:95), Flow: 0.8 ml/min, Rt min: 0.83, wavelength: 220 nm.

| Time | % A | % B |
| --- | --- | --- |
| 0.0 | 95 | 5 |
| 1.1 | 5 | 95 |
| 1.7 | 5 | 95 |

Preparation of 2-(1,2,4-thiadiazol-3-yl)propan-2-amine

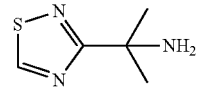

A mixture of benzyl (2-(1,2,4-thiadiazol-3-yl)propan-2-yl)carbamate (150 mg, 0.541 mmol) and 33% HBr in acetic acid (2 ml, 0.541 mmol) was stirred at room temperature for 1 hr. After completion of the reaction, the volatiles were evaporated and the residue triturated with n-hexane to afford 2-(1,2,4-thiadiazol-3-yl)propan-2-amine hydrobromide salt as a pale yellow solid. Yield: 100 mg. $^1$H NMR (400 MHz, DMSO-d$_6$) δ ppm 10.22 (s, 1H), 1.81 (s, 6H). LCMS: (ES+) m/z=144 (M+H)$^+$, Column-Ascentis Express C18 (50×2.1 mm-2.7 μm), M phase A: 2% MeCN-98% H$_2$O-10 mM NH$_4$COOH, M phase B: 98% MeCN-2% H$_2$O-10 mM NH$_4$COOH, Flow=1 mL/min, Time (min.): Rt min: 2.15, wavelength: 220 nm.

| Time | % B |
| --- | --- |
| 0.0 | 0.0 |
| 1.7 | 100.0 |
| 3.4 | 100.0 |

Example 1

2-(4-Fluorophenyl)-N-methyl-5-(3-((1-(pyrimidin-2-yl)cyclopropyl)carbamoyl)phenyl)-6-(2,2,2-trifluoroethoxy)benzofuran-3-carboxamide

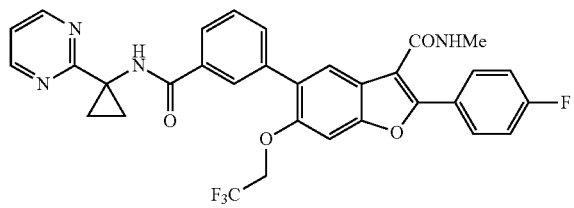

To a stirred solution of 3-(2-(4-fluorophenyl)-3-(methylcarbamoyl)-6-(2,2,2-trifluoroethoxy)benzofuran-5-yl)benzoic acid (25 mg, 0.051 mmol) and 1-(pyrimidin-2-yl)cyclopropanamine hydrochloride (9.68 mg, 0.056 mmol) in DMF (2.5 mL) at 0° C. under a nitrogen atmosphere was added triethylamine (TEA) (0.036 mL, 0.256 mmol) followed by (benzotriazol-1-yloxy)tris(dimethylamino)phosphonium hexafluorophosphate (BOP) (34.0 mg, 0.077 mmol). The reaction mixture was allowed to stir at ambient temperature for 16 hr. After completion of the reaction, it was diluted with water, extracted with EtOAc (20 ml×3). The combined organic layers were washed with saturated brine solution, dried over Na$_2$SO$_4$ and concentrated under reduced pressure. The crude solid product obtained was purified by preparative (Prep) HPLC to afford 2-(4-fluorophenyl)-N-methyl-5-(3-((1-(pyrimidin-2-yl)cyclopropyl)carbamoyl)phenyl)-6-(2,2,2-tri-fluoroethoxy)benzofuran-3-carboxamide as a white solid. Yield: 20.56 mg, (66.32%).

PREPARATIVE HPLC conditions: Column: SUNFIRE C-18 (19*150) mm*5 u, Mobile Phase: 10 mM Ammonium acetate pH-4.5 with AcOH (Mobile phase A): MeCN (acetonitrile) (Mobile phase B), Flow: 16 ml/min, Rt (retention time): 16.23 min. $^1$H NMR (400 MHz, CHLOROFORM-d) δ ppm=8.60 (d, J=4.8 Hz, 2 H), 8.01 (t, J=1.5 Hz, 1H), 7.95-7.87 (m, 3H), 7.82 (s, 1H), 7.70 (td, J=1.3, 7.9 Hz, 1H), 7.55-7.49 (m, 1H), 7.22-7.15 (m, 4H), 7.06 (t, J=4.9 Hz, 1H), 5.87 (bs, 1H), 4.33 (q, J=8.1 Hz, 2H), 3.01 (d, J=4.9 Hz, 3H), 1.85-1.80 (m, 2H), 1.61-1.59 (m, 2H) (bs=broad singlet). $^{19}$F NMR (376.6 MHz, CHLOROFORM-d) δ: −73.49, −109.67. LCMS: (ES+) m/z=605.2 (M+H)$^+$, Column-Acentis Express C18 (50×2.1 mm; 2.7 um), Buffer: 10 mM Ammonium Formate in Water pH 4.5, Mobile phase A: Buffer:MeCN (98:2), Mobile phase B: Buffer:MeCN (2:98), Flow: Rt: 2.34 min, wavelength: 254 nm. HPLC Method: SUNFIRE (150×4.6 mm) 3.5 micron, Buffer: 0.05% TFA in water pH 2.5, Mobile Phase A: Buffer:MeCN (95:5), Mobile Phase B: MeCN: Buffer (95:5), Flow: 1.0 ml/min, Wavelength: 254 nm, Rt: 11.01 min, Wavelength: 220 nm, Rt: 11.01 min. HPLC Method:)(Bridge Phenyl (150×4.6 mm) 3.5 micron SC/749, Buffer: 0.05% TFA in water pH 2.5, Mobile Phase A: Buffer:MeCN (95:5), Mobile Phase B: Buffer:MeCN (5:95), Flow: 1.0 ml/min, Wavelength: 254 nm, Rt: 9.77 min, Wavelength: 220 nm, Rt: 9.77 min.

Preparative HPLC Method

Flow: 16 ml/min, Gradient: Time (T, min)/% B: 0/50, 8/80, 15/100

| LCMS | | |
|---|---|---|
| Time | % A | % B |
| 0.0 | 100 | 0 |
| 1.5 | 0 | 100 |
| 3.2 | 0 | 100 |

HPLC Method: SUNFIRE C18 (150×4.6 mm) 3.5 micron

| Time | B % |
|---|---|
| 0 | 10 |
| 12 | 100 |
| 15 | 100 |

HPLC Method:)(Bridge Phenyl (150×4.6 mm) 3.5 micron SC/749

| Time | B % |
|---|---|
| 0 | 10 |
| 12 | 100 |
| 15 | 100 |

Example 2

2-(4-Fluorophenyl)-5-(4-methoxy-3-((1-(pyrimidin-2-yl)cyclopropyl)carbamoyl)phenyl)-N-methyl-6-(2,2,2-trifluoroethoxy)benzofuran-3-carboxamide

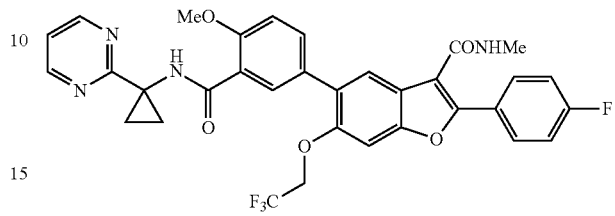

To a stirred solution of 5-(2-(4-fluorophenyl)-3-(methylcarbamoyl)-6-(2,2,2-trifluoroethoxy) benzofuran-5-yl)-2-methoxybenzoic acid (30 mg, 0.058 mmol) and 1-(pyrimidin-2-yl) cyclopropanamine hydrochloride (10.95 mg, 0.064 mmol) in DMF (3.0 mL) at 0° C. under a nitrogen atmosphere was added TEA (0.040 mL, 0.290 mmol) followed by BOP (38.5 mg, 0.087 mmol). The reaction mixture was allowed to stir at ambient temperature for 16 hr. After completion of the reaction, the mixture was diluted with water, extracted with EtOAc (20 ml×3). The combined organic layers were washed with saturated brine solution, dried over Na$_2$SO$_4$, filtered and concentrated under reduced pressure. The crude solid product obtained was purified by Prep HPLC to afford 2-(4-fluorophenyl)-5-(4-methoxy-3-((1-(pyrimidin-2-yl)cyclopropyl) carbamoyl)phenyl)-N-methyl-6-(2,2,2-trifluoroethoxy)benzofuran-3-carboxamide as a white solid. Yield: 24 mg, (64.8%). PREPARATIVE HPLC conditions: Column: chemsil (19*250) mm*10 um, Mobile Phase: 10 mM Ammonium acetate pH-4.5 with AcOH (A): MeCN (B), Flow: 16 ml/min, Rt: 13.69 min. $^1$H NMR (400 MHz, CHLOROFORM-d) δ ppm=8.75 (s, 1H), 8.62 (d, J=4.9 Hz, 2H), 8.35 (d, J=2.4 Hz, 1H), 7.98-7.94 (m, 2H), 7.71 (s, 1H), 7.68 (dd, J=2.5, 8.6 Hz, 1H), 7.19-7.14 (m, 3H), 7.08-7.02 (m, 2H), 5.90 (bs, 1H), 4.27 (q, J=8.2 Hz, 2H), 4.07 (s, 3H), 3.02 (d, J=4.9 Hz, 3H), 1.86-1.81 (m, 2H), 1.55-1.53 (m, 2H). $^{19}$F NMR (376.6 MHz, CHLOROFORM-d) δ: −73.60, −110.19. LCMS: (ES+) m/z=635.2 (M+H)$^+$, Column-Acentis Express C18 (50×2.1 mm; 2.7 um), Buffer: 10 mM Ammonium Formate in Water pH 4.5, Mobile phase A: Buffer:MeCN (98:2), Mobile phase B: Buffer:MeCN (2:98), Flow: 1.0 ml/min. Rt: 2.243 min, wavelength: 220 nm. HPLC Method: SUNFIRE (150×4.6 mm) 3.5 micron, Buffer: 0.05% TFA in water pH 2.5, Mobile Phase A: Buffer:MeCN (95:5), Mobile Phase B: MeCN: Buffer (95:5), Flow: 1.2 ml/min, Wavelength: 254 nm, Rt: 11.04 min, Wavelength: 220 nm, Rt: 11.04 min. HPLC Method:)(Bridge Phenyl (150×4.6 mm) 3.5 micron SC/749, Buffer: 0.05% TFA in water pH 2.5, Mobile Phase A: Buffer:MeCN (95:5), Mobile Phase B: Buffer:MeCN (5:95), Flow: 1.0 ml/min, Wavelength: 254 nm, Rt: 17.06 min, Wavelength: 220 nm, Rt: 17.06 min.

Preparative HPLC Method

Flow: 16 ml/min., Gradient: Time (min)/% B: 0/30, 10/60

| LCMS | | |
|---|---|---|
| Time | % A | % B |
| 0.0 | 100 | 0 |
| 1.7 | 0 | 100 |
| 3.2 | 0 | 100 |

HPLC Method: SUNFIRE C18 (150×4.6 mm) 3.5 micron

| Time | B % |
|---|---|
| 0 | 40 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 3

5-(4-Fluoro-3-((1-(pyrimidin-2-yl)cyclopropyl)carbamoyl)phenyl)-2-(4-fluorophenyl)-N-methyl-6-(2,2,2-trifluoroethoxy)benzofuran-3-carboxamide

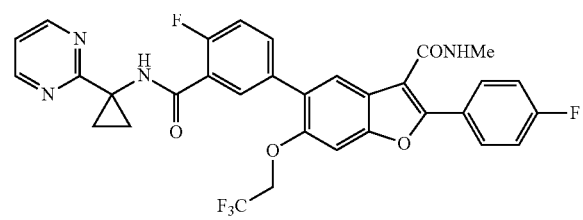

To a stirred solution of 2-fluoro-5-(2-(4-fluorophenyl)-3-(methylcarbamoyl)-6-(2,2,2-trifluoroethoxy)benzofuran-5-yl)benzoic acid (25 mg, 0.049 mmol) and 1-(pyrimidin-2-yl)cyclopropanamine hydrochloride (9.34 mg, 0.054 mmol) in DMF (3.0 mL) at 0° C. under a nitrogen atmosphere was added TEA (0.034 mL, 0.247 mmol) followed by BOP (32.8 mg, 0.074 mmol). The reaction mixture was allowed to stir at ambient temperature for 16 hr. After completion of the reaction, the mixture was diluted with water and extracted with EtOAc (20 ml×3). The combined organic extracts were washed with saturated brine solution, dried over Na$_2$SO$_4$, filtered and concentrated under reduced pressure. The crude solid product obtained was purified by Prep. HPLC to afford 5-(4-fluoro-3-((1-(pyrimidin-2-yl)cyclopropyl)carbamoyl)phenyl)-2-(4-fluorophenyl)-N-methyl-6-(2,2,2-trifluoroethoxy)benzofuran-3-carboxamide as a white solid. Yield: 14.51 mg, (47.12%). PREPARATIVE HPLC: Column: chemsil (19*250) mm*10 um, Mobile Phase: 10 mM Ammonium acetate pH-4.5 with AcOH (A): MeOH (B), Flow: 16 ml/min, Rt: 12.21 min. $^1$H NMR (400 MHz, CHLOROFORM-d) δ ppm=8.62 (d, J=4.9 Hz, 2H), 8.23 (dd, J=2.4, 7.5 Hz, 1H), 7.96-7.92 (m, 2H), 7.75 (s, 1H), 7.70-7.64 (m, 2H), 7.21-7.14 (m, 4H), 7.06 (t, J=4.8 Hz, 1H), 5.85 (b s, 1H), 4.32 (q, J=8.1 Hz, 2H), 3.02 (d, J=4.9 Hz, 3H), 1.87-1.83 (m, 2H), 1.61-1.57 (m, 2H). $^{19}$F NMR (376.6 MHz, CHLOROFORM-d) δ: −73.59, −109.84, −114.76. LCMS: (ES+) m/z=623.1 (M+H)$^+$, Column-Acentis Express C18 (50×2.1 mm; 2.7 um), Buffer: 10 mM Ammonium Formate in Water pH 4.5, Mobile phase A: Buffer:MeCN (98:2), Mobile phase B: Buffer:MeCN (2:98), Flow: 1.0 ml/min. Rt: 2.23 min, wavelength: 220 nm. HPLC Method: SUNFIRE (150×4.6 mm) 3.5 micron, Buffer: 0.05% TFA in water, Mobile Phase A: Buffer:MeCN (95:5), Mobile Phase B: MeCN: Buffer (95:5), Flow: 1.0 ml/min, Wavelength: 254 nm, Rt: 18.08 min, Wavelength: 220 nm, Rt: 18.08 min. HPLC Method:)(Bridge Phenyl (150×4.6 mm) 3.5 micron SC/749, Buffer: 0.05% TFA in water, Mobile Phase A: Buffer:MeCN (95:5), Mobile Phase B: Buffer:MeCN (5:95), Flow: 1.0 ml/min, Wavelength: 254 nm, Rt: 10.51 min, Wavelength: 220 nm, Rt: 10.51 min.

Preparative HPLC Method

Flow: 16 ml/min., Gradient: T/% B: 0/50, 8/80, 13/80

| LCMS | | |
|---|---|---|
| Time | % A | % B |
| 0.0 | 100 | 0 |
| 1.7 | 0 | 100 |
| 3.2 | 0 | 100 |

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 12 | 100 |
| 15 | 100 |

Example 4

5-(3-(Bicyclo[1.1.1]pentan-1-ylcarbamoyl)-4-fluorophenyl)-2-(4-fluoro phenyl)-N-methyl-6-(2,2,2-trifluoroethoxy)benzofuran-3-carboxamide

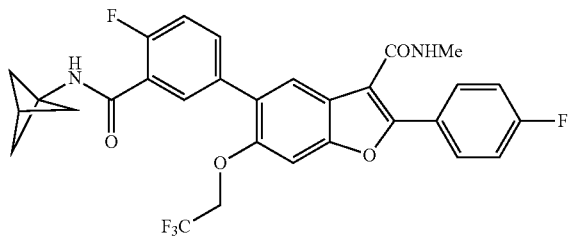

To a stirred solution of 2-fluoro-5-(2-(4-fluorophenyl)-3-(methylcarbamoyl)-6-(2,2,2-trifluoroethoxy)benzofuran-5-yl)benzoic acid (35 mg, 0.069 mmol) and bicyclo[1.1.1]pentan-1-amine hydrochloride (8.28 mg, 0.069 mmol) in DMF (3.0 mL) at room temperature under a $N_2$ atmosphere was added diisopropylethylamine (DIPEA) (0.060 mL, 0.346 mmol) (0.132 mL, 0.755 mmol). The mixture was cooled to 0° C., and 2-(7-aza-1H-benzotriazole-1-yl)-1,1,3,3-tetramethyluronium hexafluorophosphate (HATU) (39.5 mg, 0.104 mmol) was added to the mixture. The reaction mixture was allowed to stir at ambient temperature for 16 hr. After completion of the reaction, the mixture was diluted with water and extracted with EtOAc (25 ml×3). The combined organic layers were washed with saturated brine solution, dried over $Na_2SO_4$ and concentrated under reduced pressure. The crude solid product was purified by Prep HPLC to obtained 5-(3-(bicyclo[1.1.1]pentan-1-ylcarbamoyl)-4-fluorophenyl)-2-(4-fluorophenyl)-N-methyl-6-(2,2,2-trifluoroethoxy)benzo-furan-3-carboxamide as a white solid. Yield: 10.00 mg, (25.1%). PREPARATIVE HPLC: Column: chemsil (19*250) mm*10 um, Mobile Phase: 10 mM Ammonium acetate pH-4.5 with AcOH (A): MeOH (B), Flow: 16 ml/min, Rt: 15.69 min. $^1$H NMR (400 MHz, CHLOROFORM-d) δ ppm=8.17 (dd, J=2.4, 7.6 Hz, 1H), 7.97-7.91 (m, 2H), 7.73 (s, 1H), 7.65 (ddd, J=2.5, 4.9, 8.6 Hz, 1H), 7.21-7.13 (m, 4H), 7.07 (d, J=12.6 Hz, 1H), 5.84 (b s, 1H), 4.31 (q, J=8.1 Hz, 2H), 3.03 (s, 3H), 2.53 (s, 1H), 2.23 (s, 6H). $^{19}$F NMR (376.6 MHz, CHLOROFORM-d) δ ppm: −73.64, −109.80, −115.72. LCMS: (ES+) m/z=571.0 (M+H)$^+$, Column-Acentis Express C18 (50×2.1 mm; 2.7 um), Buffer: 10 mM Ammonium Formate in Water pH 4.5, Mobile phase A: Buffer:MeCN (98:2), Mobile phase B: Buffer:MeCN (2:98), Flow rate: 1.0 ml/min. Rt: 2.35 min, wavelength: 220 nm. HPLC Method: SUNFIRE (150×4.6 mm) 3.5 micron, Buffer: 0.05% TFA in water, Mobile Phase A: Buffer:MeCN (95:5), Mobile Phase B: MeCN:Buffer (95:5), Flow: 1.0 ml/min, Wavelength: 254 nm, Rt: 20.94 min, Wavelength: 220 nm, Rt: 20.94 min. HPLC Method:) (Bridge Phenyl (150×4.6 mm) 3.5 micron SC/749, Buffer: 0.05% TFA in water, Mobile Phase A: Buffer:MeCN (95:5), Mobile Phase B: Buffer:MeCN (5:95), Flow: 1.0 ml/min, Wavelength: 254 nm, Rt: 11.40 min, Wavelength: 220 nm, Rt: 11.40 min.

Preparative HPLC Method

Flow: 16 ml/min, Gradient: T/% B: 0/50, 10/80, 16/80

| LCMS | | |
|---|---|---|
| Time | % A | % B |
| 0.0 | 100 | 0 |
| 1.7 | 0 | 100 |
| 3.2 | 0 | 100 |

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 12 | 100 |
| 15 | 100 |

Example 5

5-(3-(Bicyclo[1.1.1]pentan-1-ylcarbamoyl)phenyl)-6-ethoxy-2-(4-fluorophenyl)-N-methylbenzofuran-3-carboxamide

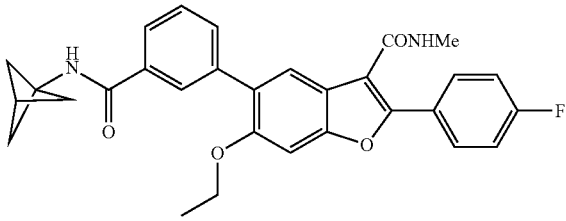

To a stirred solution of 3-(6-ethoxy-2-(4-fluorophenyl)-3-(methylcarbamoyl)benzofuran-5-yl)benzoic acid (30 mg, 0.069 mmol) and bicyclo[1.1.1]pentan-1-amine hydrochloride (8.28 mg, 0.069 mmol) in DMF (3.0 mL) at room temperature under $N_2$ atmosphere was added DIPEA (0.060 mL, 0.346 mmol). The mixture was cooled to 0° C., and HATU (39.5 mg, 0.104 mmol) was added to the mixture. The reaction mixture was allowed to stir at ambient temperature for 16 hr. After completion of the reaction (monitored by TLC), the mixture was diluted with water, and the product extracted with EtOAc (25 ml×3). The combined organic layers were washed with saturated brine solution, dried over $Na_2SO_4$, filtered and concentrated under reduced pressure. The crude solid product was purified by Prep HPLC to obtained 5-(3-(bicyclo[1.1.1]pentan-1-ylcarbamoyl)phenyl)-6-ethoxy-2-(4-fluorophenyl)-N-methylbenzofuran-3-carboxamide as a white solid. Yield: 21.00 mg, (60.5%). PREPARATIVE HPLC: Column: Kromosil C18

(19*250) mm*10 um, Mobile Phase: 10 mM Ammonium acetate (A): MeCN (B), Flow: 16 ml/min, Rt: 9.91 min. $^1$H NMR (400 MHz, CHLOROFORM-d) δ ppm=7.95-7.91 (m, 2H), 7.88-7.86 (m, 1H), 7.74 (td, J=1.5, 7.7 Hz, 1H), 7.71-7.67 (m, 2H), 7.48-7.43 (m, 1H), 7.20-7.15 (m, 2H), 7.11 (s, 1H), 6.55 (br. s., 1H), 5.85 (d, J=3.9 Hz, 1H), 4.08 (q, J=6.9 Hz, 2H), 3.00 (d, J=4.9 Hz, 3H), 2.52 (s, 1H), 2.22 (s, 6H), 1.37 (t, J=7.0 Hz, 3H). $^{19}$F NMR (376.6 MHz, CHLOROFORM-d) δ ppm: −110.33. LCMS: (ES+) m/z=499.0 (M+H)$^+$, Column-Acentis Express C18 (50×2.1 mm; 2.7 um), Buffer: 10 mM Ammonium Formate in Water pH 4.5, Mobile phase A: Buffer:MeCN (98:2), Mobile phase B: Buffer:MeCN (2:98), Flow: 1.0 ml/min. Rt: 2.42 min, wavelength: 220 nm. HPLC Method: SUNFIRE (150×4.6 mm) 3.5 micron, Buffer: 0.05% TFA in water, Mobile Phase A: Buffer:MeCN (95:5), Mobile Phase B: MeCN: Buffer (95:5), Flow: 1.0 ml/min, Wavelength: 254 nm, Rt: 20.32 min, Wavelength: 220 nm, Rt: 20.32 min. HPLC Method:) (Bridge Phenyl (150×4.6 mm) 3.5 micron SC/749, Buffer: 0.05% TFA in water, Mobile Phase A: Buffer:MeCN (95:5), Mobile Phase B: Buffer:MeCN (5:95), Flow: 1.0 ml/min, Wavelength: 254 nm, Rt: 18.17 min, Wavelength: 220 nm, Rt: 18.17 min.

Preparative HPLC Method

Flow: 16 ml/min, Gradient: T/% B: 0/30, 10/70

| LCMS | | |
|---|---|---|
| Time | % A | % B |
| 0.0 | 100 | 0 |
| 1.5 | 0 | 100 |
| 3.2 | 0 | 100 |

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 6

5-(3-((2-(1,2,4-Oxadiazol-3-yl)propan-2-yl)carbamoyl)phenyl)-6-ethoxy-2-(4-fluorophenyl)-N-methylbenzofuran-3-carboxamide

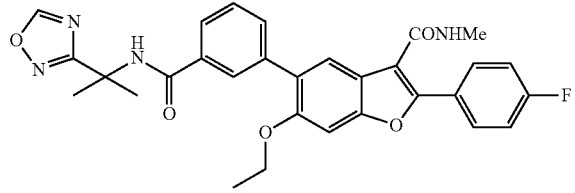

To a stirred solution of 3-(6-ethoxy-2-(4-fluorophenyl)-3-(methylcarbamoyl)benzofuran-5-yl) benzoic acid (30 mg, 0.069 mmol) and 2-(1,2,4-oxadiazol-3-yl)propan-2-amine hydrochloride (11.32 mg, 0.069 mmol) in DMF (3.0 mL) at room temperature under N$_2$ atmosphere was added DIPEA (0.060 mL, 0.346 mmol). The mixture was cooled to 0° C., and HATU (39.5 mg, 0.104 mmol) was added to the mixture, which was then stirred at room temperature for 16 hr. After completion of the reaction, the mixture was diluted with water, and the product extracted with EtOAc (25 ml×3). The combined organic layers were washed with saturated brine solution, dried over Na$_2$SO$_4$ and concentrated under reduced pressure. The crude product was purified by Prep HPLC to obtained 5-(3-((2-(1,2,4-oxadiazol-3-yl)propan-2-yl)carbamoyl)phenyl)-6-ethoxy-2-(4-fluorophenyl)-N-methylbenzofuran-3-carboxamide as a white solid. Yield: 31.00 mg, (82.55%). PREPARATIVE HPLC: Column: Kromosil C18 (19*250) mm*10 um, Mobile Phase: 10 mM Ammonium acetate (A): MeCN (B), Flow: 16 ml/min, Rt: 9.89 min. $^1$H NMR (400 MHz, CHLOROFORM-d) δ ppm: =8.65 (s, 1H), 7.97-7.91 (m, 3H), 7.78-7.74 (m, 1H), 7.71-7.68 (m, 2H), 7.50-7.45 (m, 1H), 7.18 (t, J=8.7 Hz, 2H), 7.12 (s, 1H), 6.77 (s, 1H), 5.85 (b s, 1H), 4.09 (q, J=6.9 Hz, 2H), 3.01 (d, J=4.9 Hz, 3H), 1.91 (s, 6H), 1.38 (t, J=6.9 Hz, 3H). $^{19}$F NMR (376.6 MHz, CHLOROFORM-d) δ ppm: −110.38. LCMS: (ES+) m/z observed=542.8, Column-Acentis Express C18 (50×2.1 mm; 2.7 um), Buffer: 10 mM Ammonium Formate in Water pH 4.5, Mobile phase A: Buffer:MeCN (98:2), Mobile phase B: Buffer:MeCN (2:98), Flow: 1.0 ml/min. Rt: 2.30 min, wavelength: 220 nm. HPLC Method: SUNFIRE (150×4.6 mm) 3.5 micron, Buffer: 0.05% TFA in water, Mobile Phase A: Buffer:MeCN (95:5), Mobile Phase B: MeCN: Buffer (95:5), Flow: 1.0 ml/min, Wavelength: 254 nm, Rt: 18.40 min, Wavelength: 220 nm, Rt: 18.40 min. HPLC Method:)(Bridge Phenyl (150×4.6 mm) 3.5 micron SC/749, Buffer: 0.05% TFA in water, Mobile Phase A: Buffer:MeCN (95:5), Mobile Phase B: Buffer:MeCN (5:95), Flow: 1.0 ml/min, Wavelength: 254 nm, Rt: 16.83 min, Wavelength: 220 nm, Rt: 16.83 min.

Preparative HPLC Method

Flow: 16 ml/min, Gradient: T/% B: 0/30, 10/70

| LCMS | | |
|---|---|---|
| Time | % A | % B |
| 0.0 | 100 | 0 |
| 1.5 | 0 | 100 |
| 3.2 | 0 | 100 |

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 7

6-Ethoxy-2-(4-fluorophenyl)-N-methyl-5-(3-((1-(pyrimidin-2-yl)cyclopropyl) carbamoyl)phenyl)benzofuran-3-carboxamide

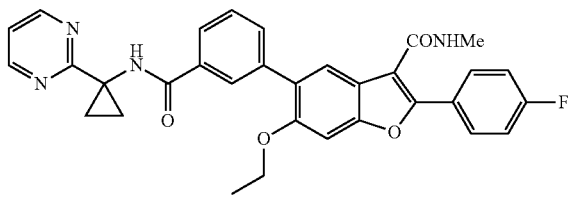

To a stirred solution of 3-(6-ethoxy-2-(4-fluorophenyl)-3-(methylcarbamoyl)benzofuran-5-yl)benzoic acid (25 mg, 0.058 mmol) and 1-(pyrimidin-2-yl)cyclopropanamine hydrochloride (10.89 mg, 0.063 mmol) in DMF (3.0 mL) under an nitrogen atmosphere was added TEA (0.040 mL, 0.288 mmol). The mixture was cooled to 0° C., and added with BOP (38.3 mg, 0.087 mmol) and then stirred at 25° C. for 16 hr. After completion of the reaction, the mixture was diluted with water, and the product extracted with EtOAc (25 ml×3). The combined organic layers were washed with saturated brine solution, dried over $Na_2SO_4$, filtered and concentrated under reduced pressure. The crude solid product was purified by Prep HPLC to afford 6-ethoxy-2-(4-fluorophenyl)-N-methyl-5-(3-((1-(pyrimidin-2-yl)cyclopropyl) carbamoyl) phenyl)benzofuran-3-carboxamide as a white solid. Yield: 12.00 mg, (37.79%). PREPARATIVE HPLC: Column: Kromosil C18 (19*250) mm*10 um, Mobile Phase: 10 mM Ammonium acetate (A): MeCN (B), Flow: 16 ml/min, Rt: 10.98 min. $^1$H NMR (400 MHz, CHLOROFORM-d) δ ppm=8.60 (d, J=4.9 Hz, 2H), 8.03 (t, J=1.6 Hz, 1H), 7.96-7.92 (m, 2H), 7.87-7.83 (m, 1H), 7.73-7.70 (m, 2H), 7.51-7.46 (m, 1H), 7.20-7.11 (m, 4H), 7.05 (t, J=4.8 Hz, 1H), 5.88 (b s, 1H), 4.09 (q, J=7.0 Hz, 2H), 3.01 (d, J=4.9 Hz, 3H), 1.84-1.80 (m, 2H), 1.63-1.59 (m, 2H), 1.39 (t, J=6.9 Hz, 3H). $^{19}$F NMR (376.6 MHz, CHLOROFORM-d) δ: −110.43. LCMS: (ES+) m/z observed=550.8, Column-Acentis Express C18 (50×2.1 mm; 2.7 um), Buffer: 10 mM Ammonium Formate in Water pH 4.5, Mobile phase A: Buffer:MeCN (98:2), Mobile phase B: Buffer:MeCN (2:98), Flow: 1.0 ml/min. Rt: 2.25 min, wavelength: 220 nm. HPLC Method: SUNFIRE (150×4.6 mm) 3.5 micron, Buffer: 0.05% TFA in water, Mobile Phase A: Buffer:MeCN (95:5), Mobile Phase B: MeCN: Buffer (95:5), Flow: 1.0 ml/min, Wavelength: 254 nm, Rt: 17.38 min, Wavelength: 220 nm, Rt: 17.38 min. HPLC Method:)(Bridge Phenyl (150×4.6 mm) 3.5 micron SC/749, Buffer: 0.05% TFA in water, Mobile Phase A: Buffer:MeCN (95:5), Mobile Phase B: Buffer:MeCN (5:95), Flow: 1.0 ml/min, Wavelength: 254 nm, Rt: 15.98 min, Wavelength: 220 nm, Rt: 15.98 min.

Preparative HPLC Method

Flow: 16 ml/min, Gradient: T/% B: 0/30, 10/70

| LCMS | | |
|---|---|---|
| Time | % A | % B |
| 0.0 | 100 | 0 |
| 1.5 | 0 | 100 |
| 3.2 | 0 | 100 |

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 8

5-(3-((1-Cyanocyclopropyl)carbamoyl)phenyl)-2-(4-fluorophenyl)-N-methyl-6-(2,2,2-trifluoroethoxy)benzofuran-3-carboxamide

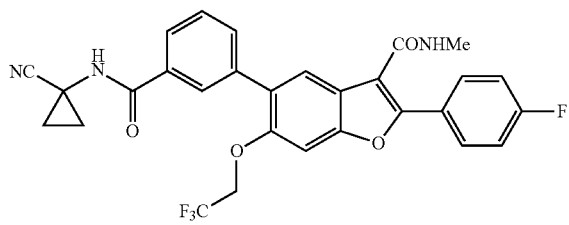

To a stirred solution of 3-(2-(4-fluorophenyl)-3-(methylcarbamoyl)-6-(2,2,2-trifluoro ethoxy)benzofuran-5-yl)benzoic acid (25 mg, 0.051 mmol) and 1-aminocyclopropanecarbonitrile hydrochloride (6.08 mg, 0.051 mmol) in DMF (2.5 mL) at room temperature under $N_2$ atmosphere was added DIPEA (0.045 mL, 0.256 mmol). The mixture was cooled to 0° C., and HATU (29.3 mg, 0.077 mmol) was added to the mixture, which was then stirred at room temperature for 16 hours. The mixture was diluted with water and extracted with EtOAc (25 ml×3). The combined organic layers were washed with saturated brine solution, dried over $Na_2SO_4$ and concentrated under reduced pressure. The crude solid product was purified by Prep HPLC to obtained 5-(3-((1-cyanocyclopropyl)carbamoyl)phenyl)-2-(4-fluorophenyl)-N-methyl-6-(2,2,2-trifluoroethoxy)benzofuran-3-carboxamide as a white solid. Yield: 17.00 mg, (60.11%). PREPARATIVE HPLC: Column: Sunfire C18 (19*150) mm*5 um, Mobile Phase: 10 mM Ammonium acetate (A): MeCN (B), Flow: 16 ml/min, Rt: 11.87 min. $^1$H NMR (400 MHz, CHLOROFORM-d) δ ppm=7.92-7.80 (m, 5H), 7.72 (d, J=7.9 Hz, 1H), 7.55-7.50 (m, 1H), 7.23-7.18 (m, 2H), 7.13 (s, 1H), 6.73 (s, 1H), 5.83 (bs, 1H), 4.34 (q, J=8.1 Hz, 2H), 3.00 (d, J=4.9 Hz, 3H), 1.69-1.65 (m, 2H), 1.42-1.37 (m, 2H). $^{19}$F NMR (376.6 MHz, CHLOROFORM-d) δ: −73.48, −109.40. LCMS: (ES+) m/z observed=551.8, Column-Acentis Express C18 (50×2.1 mm; 2.7 um), Buffer: 10 mM Ammonium Formate in Water pH 4.5, Mobile phase A: Buffer:MeCN (98:2), Mobile phase B: Buffer:MeCN (2:98), Flow: 1.0 ml/min. Rt: 2.25 min, wavelength: 220 nm. HPLC Method: SUNFIRE (150×4.6 mm) 3.5 micron, Buffer: 0.05% TFA in water, Mobile Phase A: Buffer:MeCN (95:5), Mobile Phase B: MeCN: Buffer (95:5), Flow: 1.0 ml/min, Wavelength: 254 nm, Rt: 18.00 min, Wavelength: 220 nm, Rt: 18.00 min. HPLC Method:) (Bridge Phenyl (150×4.6 mm) 3.5 micron SC/749, Buffer: 0.05% TFA in water, Mobile Phase A: Buffer:MeCN (95:5), Mobile Phase B: Buffer:MeCN (5:95), Flow: 1.0 ml/min, Wavelength: 254 nm, Rt: 16.83 min, Wavelength: 220 nm, Rt: 16.83 min.

Preparative HPLC Method

Flow: 16 ml/min, Gradient: T/% B: 0/30, 10/70

| LCMS | | |
|---|---|---|
| Time | % A | % B |
| 0.0 | 100 | 0 |
| 1.5 | 0 | 100 |
| 3.2 | 0 | 100 |

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 9

5-(3-((2-(1,2,4-Oxadiazol-3-yl)propan-2-yl)carbamoyl)-4-methoxyphenyl)-6-ethoxy-2-(4-fluorophenyl)-N-methylbenzofuran-3-carboxamide

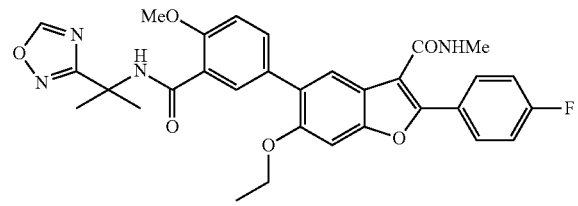

To a stirred mixture of 5-(6-ethoxy-2-(4-fluorophenyl)-3-(methylcarbamoyl)benzofuran-5-yl)-2-methoxybenzoic acid (20 mg, 0.043 mmol) and 2-(1,2,4-oxadiazol-3-yl)propan-2-amine hydrochloride (7.06 mg, 0.043 mmol) in DMF (3.0 mL) at room under a $N_2$ atmosphere temperature was added DIPEA (0.038 mL, 0.216 mmol). The mixture was cooled to 0° C., and HATU (24.61 mg, 0.065 mmol) was added to the mixture. The mixture was then stirred at 25° C. for 16 hr. After completion of the reaction, the mixture was diluted with water and the product extracted with EtOAc (25 ml×3). The combined organic layers were washed with saturated brine solution, dried over $Na_2SO_4$ and concentrated under reduced pressure. The crude solid product was purified by Prep HPLC to obtained 5-(3-((2-(1,2,4-oxadiazol-3-yl)propan-2-yl)carbamoyl)-4-methoxyphenyl)-6-ethoxy-2-(4-fluorophenyl)-N-methylbenzofuran-3-carboxamide as a white solid. Yield: 20.00 mg, (80.97%). PREPARATIVE HPLC: Column: Sunfire C18 (19*150) mm*5 um, Mobile Phase: 10 mM Ammonium acetate (A):

MeCN (B), Flow: 16 ml/min, Rt: 6.50 min. $^1$H NMR (400 MHz, CHLOROFORM-d) δ ppm=8.71 (s, 1H), 8.63 (s, 1H), 8.30 (d, J=2.4 Hz, 1H), 7.98-7.93 (m, 2H), 7.68-7.65 (m, 1H), 7.61 (s, 1H), 7.18-7.13 (m, 2H), 7.08-7.02 (m, 2H), 5.86 (bs, 1H), 4.08-4.02 (m, 5H), 3.01 (d, J=4.9 Hz, 3H), 1.89 (s, 6H), 1.36 (t, J=7.0 Hz, 3H). $^{19}$F NMR (376.6 MHz, CHLOROFORM-d) δ ppm: −110.83. LCMS: (ES+) m/z observed=572.8, Column-Acentis Express C18 (50×2.1 mm; 2.7 um), Buffer: 10 mM Ammonium Formate in Water pH 4.5, Mobile phase A: Buffer:MeCN (98:2), Mobile phase B: Buffer:MeCN (2:98), Flow: 1.0 ml/min. Rt: 2.33 min, wavelength: 220 nm. HPLC Method: SUNFIRE (150×4.6 mm) 3.5 micron, Buffer: 0.05% TFA in water, Mobile Phase A: Buffer:MeCN (95:5), Mobile Phase B: MeCN: Buffer (95:5), Flow: 1.0 ml/min, Wavelength: 254 nm, Rt: 19.34 min, Wavelength: 220 nm, Rt: 19.34 min. HPLC Method: XBridge Phenyl (150×4.6 mm) 3.5 micron SC/749, Buffer: 0.05% TFA in water, Mobile Phase A: Buffer:MeCN (95:5), Mobile Phase B: Buffer:MeCN (5:95), Flow: 1.0 ml/min, Wavelength: 254 nm, Rt: 17.46 min, Wavelength: 220 nm, Rt: 17.46 min.

Preparative HPLC Method

Flow: 16 ml/min, Gradient: T/% B: 0/30, 10/70

LCMS

| Time | % A | % B |
|---|---|---|
| 0.0 | 100 | 0 |
| 1.5 | 0 | 100 |
| 3.2 | 0 | 100 |

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 10

5-(3-((2-Cyanopropan-2-yl)carbamoyl)phenyl)-2-(4-fluorophenyl)-N-methyl-6-(2,2,2-trifluoroethoxy) benzofuran-3-carboxamide

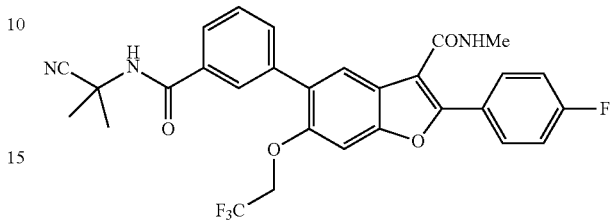

To a stirred mixture of 3-(2-(4-fluorophenyl)-3-(methylcarbamoyl)-6-(2,2,2-trifluoroethoxy) benzofuran-5-yl)benzoic acid (40 mg, 0.082 mmol) and 2-amino-2-methylpropanenitrile hydrochloride (9.90 mg, 0.082 mmol) in DMF (2.5 mL) at room temperature under a N$_2$ atmosphere was added DIPEA (0.072 mL, 0.410 mmol). The mixture was cooled to 0° C., and HATU (46.8 mg, 0.123 mmol) was added to the mixture, and then stirring was continued at r.t for 16 hr. After completion of the reaction, the mixture was diluted with water and the product extracted with EtOAc (25 ml×3). The combined organic layers were washed with saturated brine solution, dried over Na$_2$SO$_4$, filtered and concentrated under reduced pressure. The crude solid product was purified by Prep HPLC to obtained 5-(3-((2-cyanopropan-2-yl)carbamoyl)phenyl)-2-(4-fluorophenyl)-N-methyl-6-(2,2,2-trifluoroethoxy)benzofuran-3-carboxamide as a white solid. Yield: 12.00 mg, (26.40%). PREPARATIVE HPLC: Column: X-BRIDGE C-18 (19*150) mm*5 u, Mobile Phase: 10 mM Ammonium acetate (A): MeCN (B), Flow: 15 ml/min, Rt: 10.38 min. $^1$H NMR (400 MHz, CHLOROFORM-d) δ ppm=7.93-7.84 (m, 4H), 7.82 (s, 1H), 7.72-7.69 (m, 1H), 7.56-7.51 (m, 1H), 7.20 (t, J=8.7 Hz, 2H), 7.14 (s, 1H), 6.22 (s, 1H), 5.84 (bs, 1H), 4.36 (q, J=8.1 Hz, 2H), 3.01 (d, J=4.9 Hz, 3H), 1.84 (s, 6H). $^{19}$F NMR (376.6 MHz, CHLOROFORM-d) δ: −73.38, −109.44. LCMS: (ES+) m/z=554.2 (M+H)$^+$, Column-Acentis Express C18 (50×2.1 mm; 2.7 um), Buffer: 10 mM Ammonium Formate in Water pH 4.5, Mobile phase A: Buffer:MeCN (98:2), Mobile phase B: Buffer:MeCN (2:98), Flow: 1.0 ml/min. Rt: 2.18 min, wavelength: 220 nm. HPLC Method: SUNFIRE (150×4.6 mm) 3.5 micron, Buffer: 0.05% TFA in water, Mobile Phase A: Buffer:MeCN (95:5), Mobile Phase B: MeCN: Buffer (95:5), Flow: 1.0 ml/min, Wavelength: 254 nm, Rt: 19.37 min, Wavelength: 220 nm, Rt: 19.37 min. HPLC Method:)(Bridge Phenyl (150×4.6 mm) 3.5 micron SC/749, Buffer: 0.05% TFA in water, Mobile Phase A: Buffer:MeCN (95:5), Mobile Phase B: Buffer:MeCN (5:95), Flow: 1.0 ml/min, Wavelength: 254 nm, Rt: 17.00 min, Wavelength: 220 nm, Rt: 17.00 min.

Preparative HPLC Method

Flow: 15 ml/min, Gradient: T/% B: 0/30, 7/60, 10.5/60

LCMS

| Time | % A | % B |
|---|---|---|
| 0.0 | 100 | 0 |
| 1.7 | 0 | 100 |
| 3.4 | 0 | 100 |

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 11

5-(3-(Bicyclo[1.1.1]pentan-1-ylcarbamoyl)-4-methoxyphenyl)-6-ethoxy-2-(4-fluorophenyl)-N-methylbenzofuran-3-carboxamide

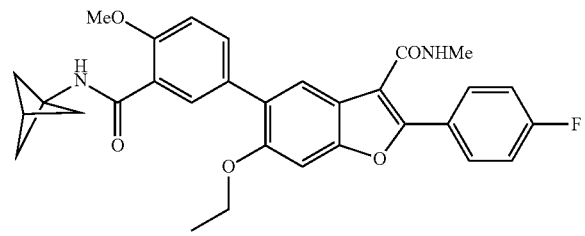

To a stirred mixture of 5-(6-ethoxy-2-(4-fluorophenyl)-3-(methylcarbamoyl)benzofuran-5-yl)-2-methoxybenzoic acid (20 mg, 0.043 mmol) and bicyclo[1.1.1]pentan-1-amine hydrochloride (5.16 mg, 0.043 mmol) in DMF (2.5 mL) at room temperature under a $N_2$ atmosphere was added DIPEA (0.038 mL, 0.216 mmol). The mixture was cooled to 0° C., and HATU (24.61 mg, 0.065 mmol) was added to the mixture. The mixture was then stirred at r.t for 16 hr. After completion of the reaction (monitored by TLC), the mixture was diluted with water and the product extracted with EtOAc (25 ml×3). The combined organic layers were washed with saturated brine solution, dried over $Na_2SO_4$ and concentrated under reduced pressure. The crude solid product was purified by Prep HPLC to obtained 5-(3-(bicyclo[1.1.1]-pentan-1-ylcarbamoyl)-4-methoxyphenyl)-6-ethoxy-2-(4-fluorophenyl)-N-methylbenzofuran-3-carboxamide as a white solid. Yield: 9.00 mg, (39.40%). PREPARATIVE HPLC: Column: X-BRIDGE C-18 (19*150) mm*5 um, Mobile Phase: 10 mM Ammonium acetate in water pH 4.5 with acetic acid (A): MeCN (B), Flow: 15 ml/min, Rt: 7.18 min. $^1$H NMR (400 MHz, CHLOROFORM-d) δ ppm=8.35 (d, J=2.4 Hz, 1H), 8.18 (s, 1H), 7.99-7.94 (m, 2H), 7.66 (dd, J=2.4, 8.6 Hz, 1H), 7.62 (s, 1H), 7.18-7.13 (m, 2H), 7.09 (s, 1H), 7.01 (d, J=8.6 Hz, 1H), 5.89-5.88 (br m, 1H), 4.07 (q, J=6.9 Hz, 2H), 4.01 (s, 3H), 3.02 (d, J=4.9 Hz, 3H), 2.50 (s, 1H), 2.21 (s, 6H), 1.38 (t, J=6.9 Hz, 3H). $^{19}$F NMR (376.6 MHz, CHLOROFORM-d) δ ppm: −110.84. LCMS: (ES+) m/z observed=528.8, Column-Acentis Express C18 (50×2.1 mm; 2.7 um), Buffer: 10 mM Ammonium Formate in Water pH 4.5, Mobile phase A: Buffer:MeCN (98:2), Mobile phase B: Buffer:MeCN (2:98), Flow: 1.0 ml/min. Rt: 2.44 min, wavelength: 220 nm. HPLC Method: SUNFIRE (150×4.6 mm) 3.5 micron, Buffer: 0.05% TFA in water, Mobile Phase A: Buffer:MeCN (95:5), Mobile Phase B: MeCN: Buffer (95:5), Flow: 1.0 ml/min, Wavelength: 254 nm, Rt: 21.85 min, Wavelength: 220 nm, Rt: 21.85 min. HPLC Method:)(Bridge Phenyl (150×4.6 mm) 3.5 micron SC/749, Buffer: 0.05% TFA in water, Mobile Phase A: Buffer:MeCN (95:5), Mobile Phase B: Buffer:MeCN (5:95), Flow: 1.0 ml/min, Wavelength: 254 nm, Rt: 18.69 min, Wavelength: 220 nm, Rt: 18.69 min.

Preparative HPLC Method

Flow: 15 ml/min, Gradient: T/% B: 0/50, 8/95, 8.5/95

LCMS

| Time | % A | % B |
|---|---|---|
| 0.0 | 100 | 0 |
| 1.7 | 0 | 100 |
| 3.0 | 0 | 100 |
| 3.2 | 100 | 0 |

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 12

6-Ethoxy-2-(4-fluorophenyl)-5-(4-methoxy-3-((1-(pyrimidin-2-yl)cyclo propyl)carbamoyl)phenyl)-N-methylbenzofuran-3-carboxamide

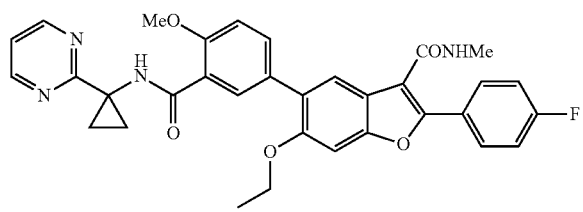

To a stirred solution of 5-(6-ethoxy-2-(4-fluorophenyl)-3-(methylcarbamoyl)benzofuran-5-yl)-2-methoxybenzoic acid (20 mg, 0.043 mmol) and 1-(pyrimidin-2-yl)cyclopropanamine hydrochloride (7.41 mg, 0.043 mmol) in DMF (2.5 mL) at room temperature under $N_2$ atmosphere was added DIPEA (0.038 mL, 0.216 mmol). The mixture was cooled to 0° C., and HATU (24.61 mg, 0.065 mmol) was added to the mixture. The reaction mixture was stirred at room temperature for 16 hr. After completion of the reaction, the mixture was diluted with water and the product extracted with EtOAc (25 ml×3). The combined organic layers were washed with saturated brine solution, dried over $Na_2SO_4$ and concentrated under reduced pressure. The crude solid product was purified by Prep HPLC to obtained 6-ethoxy-2-(4-fluorophenyl)-5-(4-methoxy-3-((1-(pyrimidin-2-yl)cyclopropyl)carbamoyl)phenyl)-N-methylbenzofuran-3-carboxamide as a white solid. Yield: 18.00 mg, (71.50%). PREPARATIVE HPLC: Column: X-BRIDGE C-18 (19*150) mm*5 um, Mobile Phase: 10 mM Ammonium acetate in water pH 4.5 with acetic acid (A): MeCN (B), Flow: 15 ml/min, Rt: 14.50 min. $^1$H NMR (400 MHz, CHLOROFORM-d) δ ppm=8.74 (s, 1H), 8.61 (d, J=4.9 Hz, 2H), 8.40 (s, 1H), 8.00-7.95 (m, 2H), 7.67 (dd, J=2.4, 8.6 Hz, 1H), 7.63 (s, 1H), 7.18-7.12 (m, 2H), 7.10-7.02 (m, 3H), 5.91 (b s, 1H), 4.10-4.04 (m, 5H), 3.02 (d, J=4.9 Hz, 3H), 1.86-1.81 (m, 2H), 1.55-1.53 (m, 2H), 1.38 (t, J=6.9 Hz, 3H). $^{19}$F NMR (376.6 MHz, CHLOROFORM-d) δ: -110.88. LCMS: (ES+) m/z observed=580.8, Column-Acentis Express C18 (50×2.1 mm; 2.7 um), Buffer: 10 mM Ammonium Formate in Water pH 4.5, Mobile phase A: Buffer:MeCN (98:2), Mobile phase B: Buffer:MeCN (2:98), Flow: 1.0 ml/min. Rt: 2.26 min, wavelength: 220 nm. HPLC Method: SUNFIRE (150×4.6 mm) 3.5 micron, Buffer: 0.05% TFA in water, Mobile Phase A: Buffer:MeCN (95:5), Mobile Phase B: MeCN: Buffer (95:5), Flow: 1.0 ml/min, Wavelength: 254 nm, Rt: 18.58 min, Wavelength: 220 nm, Rt: 18.58 min. HPLC Method:)(Bridge Phenyl (150×4.6 mm) 3.5 micron SC/749, Buffer: 0.05% TFA in water, Mobile Phase A: Buffer:MeCN (95:5), Mobile Phase B: Buffer:MeCN (5:95), Flow: 1.0 ml/min, Wavelength: 254 nm, Rt: 16.44 min, Wavelength: 220 nm, Rt: 16.44 min.

Preparative HPLC Method

Flow: 15 ml/min, Gradient: T/% B: 0/20, 8/55, 14.5/55

| LCMS | | |
|---|---|---|
| Time | % A | % B |
| 0.0 | 100 | 0 |
| 1.7 | 0 | 100 |
| 3.0 | 0 | 100 |
| 3.2 | 100 | 0 |

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 13

5-(6-Ethoxy-2-(4-fluorophenyl)-3-(methylcarbamoyl)benzofuran-5-yl)-2-methoxy-N-(1-(pyrimidin-2-yl)cyclopropyl)nicotinamide

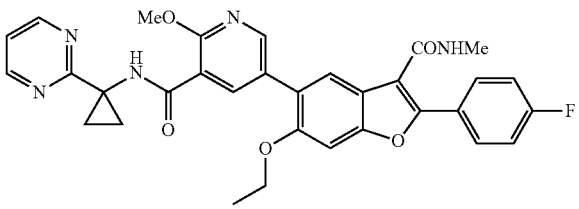

To a stirred solution of 5-(6-ethoxy-2-(4-fluorophenyl)-3-(methylcarbamoyl)benzofuran-5-yl)-2-methoxynicotinic acid (40 mg, 0.086 mmol) and 1-(pyrimidin-2-yl)cyclopropanamine hydrochloride (14.78 mg, 0.086 mmol) in DMF (5.0 mL) at room temperature under a $N_2$ atmosphere was added DIPEA (0.075 mL, 0.431 mmol). The mixture was cooled to 0° C., and HATU (49.1 mg, 0.129 mmol) was added to the mixture. The reaction mixture was stirred at room temperature for 16 hr. After completion of the reaction (monitored by TLC), the mixture was diluted with water and the product extracted with EtOAc (25 ml×3). The combined organic layers were washed with saturated brine solution, dried over $Na_2SO_4$ and concentrated under reduced pressure. The crude solid product obtained was purified by Prep HPLC to obtained 5-(6-ethoxy-2-(4-fluorophenyl)-3-(methylcarbamoyl)benzofuran-5-yl)-2-methoxy-N-(1-(pyrimidin-2-yl)cyclopropyl)nicotinamide as a white solid. Yield: 30 mg, (59.80%). PREPARATIVE HPLC: Column:

X-BRIDGE C-18 (19*150) mm*5 um, Mobile Phase: 10 mM Ammonium acetate in water (A): MeCN (B), Flow: 15 ml/min, Rt: 10.39 min. $^1$H NMR (400 MHz, DMSO-d$_6$) δ ppm=8.96 (s, 1H), 8.70 (d, J=4.9 Hz, 2H), 8.50 (s, 1H), 8.44 (s, 1H), 8.38 (d, J=2.5 Hz, 1H), 8.00-7.95 (m, 2H), 7.57 (s, 1H), 7.50 (s, 1H), 7.41-7.36 (m, 2H), 7.30 (t, J=4.9 Hz, 1H), 4.18 (q, J=6.9 Hz, 2H), 4.08 (s, 3H), 2.84 (d, J=4.6 Hz, 3H), 1.65-1.61 (m, 2H), 1.47-1.43 (m, 2H), 1.32 (t, J=6.9 Hz, 3H). $^{19}$F NMR (376.6 MHz, DMSO-d$_6$) δ: −111.40. LCMS: (ES+) m/z=582.2 (M+H)$^+$, Column-Acentis Express C18 (50×2.1 mm; 2.7 um), Buffer: 10 mM Ammonium Formate in Water pH 4.5, Mobile phase A: Buffer:MeCN (98:2), Mobile phase B: Buffer:MeCN (2:98), Flow: 1.0 ml/min. Rt: 2.17 min, wavelength: 220 nm. HPLC Method: SUNFIRE (150×4.6 mm) 3.5 micron, Buffer: 0.05% TFA in water pH 2.5, Mobile Phase A: Buffer:MeCN (95:5), Mobile Phase B: MeCN: Buffer (95:5), Flow: 1.0 ml/min, Wavelength: 254 nm, Rt: 18.58 min, Wavelength: 220 nm, Rt: 18.58 min. HPLC Method:)(Bridge Phenyl (150×4.6 mm) 3.5 micron SC/749, Buffer: 0.05% TFA in water pH 2.5, Mobile Phase A: Buffer:MeCN (95:5), Mobile Phase B: Buffer:MeCN (5:95), Flow: 1.0 ml/min, Wavelength: 254 nm, Rt: 16.11 min, Wavelength: 220 nm, Rt: 16.11 min.

Preparative HPLC Method

Flow: 15 ml/min, Gradient: T/% B: 0/20, 8/70, 11/70

LCMS

| Time | % A | % B |
|------|-----|-----|
| 0.0 | 100 | 0 |
| 1.7 | 0 | 100 |
| 3.4 | 0 | 100 |

HPLC Method: SUNFIRE C18 (150×4.6 mm) 3.5 micron

| Time | B % |
|------|-----|
| 0 | 10 |
| 25 | 100 |
| 30 | 100 |

HPLC Method:)(Bridge Phenyl (150×4.6 mm) 3.5 micron SC/749

| Time | B % |
|------|-----|
| 0 | 10 |
| 25 | 100 |
| 30 | 100 |

Example 14

N-(2-(1,2,4-oxadiazol-3-yl)propan-2-yl)-5-(6-ethoxy-2-(4-fluorophenyl)-3-(methylcarbamoyl)benzofuran-5-yl)-2-methoxynicotinamide

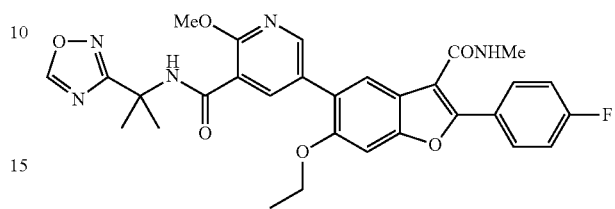

To a stirred solution of 5-(6-ethoxy-2-(4-fluorophenyl)-3-(methylcarbamoyl)benzofuran-5-yl)-2-methoxynicotinic acid (40 mg, 0.086 mmol) and 2-(1,2,4-oxadiazol-3-yl)propan-2-amine hydrochloride (14.06 mg, 0.086 mmol) in DMF (5.0 mL) at room temperature under a nitrogen atmosphere was added DIPEA (0.075 mL, 0.431 mmol). The mixture was cooled to 0° C., and HATU (49.1 mg, 0.129 mmol) was added to the mixture. The reaction mixture was allowed to stir at room temperature for 16 hr. After completion of the reaction (monitored by TLC), the mixture was diluted with water, stirred for 5 min and the solid filtered. The crude product obtained was purified by Prep HPLC to obtained N-(2-(1,2,4-oxadiazol-3-yl)propan-2-yl)-5-(6-ethoxy-2-(4-fluorophenyl)-3-(methylcarbamoyl)benzofuran-5-yl)-2-methoxynicotinamide as a white solid. Yield: 17 mg, (34.3%). PREPARATIVE HPLC: Column: X-BRIDGE C-18 (19*150) mm*5 um, Mobile Phase: 10 mM Ammonium acetate in water (A): MeCN (B), Flow: 15 ml/min, Rt: 11.08 min. $^1$H NMR (400 MHz, DMSO-d$_6$) δ ppm=9.48 (s, 1H), 8.67 (s, 1H), 8.49 (d, J=2.4 Hz, 1H), 8.42 (d, J=4.6 Hz, 1H), 8.22 (d, J=2.4 Hz, 1H), 7.99-7.95 (m, 2H), 7.55 (s, 1H), 7.49 (s, 1H), 7.41-7.36 (m, 2H), 4.16 (q, J=7.0 Hz, 2H), 4.08 (s, 3H), 2.84 (d, J=4.6 Hz, 3H), 1.74 (s, 6H), 1.31 (t, J=6.9 Hz, 3H). $^{19}$F NMR (376.6 MHz, DMSO-d$_6$) δ: −11.40. LCMS: (ES+) m/z=574.2 (M+H)$^+$, Column-Acentis Express C18 (50×2.1 mm; 2.7 um), Buffer: 10 mM Ammonium Formate in Water, Mobile phase A: Buffer:MeCN (98:2), Mobile phase B: Buffer:MeCN (2:98), Flow: 1.0 ml/min. Rt: 2.24 min, wavelength: 220 nm. HPLC Method: SUNFIRE (150×4.6 mm) 3.5 micron, Buffer: 0.05% TFA in water pH 2.5, Mobile Phase A: Buffer:MeCN (95:5), Mobile Phase B: MeCN: Buffer (95:5), Flow: 1.0 ml/min, Wavelength: 254 nm, Rt: 19.89 min, Wavelength: 220 nm, Rt: 19.89 min. HPLC Method:)(Bridge Phenyl (150×4.6 mm) 3.5 micron SC/749, Buffer: 0.05% TFA in water pH 2.5, Mobile Phase A: Buffer:MeCN (95:5), Mobile Phase B: Buffer:MeCN (5:95), Flow: 1.0 ml/min, Wavelength: 254 nm, Rt: 17.20 min, Wavelength: 220 nm, Rt: 17.20 min.

Preparative HPLC Method

Flow: 15 ml/min, Gradient: T/% B: 0/20, 9/75, 11.5/75

LCMS

| Time | % A | % B |
|---|---|---|
| 0.0 | 100 | 0 |
| 1.7 | 0 | 100 |
| 3.4 | 0 | 100 |

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 15

N-(bicyclo[1.1.1]pentan-1-yl)-5-(6-ethoxy-2-(4-fluorophenyl)-3-(methylcarbamoyl)benzofuran-5-yl)-2-methoxynicotinamide

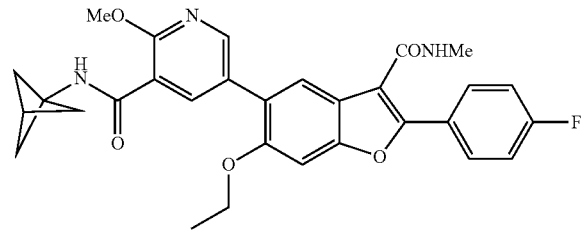

To a stirred solution of 5-(6-ethoxy-2-(4-fluorophenyl)-3-(methylcarbamoyl)benzofuran-5-yl)-2-methoxynicotinic acid (40 mg, 0.086 mmol) and bicyclo[1.1.1]pentan-1-amine hydrochloride (10.30 mg, 0.086 mmol) in DMF (5.0 mL) at room temperature under a nitrogen atmosphere was added DIPEA (0.075 mL, 0.431 mmol). The mixture was cooled to 0° C., and HATU (49.1 mg, 0.129 mmol) was added to the mixture. The reaction mixture was stirred at room temperature for 16 hr. After completion of the reaction (monitored by TLC), the mixture was diluted with water, stirred for 5 min and the solid filtered. The crude product obtained was purified by Prep HPLC to obtained N-(bicyclo[1.1.1]pentan-1-yl)-5-(6-ethoxy-2-(4-fluorophenyl)-3-(methylcarbamoyl)benzofuran-5-yl)-2-methoxynicotinamide as a white solid. Yield: 15.5 mg, (33.8%). PREPARATIVE HPLC: Column: X-BRIDGE C-18 (19*150) mm*5 u, Mobile Phase: 10 mM Ammonium acetate in water (A): MeCN (B), Flow: 15 ml/min, Rt: 10.37 min. $^1$H NMR (400 MHz, DMSO-$d_6$) δ ppm=8.63 (s, 1H), 8.45 (d, J=2.5 Hz, 1H), 8.41 (d, J=4.6 Hz, 1H), 8.22 (d, J=2.5 Hz, 1H), 7.99-7.94 (m, 2H), 7.54 (s, 1H), 7.48 (s, 1H), 7.40-7.35 (m, 2H), 4.16 (q, J=6.9 Hz, 2H), 4.01 (s, 3H), 2.83 (d, J=4.6 Hz, 3H), 2.47 (s, 1H), 2.10 (s, 6H), 1.31 (t, J=7.0 Hz, 3H). $^{19}$F NMR (376.6 MHz, DMSO-$d_6$) δ; −111.41. LCMS: (ES+) m/z=530.2 (M+H)$^+$, Column-Acentis Express C18 (50×2.1 mm; 2.7 um), Buffer: 10 mM Ammonium Formate in Water, Mobile phase A: Buffer: MeCN (98:2), Mobile phase B: Buffer:MeCN (2:98), Flow: 1.0 ml/min. Rt: 2.35 min, wavelength: 220 nm. HPLC Method: SUNFIRE (150×4.6 mm) 3.5 micron, Buffer: 0.05% TFA in water pH 2.5, Mobile Phase A: Buffer:MeCN (95:5), Mobile Phase B: MeCN: Buffer (95:5), Flow: 1.0 ml/min, Wavelength: 254 nm, Rt: 22.24 min, Wavelength: 220 nm, Rt: 22.24 min. HPLC Method:)(Bridge Phenyl (150×4.6 mm) 3.5 micron SC/749, Buffer: 0.05% TFA in water pH 2.5, Mobile Phase A: Buffer:MeCN (95:5), Mobile Phase B: Buffer:MeCN (5:95), Flow: 1.0 ml/min, Wavelength: 254 nm, Rt: 18.58 min, Wavelength: 220 nm, Rt: 18.58 min.

Preparative HPLC Method

Flow: 15 ml/min, Gradient: T/% B: 0/20, 8/80, 11.5/80

LCMS

| Time | % A | % B |
|---|---|---|
| 0.0 | 100 | 0 |
| 1.7 | 0 | 100 |
| 3.4 | 0 | 100 |

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 16

N-(2-(1,2,4-oxadiazol-3-yl)propan-2-yl)-5-(6-ethoxy-2-(4-fluorophenyl)-3-(methylcarbamoyl)benzofuran-5-yl)-2-(methoxy-$d_3$)nicotinamide

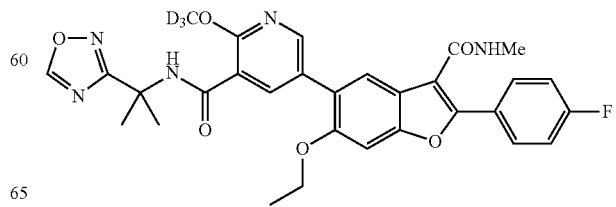

To a stirred solution of 5-(6-ethoxy-2-(4-fluorophenyl)-3-(methylcarbamoyl)benzofuran-5-yl)-2-(methoxy-d₃)nicotinic acid (30 mg, 0.064 mmol) (prepared in a similar manner as described for 5-(6-ethoxy-2-(4-fluorophenyl)-3-(methylcarbamoyl)benzofuran-5-yl)-2-methoxynicotinic acid) and 2-(1,2,4-oxadiazol-3-yl)propan-2-amine hydrochloride (10.50 mg, 0.064 mmol) in DMF (5.0 mL) at room temperature under a nitrogen atmosphere was added DIPEA (0.075 mL, 0.431 mmol). After cooling to 0° C., the mixture was added with HATU (49.1 mg, 0.129 mmol). The reaction mixture was allowed to stir at room temperature for 16 hr. After completion of the reaction (monitored by TLC), the reaction mixture was diluted with water, stirred for 5 min and the solid filtered. The crude product was recrystalized from EtOAc and pet. ether to afford the desired compound in pure form. Yield: 23.00 mg, (61.5%). $^1$H NMR (400 MHz, DMSO-d₆) δ ppm=9.50 (s, 1H), 8.68 (s, 1H), 8.49 (d, J=2.5 Hz, 1H), 8.43 (d, J=4.6 Hz, 1H), 8.22 (d, J=2.4 Hz, 1H), 7.99-7.95 (m, 2H), 7.55 (s, 1H), 7.49 (s, 1H), 7.38 (t, J=8.9 Hz, 2H), 4.16 (q, J=6.9 Hz, 2H), 2.83 (d, J=4.6 Hz, 3H), 1.74 (s, 6H), 1.31 (t, J=6.9 Hz, 3H). $^{19}$F NMR (376.6 MHz, DMSO-d₆) δ: -111.38. LCMS: (ES+) m/z=577.2 (M+H)⁺, Column-Acentis Express C18 (50×2.1 mm; 2.7 um), Buffer: 10 mM Ammonium Formate in Water, Mobile phase A: Buffer:MeCN (98:2), Mobile phase B: Buffer:MeCN (2:98), Flow: 1.0 ml/min. Rt: 2.23 min, wavelength: 220 nm. HPLC Method: SUNFIRE (150×4.6 mm) 3.5 micron, Buffer: 0.05% TFA in water pH 2.5, Mobile Phase A: Buffer:MeCN (95:5), Mobile Phase B: MeCN:Buffer (95:5), Flow: 1.0 ml/min, Wavelength: 254 nm, Rt: 19.82 min, Wavelength: 220 nm, Rt: 19.82 min. HPLC Method:)(Bridge Phenyl (150×4.6 mm) 3.5 micron SC/749, Buffer: 0.05% TFA in water pH 2.5, Mobile Phase A: Buffer:MeCN (95:5), Mobile Phase B: Buffer:MeCN (5:95), Flow: 1.0 ml/min, Wavelength: 254 nm, Rt: 17.25 min, Wavelength: 220 nm, Rt: 17.25 min.

| LCMS | | |
|---|---|---|
| Time | % A | % B |
| 0.0 | 100 | 0 |
| 1.7 | 0 | 100 |
| 3.4 | 0 | 100 |

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 17

N-(2-cyanopropan-2-yl)-5-(6-ethoxy-2-(4-fluorophenyl)-3-(methylcarbamoyl)benzofuran-5-yl)-2-(methoxy-d₃)nicotinamide

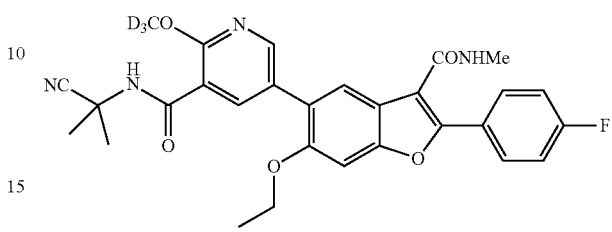

To a stirred solution of 5-(6-ethoxy-2-(4-fluorophenyl)-3-(methylcarbamoyl)benzofuran-5-yl)-2-(methoxy-d₃)nicotinic acid (35 mg, 0.075 mmol) and 2-amino-2-methylpropanenitrile hydrochloride (9.03 mg, 0.075 mmol) in DMF (5.0 mL) at room temperature under a nitrogen atmosphere was added DIPEA (0.065 mL, 0.374 mmol). The mixture was cooled to 0° C., and HATU (42.7 mg, 0.112 mmol) was added to the mixture. The reaction mixture was stirred at room temperature for 16 hr. After completion of the reaction (monitored by TLC), the reaction mixture was diluted with water, stirred for 5 min and the solid filtered. The crude product was purified by Prep HPLC to obtained the desired compound as a white solid. Yield: 11.50 mg, (28.79%). PREPARATIVE HPLC: Column: Sunfire C-18 (19*150) mm*5 um, Mobile Phase: 20 mM Ammonium acetate pH 4.5 with acetic acid (A): MeCN (B), Flow: 18 ml/min, Rt: 10.74 min. $^1$H NMR (400 MHz, DMSO-d₆) δ ppm=8.62 (s, 1H), 8.50 (d, J=2.4 Hz, 1H), 8.44 (d, J=4.6 Hz, 1H), 8.23 (s, 1H), 8.00-7.96 (m, 2H), 7.58 (s, 1H), 7.50 (s, 1H), 7.41-7.36 (m, 2H), 4.17 (q, J=7.0 Hz, 2H), 2.84 (d, J=4.6 Hz, 3H), 1.72 (s, 6H), 1.32 (t, J=6.9 Hz, 3H). $^{19}$F NMR (376.6 MHz, DMSO-d₆) δ: -111.37. LCMS: (ES+) m/z=534.4 (M+H)⁺, Column-Acentis Express C18 (50×2.1 mm; 2.7 um), Buffer: 10 mM Ammonium Acetate pH-5 adjusted with HCOOH, Mobile phase A: Buffer:MeCN (95:5), Mobile phase B: Buffer:MeCN (5:95), Flow: 0.8 ml/min. Rt: 1.11 min, wavelength: 220 nm. HPLC Method: SUNFIRE (150×4.6 mm) 3.5 micron, Buffer: 0.05% TFA in water pH 2.5, Mobile Phase A: Buffer:MeCN (95:5), Mobile Phase B: MeCN:Buffer (95:5), Flow: 1.0 ml/min, Wavelength: 254 nm, Rt: 19.96 min, Wavelength: 220 nm, Rt: 19.96 min. HPLC Method:)(Bridge Phenyl (150×4.6 mm) 3.5 micron SC/749, Buffer: 0.05% TFA in water pH 2.5, Mobile Phase A: Buffer:MeCN (95:5), Mobile Phase B: Buffer:MeCN (5:95), Flow: 1.0 ml/min, Wavelength: 254 nm, Rt: 16.94 min, Wavelength: 220 nm, Rt: 16.94 min.

Preparative HPLC Method

Flow: 18 ml/min, Gradient: T/% B: 0/30, 10/80

| LCMS | | |
|---|---|---|
| Time | % A | % B |
| 0.0 | 95 | 5 |
| 1.1 | 5 | 95 |
| 1.7 | 5 | 95 |

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 18

Preparation of 5-(3-((2-(1,2,4-oxadiazol-3-yl)propan-2-yl)carbamoyl)-4-methoxyphenyl)-2-(4-fluorophenyl)-N-methyl-6-(2,2,2-trifluoroethoxy)benzofuran-3-carboxamide

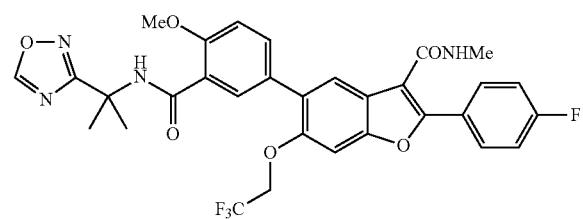

To a stirred mixture of 5-(2-(4-fluorophenyl)-3-(methylcarbamoyl)-6-(2,2,2-trifluoro ethoxy)benzofuran-5-yl)-2-methoxybenzoic acid (20 mg, 0.039 mmol) and 2-(1,2,4-oxadiazol-3-yl) propan-2-amine hydrochloride (6.32 mg, 0.039 mmol) in DMF (2.5 mL) at room temperature under a nitrogen atmosphere was added DIPEA (0.034 mL, 0.193 mmol). The mixture was cooled to 0° C., and HATU (22.05 mg, 0.058 mmol) was added to the mixture. The reaction mixture was allowed to stir at room temperature for 16 hr. After completion of the reaction (monitored by TLC), the reaction mixture was diluted with water, stirred for 5 min and the solid filtered. The crude product obtained was purified by Prep HPLC to obtained 5-(3-((2-(1,2,4-oxadiazol-3-yl)propan-2-yl)carbamoyl)-4-methoxyphenyl)-2-(4-fluorophenyl)-N-methyl-6-(2,2,2-trifluoroethoxy)benzofuran-3-carboxamide as a white solid. Yield: 10 mg, (41.10%). PREPARATIVE HPLC: Column: Inertsil ODS (21.2×250 mm) 7 um, Mobile Phase: 10 mM Ammonium acetate pH 4.5 with acetic acid (A): MeCN (B), Flow: 18 ml/min, Rt: 15.47 min. $^1$H NMR (400 MHz, CHLOROFORM-d) δ ppm=8.71 (s, 1H), 8.64 (s, 1H), 8.26 (s, 1H), 7.97-7.93 (m, 2H), 7.70 (s, 1H), 7.67 (dd, J=2.5, 8.6 Hz, 1H), 7.19-7.15 (m, 2H), 7.13 (s, 1H), 7.05 (d, J=8.7 Hz, 1H), 5.87-5.86 (bs, 1H), 4.25 (q, J=8.1 Hz, 2H), 4.08 (s, 3H), 3.02 (d, J=4.9 Hz, 3H), 1.90 (s, 6H). $^{19}$F NMR (376.6 MHz, CHLOROFORM-d) δ: −73.64, −110.11. LCMS: (ES+) m/z=627.2 (M+H)$^+$, Column-Acentis Express C18 (50×2.1 mm; 2.7 um), Buffer: 10 mM Ammonium Formate in Water, Mobile phase A: Buffer:MeCN (98:2), Mobile phase B: Buffer:MeCN (2:98), Flow: 1.0 ml/min. Rt: 2.23 min, wavelength: 220 nm. HPLC Method: SUNFIRE (150×4.6 mm) 3.5 micron, Buffer: 0.05% TFA in water pH 2.5, Mobile Phase A: Buffer:MeCN (95:5), Mobile Phase B: MeCN:Buffer (95:5), Flow: 1.0 ml/min, Wavelength: 254 nm, Rt: 11.78 min, Wavelength: 220 nm, Rt: 11.78 min. HPLC Method:)(Bridge Phenyl (150×4.6 mm) 3.5 micron SC/749, Buffer: 0.05% TFA in water pH 2.5, Mobile Phase A: Buffer:MeCN (95:5), Mobile Phase B: Buffer:MeCN (5:95), Flow: 1.0 ml/min, Wavelength: 254 nm, Rt: 10.92 min, Wavelength: 220 nm, Rt: 10.92 min.

Preparative HPLC Method

Flow: 18 ml/min, Gradient: T/% B: 0/50, 8/90

| LCMS | | |
|---|---|---|
| Time | % A | % B |
| 0.0 | 100 | 0 |
| 1.7 | 0 | 100 |
| 3.4 | 0 | 100 |

HPLC Method: SUNFIRE C18 (150×4.6 mm) 3.5 micron

| Time | B % |
|---|---|
| 0 | 10 |
| 12 | 100 |
| 15 | 100 |

HPLC Method:)(Bridge Phenyl (150×4.6 mm) 3.5 micron SC/749

| Time | B % |
|---|---|
| 0 | 10 |
| 12 | 100 |
| 15 | 100 |

Example 19

5-(3-((2-(1,2,4-Oxadiazol-3-yl)propan-2-yl)carbamoyl)phenyl)-6-(2,2-difluoroethoxy)-2-(4-fluorophenyl)-N-m ethylbenzofuran-3-carboxamide

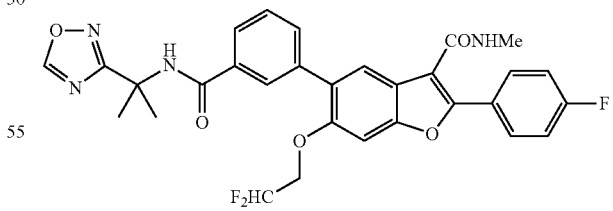

To a stirred solution of 3-(6-(2,2-difluoroethoxy)-2-(4-fluorophenyl)-3-(methylcarbamoyl) benzofuran-5-yl)benzoic acid (50 mg, 0.107 mmol) (prepared according to Scheme 2), and 2-(1,2,4-oxadiazol-3-yl)propan-2-amine hydrochloride (17.43 mg, 0.107 mmol) in DMF (5 mL) at room temperature under a nitrogen atmosphere was added DIPEA (0.093 mL, 0.533 mmol). The mixture was cooled to 0° C., and HATU (60.8 mg, 0.160 mmol) was added to the mixture. The reaction mixture was stirred at room temperature for 16 hr. After completion of the reaction (monitored by TLC), the reaction mixture was diluted with water, stirred for 5 min and the solid filtered. The crude product obtained was purified by Prep HPLC to obtained 5-(3-((2-(1,2,4-oxadiazol-3-yl)propan-2-yl)carbamoyl)phenyl)-6-(2,2-difluoroethoxy)-2-(4-fluorophenyl)-N-methylbenzofuran-3-carboxamide as a white solid. Yield: 25 mg, (40.57%). PREPARATIVE HPLC: Column: Xbridge C18 (19*150 mm) 5 um, Mobile Phase: 10 mm Ammonium acetate pH 4.5 with acetic acid (A): MeCN (B), Flow: 15 ml/min, Rt: 11.43 min. $^1$H NMR (400 MHz, DMSO-$d_6$) δ ppm=9.45 (s, 1H), 8.72 (s, 1H), 8.47 (q, J=4.5 Hz, 1H), 8.00-7.94 (m, 3H), 7.82-7.69 (m, 2H), 7.60 (d, J=13.3 Hz, 2H), 7.51 (t, J=7.8 Hz, 1H), 7.43-7.36 (m, 2H), 6.50-6.19 (m, 1H), 4.45 (dt, J=3.6, 14.4 Hz, 2H), 2.83 (d, J=4.6 Hz, 3H), 1.71 (s, 6H). $^{19}$F NMR (376.6 MHz, DMSO-$d_6$) δ: −111.21, −125.48. LCMS: (ES+) m/z=579.2 (M+H)$^+$, Column-Acentis Express C18 (50×2.1 mm; 2.7 um), Buffer: 10 mM Ammonium Formate in Water, Mobile phase A: Buffer:MeCN (98:2), Mobile phase B: Buffer:MeCN (2:98), Flow: 1.0 ml/min. Rt: 2.13 min, wavelength: 220 nm. HPLC Method: SUNFIRE (150× 4.6 mm) 3.5 micron, Buffer: 0.05% TFA in water pH 2.5, Mobile Phase A: Buffer:MeCN (95:5), Mobile Phase B: MeCN: Buffer (95:5), Flow: 1.0 ml/min, Wavelength: 254 nm, Rt: 11.11 min, Wavelength: 220 nm, Rt: 11.11 min. HPLC Method:)(Bridge Phenyl (150×4.6 mm) 3.5 micron SC/749, Buffer: 0.05% TFA in water pH 2.5, Mobile Phase A: Buffer:MeCN (95:5), Mobile Phase B: Buffer:MeCN (5:95), Flow: 1.0 ml/min, Wavelength: 254 nm, Rt: 16.43 min, Wavelength: 220 nm, Rt: 16.43 min.

Preparative HPLC Method

Flow: 15 ml/min, Gradient: T/% B: 0/30, 8/60

| LCMS | | |
|---|---|---|
| Time | % A | % B |
| 0.0 | 100 | 0 |
| 1.7 | 0 | 100 |
| 3.4 | 0 | 100 |

HPLC Method: SUNFIRE C18 (150×4.6 mm) 3.5 micron

| Time | B % |
|---|---|
| 0 | 10 |
| 12 | 100 |
| 15 | 100 |

HPLC Method:)(Bridge Phenyl (150×4.6 mm) 3.5 micron SC/749

| Time | B % |
|---|---|
| 0 | 10 |
| 12 | 100 |
| 15 | 100 |

Example 20

6-(2,2-difluoroethoxy)-2-(4-fluorophenyl)-N-methyl-5-(3-((1-(pyrimidin-2-yl)cyclopropyl)carbamoyl)phenyl)benzofuran-3-carboxamide

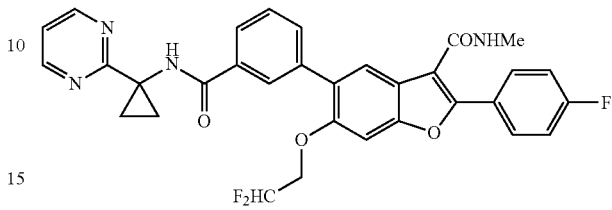

To a stirred solution of 3-(6-(2,2-difluoroethoxy)-2-(4-fluorophenyl)-3-(methylcarbamoyl)benzofuran-5-yl)benzoic acid (50 mg, 0.107 mmol) and 1-(pyrimidin-2-yl)cyclopropanamine hydrochloride (18.28 mg, 0.107 mmol) in DMF (5 mL) at room temperature under a nitrogen atmosphere were added DIPEA (0.093 mL, 0.533 mmol). The mixture was cooled to 0° C., and HATU (60.8 mg, 0.160 mmol) was added to the mixture. The reaction mixture was stirred at room temperature for 16 hr. After completion of the reaction (monitored by TLC), the reaction mixture was diluted with water, stirred for 5 min and the solid filtered. The crude product was purified by Prep HPLC to obtained 6-(2,2-difluoroethoxy)-2-(4-fluorophenyl)-N-methyl-5-(3-((1-(pyrimidin-2-yl)cyclo propyl)carbamoyl)phenyl)benzofuran-3-carboxamide as a white solid. Yield: 16 mg, (25.5%). PREPARATIVE HPLC: Column: Symmetry C18 (19*250) mm*5 um, Mobile Phase: 10 mm Ammonium acetate in water (A): MeCN (B), Flow: 15 ml/min, Rt: 14.39 min. $^1$H NMR (400 MHz, DMSO-$d_6$) δ ppm=9.21 (s, 1H), 8.67 (d, J=4.8 Hz, 2H), 8.46 (d, J=4.8 Hz, 1H), 8.07 (s, 1H), 7.99-7.93 (m, 2H), 7.90 (d, J=7.8 Hz, 1H), 7.71 (d, J=8.0 Hz, 1H), 7.60 (d, J=12.3 Hz, 2H), 7.53 (t, J=7.7 Hz, 1H), 7.42-7.35 (m, 2H), 7.27 (t, J=4.8 Hz, 1H), 6.52-6.17 (m, 1H), 4.45 (dt, J=3.4, 14.5 Hz, 2H), 2.82 (d, J=4.5 Hz, 3H), 1.65-1.58 (m, 2H), 1.40-1.33 (m, 2H). $^{19}$F NMR (376.6 MHz, DMSO-$d_6$) δ ppm: −111.22, −125.45. LCMS: (ES+) m/z=587.2 (M+H)$^+$, Column-Acentis Express C18 (50×2.1 mm; 2.7 um), Buffer: 10 mM Ammonium Formate in Water, Mobile phase A: Buffer:MeCN (98:2), Mobile phase B: Buffer:MeCN (2:98), Flow: 1.0 ml/min. Rt: 2.08 min, wavelength: 220 nm. HPLC Method: SUNFIRE (150×4.6 mm) 3.5 micron, Buffer: 0.05% TFA in water pH 2.5, Mobile Phase A: Buffer:MeCN (95:5), Mobile Phase B: MeCN: Buffer (95:5), Flow: 1.0 ml/min, Wavelength: 254 nm, Rt: 10.59 min, Wavelength: 220 nm, Rt: 10.59 min. HPLC Method:)(Bridge Phenyl (150×4.6 mm) 3.5 micron SC/749, Buffer: 0.05% TFA in water pH 2.5, Mobile Phase A: Buffer:MeCN (95:5), Mobile Phase B: Buffer:MeCN (5:95), Flow: 1.0 ml/min, Wavelength: 254 nm, Rt: 9.88 min, Wavelength: 220 nm, Rt: 9.88 min.

Preparative HPLC Method

Flow: 15 ml/min, Gradient: T/% B: 0/20, 10/70

LCMS

| Time | % A | % B |
|---|---|---|
| 0.0 | 100 | 0 |
| 1.7 | 0 | 100 |
| 3.4 | 0 | 100 |

HPLC Method: SUNFIRE C18 (150×4.6 mm) 3.5 micron

| Time | B % |
|---|---|
| 0 | 10 |
| 12 | 100 |
| 15 | 100 |

HPLC Method:)(Bridge Phenyl (150×4.6 mm) 3.5 micron SC/749

| Time | B % |
|---|---|
| 0 | 10 |
| 12 | 100 |
| 15 | 100 |

Example 21

5-(3-((2-(1,2,4-oxadiazol-3-yl)propan-2-yl)carbamoyl)phenyl)-2-(4-fluorophenyl)-N-methyl-6-(2,2,2-trifluoroethoxy)benzofuran-3-carboxamide

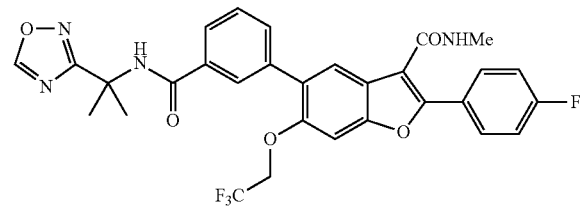

To a stirred solution of 3-(2-(4-fluorophenyl)-3-(methylcarbamoyl)-6-(2,2,2-trifluoroethoxy)benzofuran-5-yl)benzoic acid (40 mg, 0.082 mmol) and 2-(1,2,4-oxadiazol-3-yl)propan-2-amine hydrochloride (13.43 mg, 0.082 mmol) in DMF (5 mL) at room temperature under a nitrogen atmosphere was added DIPEA (0.072 mL, 0.410 mmol). After cooling the mixture to 0° C., HATU (46.8 mg, 0.123 mmol) was added to the mixture. The reaction mixture was allowed to stir at room temperature for 16 hr. After completion of the reaction (monitored by TLC), the reaction mixture was diluted with water, stirred for 5 min and the solid filtered. The crude product was recrystalized by using EtOAc (2 ml) and pet. ether (10 ml) to obtained pure 5-(3-((2-(1,2,4-oxadiazol-3-yl)propan-2-yl)carbamoyl)phenyl)-2-(4-fluorophenyl)-N-methyl-6-(2,2,2-trifluoroethoxy)benzofuran-3-carboxamide as a white solid. Yield: 31 mg, (63.32%). $^1$H NMR (400 MHz, DMSO-d$_6$) δ ppm=9.42 (s, 1H), 8.71 (s, 1H), 8.46 (d, J=4.8 Hz, 1H), 8.00-7.94 (m, 3H), 7.81 (s, 1H), 7.69-7.65 (m, 2H), 7.60 (s, 1H), 7.54-7.49 (m, 1H), 7.39 (t, J=8.9 Hz, 2H), 4.92-4.83 (m, 2H), 2.84 (s, 3H), 1.70 (s, 6H). $^{19}$F NMR (376.6 MHz, DMSO-d$_6$) δ: −72.29, −111.09. LCMS: (ES+) m/z=597.2 (M+H)$^+$, Column-Acentis Express C18 (50×2.1 mm; 2.7 um), Buffer: 10 mM Ammonium Formate in Water, Mobile phase A: Buffer:MeCN (98:2), Mobile phase B: Buffer:MeCN (2:98), Flow: 1.0 ml/min. Rt: 2.20 min, wavelength: 220 nm. HPLC Method: SUNFIRE (150×4.6 mm) 3.5 micron, Buffer: 0.05% TFA in water pH 2.5, Mobile Phase A: Buffer:MeCN (95:5), Mobile Phase B: MeCN: Buffer (95:5), Flow: 1.0 ml/min, Wavelength: 254 nm, Rt: 18.58 min, Wavelength: 220 nm, Rt: 18.58 min. HPLC Method:)(Bridge Phenyl (150×4.6 mm) 3.5 micron SC/749, Buffer: 0.05% TFA in water pH 2.5, Mobile Phase A: Buffer: MeCN (95:5), Mobile Phase B: Buffer:MeCN (5:95), Flow: 1.0 ml/min, Wavelength: 254 nm, Rt: 17.17 min, Wavelength: 220 nm, Rt: 17.17 min.

LCMS

| Time | % A | % B |
|---|---|---|
| 0.0 | 100 | 0 |
| 1.7 | 0 | 100 |
| 3.2 | 0 | 100 |

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 22

5-(3-((2-(1,2,4-Oxadiazol-3-yl)propan-2-yl)carbamoyl)phenyl)-6-(ethoxy-1,1,2,2,2-d$_5$)-2-(4-fluorophenyl)-N-methylbenzofuran-3-carboxamide

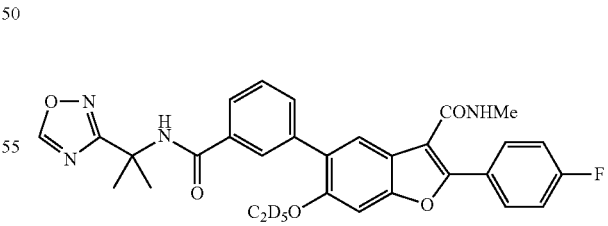

To a stirred solution of 3-(6-(ethoxy-1,1,2,2,2-d$_5$)-2-(4-fluorophenyl)-3-(methylcarbamoyl)benzofuran-5-yl)benzoic acid (40 mg, 0.091 mmol) and 2-(1,2,4-oxadiazol-3-yl)propan-2-amine hydrochloride (14.93 mg, 0.091 mmol) in DMF (4 mL) at room temperature under a nitrogen atmosphere was added DIPEA (0.080 mL, 0.456 mmol). The mixture was cooled to 0° C., and HATU (52.0 mg, 0.137 mmol) was added to the mixture. The reaction mixture was stirred at room temperature for 16 hr. After completion of the reaction (monitored by TLC), the reaction mixture was diluted with water, stirred for 5 min and the solid filtered. The crude product was purified by Prep HPLC to obtained desired compound as a white solid. Yield: 17 mg, (34.03%). PREPARATIVE HPLC: Column: Xbridge C-18 (19*150 mm) 5 um, Mobile Phase: 10 mM Ammonium acetate in water (A): MeCN (B), Flow: 16 ml/min, Rt: 8.74 min. $^1$H NMR (300 MHz, DMSO-$d_6$) δ ppm=9.43 (s, 1H), 8.73 (s, 1H), 8.44 (d, J=4.7 Hz, 1H), 8.00-7.92 (m, 3H), 7.81-7.66 (m, 2H), 7.54-7.45 (m, 3H), 7.41-7.33 (m, 2H), 2.83 (s, 3H), 1.70 (s, 6H). $^{19}$F NMR (376.6 MHz, DMSO-$d_6$) δ: −111.48. LCMS: (ES+) m/z=548.2 (M+H)$^+$, Column-Acentis Express C18 (50×2.1 mm; 2.7 um), Buffer: 10 mM Ammonium Formate in Water, Mobile phase A: Buffer:MeCN (98:2), Mobile phase B: Buffer:MeCN (2:98), Flow: 1.0 ml/min. Rt: 2.25 min, wavelength: 220 nm. HPLC Method: SUNFIRE (150×4.6 mm) 3.5 micron, Buffer: 0.05% TFA in water pH 2.5, Mobile Phase A: Buffer:MeCN (95:5), Mobile Phase B: MeCN: Buffer (95:5), Flow: 1.0 ml/min, Wavelength: 254 nm, Rt: 18.96 min, Wavelength: 220 nm, Rt: 18.96 min. HPLC Method:)(Bridge Phenyl (150×4.6 mm) 3.5 micron SC/749, Buffer: 0.05% TFA in water pH 2.5, Mobile Phase A: Buffer:MeCN (95:5), Mobile Phase B: Buffer:MeCN (5:95), Flow: 1.0 ml/min, Wavelength: 254 nm, Rt: 16.71 min, Wavelength: 220 nm, Rt: 16.71 min.

Preparative HPLC Method

Flow: 16 ml/min, Gradient: T/% B: 0/20, 10/85

LCMS

| Time | % A | % B |
|------|-----|-----|
| 0.0  | 100 | 0   |
| 1.7  | 0   | 100 |
| 3.0  | 0   | 100 |
| 3.2  | 100 | 0   |

HPLC Method: SUNFIRE C18 (150×4.6 mm) 3.5 micron

| Time | B % |
|------|-----|
| 0    | 10  |
| 25   | 100 |
| 30   | 100 |

HPLC Method:)(Bridge Phenyl (150×4.6 mm) 3.5 micron SC/749

| Time | B % |
|------|-----|
| 0    | 10  |
| 25   | 100 |
| 30   | 100 |

Example 23

5-(3-((2-(1,2,4-Oxadiazol-3-yl)propan-2-yl)carbamoyl)-4-methoxyphenyl)-2-(4-fluorophenyl)-6-isopropoxy-N-methylbenzofuran-3-carboxamide

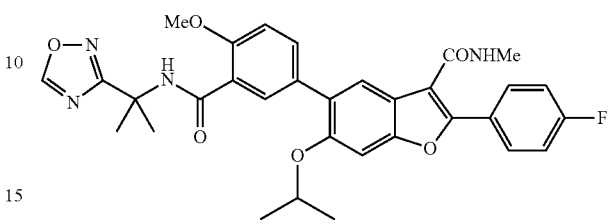

To a stirred solution of 5-(2-(4-fluorophenyl)-6-isopropoxy-3-(methylcarbamoyl)benzofuran-5-yl)-2-methoxybenzoic acid (35 mg, 0.073 mmol) and 2-(1,2,4-oxadiazol-3-yl)propan-2-amine hydrochloride (11.99 mg, 0.073 mmol) in DMF (4 mL) at room temperature under nitrogen atmosphere was added DIPEA (0.064 mL, 0.367 mmol). The mixture was cooled to 0° C., and HATU (41.8 mg, 0.110 mmol) was added to the mixture. The reaction mixture was allowed to stir at room temperature for 16 hr. After completion of the reaction (monitored by TLC), the reaction mixture was diluted with water, stirred for 5 min and the solid filtered. The crude product was purified by Prep HPLC to obtained 5-(3-((2-(1,2,4-oxadiazol-3-yl)propan-2-yl)carbamoyl)-4-methoxyphenyl)-2-(4-fluorophenyl)-6-isopropoxy-N-methylbenzofuran-3-carboxamide as a white solid. Yield: 23 mg, (53.50%). PREPARATIVE HPLC: Column: Xbridge C-18 (19*150 mm) 5 um, Mobile Phase: 10 mm Ammonium acetate in water (A): MeCN (B), Flow: 16 ml/min, Rt: 10.74 min. $^1$H NMR (400 MHz, DMSO-$d_6$) δ ppm=9.45 (s, 1H), 8.63 (s, 1H), 8.42 (d, J=4.6 Hz, 1H), 7.99-7.93 (m, 2H), 7.89 (d, J=2.4 Hz, 1H), 7.66 (dd, J=2.4, 8.6 Hz, 1H), 7.46 (d, J=4.6 Hz, 2H), 7.41-7.35 (m, 2H), 7.24 (d, J=8.7 Hz, 1H), 4.70 (quin, J=6.1 Hz, 1H), 4.00 (s, 3H), 2.83 (s, 3H), 1.73 (s, 6H), 1.25 (d, J=6.0 Hz, 6H). $^{19}$F NMR (376.6 MHz, DMSO-$d_6$) δ: −111.52. LCMS: (ES+) m/z=587.2 (M+H)$^+$, Column-Acentis Express C18 (50×2.1 mm; 2.7 um), Buffer: 10 mM Ammonium Formate in Water, Mobile phase A: Buffer:MeCN (98:2), Mobile phase B: Buffer:MeCN (2:98), Flow: 1.0 ml/min. Rt: 2.39 min, wavelength: 220 nm. HPLC Method: SUNFIRE (150×4.6 mm) 3.5 micron, Buffer: 0.05% TFA in water pH 2.5, Mobile Phase A: Buffer:MeCN (95:5), Mobile Phase B: MeCN: Buffer (95:5), Flow: 1.0 ml/min, Wavelength: 254 nm, Rt: 20.85 min, Wavelength: 220 nm, Rt: 20.85 min. HPLC Method:)(Bridge Phenyl (150×4.6 mm) 3.5 micron SC/749, Buffer: 0.05% TFA in water pH 2.5, Mobile Phase A: Buffer:MeCN (95:5), Mobile Phase B: Buffer:MeCN (5:95), Flow: 1.0 ml/min, Wavelength: 254 nm, Rt: 18.01 min, Wavelength: 220 nm, Rt: 18.01 min.

Preparative HPLC Method

Flow: 16 ml/min, Gradient: T/% B: 0/30, 10/70

| LCMS | | |
|---|---|---|
| Time | % A | % B |
| 0.0 | 100 | 0 |
| 1.7 | 0 | 100 |
| 3.0 | 0 | 100 |
| 3.2 | 100 | 0 |

HPLC Method: SUNFIRE C18 (150×4.6 mm) 3.5 micron,

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 24

5-(3-((2-(1,2,4-oxadiazol-3-yl)propan-2-yl)carbamoyl)-4-ethylphenyl)-6-ethoxy-2-(4-fluorophenyl)-N-methylbenzofuran-3-carboxamide

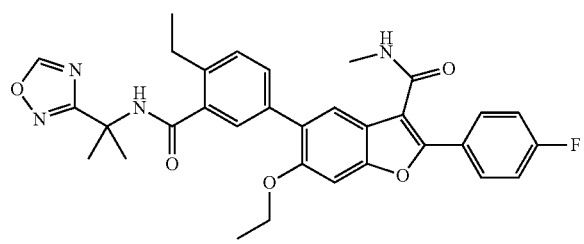 [SMILES: CCOc1cc2oc(-c3ccc(F)cc3)c(C(=O)NC)c2cc1-c1ccc(CC)c(C(=O)NC(C)(C)c2ncon2)c1]

To a solution of 5-(6-ethoxy-2-(4-fluorophenyl)-3-(methylcarbamoyl)benzofuran-5-yl)-2-ethylbenzoic acid (0.028 g, 0.061 mmol), DIPEA (0.032 mL, 0.182 mmol) and HATU (0.023 g, 0.061 mmol) in DMF (4 mL) at 0° C. was added 2-(1,2,4-oxadiazol-3-yl)propan-2-amine hydrochloride (0.012 g, 0.073 mmol). The reaction was stirred at 25° C. for 3 hr, and then quenched with water. The solid precipitated out was filtered and dried to obtain crude 5-(3-((2-(1,2,4-oxadiazol-3-yl)propan-2-yl)carbamoyl)-4-ethylphenyl)-6-ethoxy-2-(4-fluorophenyl)-N-methylbenzofuran-3-carboxamide, which was purified by Preparative HPLC to obtain a white solid product. Yield: 0.009 g (26%). Preparative HPLC Method: Xbridge C-18 (4.6×250) mm, 5 micron, Mobile Phase A: 10 mM Ammonium Acetate in water pH 4.6 adjusted with acetic acid, Mobile Phase B: MeCN. Flow: 1 ml/min, Rt min: 14.55. $^1$H NMR (400 MHz, METHANOL-d$_4$) δ ppm=9.16 (s, 1H), 7.97-7.91 (m, 2H), 7.62-7.56 (m, 3H), 7.35-7.31 (m, 2H), 7.26 (t, J=8.9 Hz, 2H), 4.15 (q, J=7.0 Hz, 2H), 2.97 (s, 3H), 2.84 (q, J=7.6 Hz, 2H), 1.80 (s, 6H), 1.41 (t, J=7.0 Hz, 3H), 1.30 (t, J=7.6 Hz, 3H). LCMS: (ES+) m/z=571.2 (M+H)$^+$. Column: Ascentis Express C18 (50×2.1 mm-2.7 µm). M phase A: 10 mM Ammonium Formate in Water:MeCN (98:2). M phase B: 10 mM Ammonium Formate in Water:MeCN (2:98). Flow: 1 ml/min. Rt: 2.45 min wavelength: 220 nm., with gradient:

| Time | % A | % B |
|---|---|---|
| 0.0 | 100.0 | 0.0 |
| 1.7 | 0.0 | 100.0 |
| 3.0 | 0.0 | 100.0 |
| 3.2 | 100.0 | 0.0 |

HPLC Method: COLUMN: Kinetex C-8 (150×4.6 mm) 2.6 micron. Mobile Phase A: 0.05% TFA in Water: Acetonitrile (95:5). Mobile Phase B: Acetonitrile: 0.05% TFA in Water (95:5). Flow: 1.0 ml/min. Wavelength: 254 nm, R$_t$ min: 17.11. Wavelength: 220 nm, R$_t$ min: 17.11. HPLC Method:)(Bridge Phenyl (150×4.6 mm) 3.5 micron SC/749. Mobile Phase A: 0.05% TFA in water: Acetonitrile (95:5). Mobile Phase B: Acetonitrile: 0.05% TFA in water (95:5) Flow: 1.0 ml/min. Wavelength: 254 nm. Rt min: 18.10. Wavelength: 220 nm. Rt min: 18.10.

HPLC Method: Kinetex C-8 (150×4.6 mm) 2.6 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 25

5-(3-((2-(1,2,4-oxadiazol-3-yl)propan-2-yl)carbamoyl)-4-methoxyphenyl)-2-(4-fluorophenyl)-N-methyl-6-propoxybenzofuran-3-carboxamide

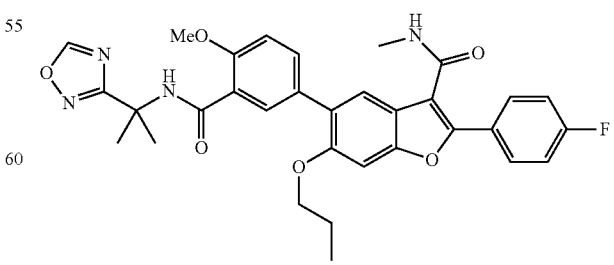

To a mixture of 5-(2-(4-fluorophenyl)-3-(methylcarbamoyl)-6-propoxybenzofuran-5-yl)-2-methoxybenzoic acid (0.05 g, 0.105 mmol), DIPEA (0.055 mL, 0.314 mmol) and HATU (0.040 g, 0.105 mmol) in DMF (4 mL) in a 25 ml round-bottomed flask at 0° C. was added 2-(1,2,4-oxadiazol-3-yl)propan-2-amine hydrochloride (0.021 g, 0.126 mmol) slowly. The mixture was stirred at 25° C. for 3 hours. After completion of the reaction, the mixture was added ice-cold water, the solid formed filtered and dried. The solid product was washed with ether (2×4 ml) to give pure 5-(3-((2-(1,2,4-oxadiazol-3-yl)propan-2-yl)carbamoyl)-4-methoxyphenyl)-2-(4-fluorophenyl)-N-methyl-6-propoxybenzofuran-3-carboxamide as a white solid. Yield: 40 mg (65%). $^1$H NMR (400 MHz, METHANOL-$d_4$) δ ppm=9.18 (s, 1H), 8.07 (d, J=2.4 Hz, 1H), 7.96-7.91 (m, 2H), 7.73 (dd, J=2.4, 8.6 Hz, 1H), 7.54 (s, 1H), 7.31-7.22 (m, 4H), 4.10 (s, 3H), 4.03 (t, J=6.2 Hz, 2H), 2.96 (s, 3H), 1.86 (s, 6H), 1.81-1.75 (m, 2H), 0.99 (t, J=7.4 Hz, 3H). $^{19}$F NMR (376.6 MHz, METHANOL-$d_4$): δ ppm=−113.45. LCMS: 587.2 (ES+) m/z=(M+H)$^+$. Column-Ascentis Express C18 (50×2.1 mm-2.7 μm). M phase A: 10 mM Ammonium Formate: MeCN (98:2). M phase B: 10 mM Ammonium Formate:MeCN (2:98). Flow: 1 ml/min., Rt min: 2.41, wavelength: 220 nm., and gradient:

| Time | % A | % B |
|---|---|---|
| 0.0 | 100.0 | 0.0 |
| 1.7 | 0.0 | 100.0 |
| 3.4 | 0.0 | 100.0 |

HPLC Method: COLUMN: SUNFIRE C18 (150×4.6 mm) 3.5 micron. Mobile Phase A: 0.05% TFA in Water: Acetonitrile (95:5). Mobile Phase B: Acetonitrile: 0.05% TFA in Water (95:5). Flow: 1.0 ml/min. Wavelength: 254 nm, Rt min: 21.46. Wavelength: 220 nm, Rt min: 21.46. HPLC Method: COLUMN: Kinetex C-8 (150×4.6 mm) 2.6 micron. Mobile phase A: 0.05% TFA in Water: Acetonitrile (95:5). Mobile phase B: Acetonitrile: 0.05% TFA in Water (95:5). Flow: 1.0 ml\min. Wavelength: 254 nm. Rt min: 17.34. Wavelength: 220 nm. Rt min: 17.34.

HPLC Method: SUNFIRE C18 (150×4.6 mm) 3.5 micron

| Time | B % |
|---|---|
| 0 | 10 |
| 25 | 100 |
| 30 | 100 |

HPLC Method: Kinetex C-8 (150×4.6 mm) 2.6 micron

| Time | B % |
|---|---|
| 0 | 10 |
| 25 | 100 |
| 30 | 100 |

Example 26

5-(3-((2-(1,2,4-oxadiazol-3-yl)propan-2-yl)carbamoyl)-4-methoxyphenyl)-2-(4-fluorophenyl)-6-isobutoxy-N-methylbenzofuran-3-carboxamide

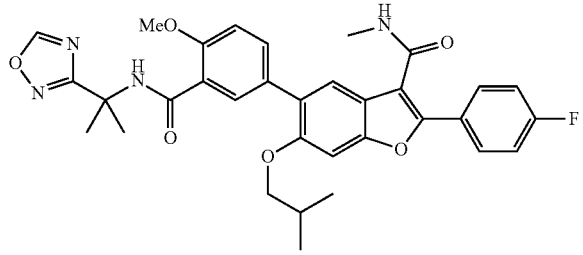 [SMILES: CNC(=O)c1c(-c2ccc(F)cc2)oc2cc(OCC(C)C)c(-c3ccc(OC)c(C(=O)NC(C)(C)c4ncon4)c3)cc12]

To a solution of 5-(2-(4-fluorophenyl)-6-isobutoxy-3-(methylcarbamoyl)benzofuran-5-yl)-2-methoxybenzoic acid (0.028 g, 0.057 mmol), DIPEA (0.030 mL, 0.171 mmol) and HATU (0.022 g, 0.057 mmol) in DMF (4 mL) at 0° C. was added 2-(1,2,4-oxadiazol-3-yl)propan-2-amine hydrochloride (0.011 g, 0.068 mmol). The reaction was stirred at 25° C. for 3 hours. To the reaction mixture was added ice-water, the solid formed was filtered and dried. The solid product was washed with ether (2×4 ml), and the ether layer was decanted and residual solvent removed by concentrating under reduced vacuum to give 5-(3-((2-(1,2,4-oxadiazol-3-yl)propan-2-yl)carbamoyl)-4-methoxyphenyl)-2-(4-fluorophenyl)-6-isobutoxy-N-methylbenzofuran-3-carboxamide as a white solid. Yield: 0.03 g (88%). $^1$H NMR (400 MHz, METHANOL-$d_4$) δ ppm=9.17 (s, 1H), 8.07 (d, J=2.4 Hz, 1H), 7.96-7.91 (m, 2H), 7.72 (dd, J=2.4, 8.6 Hz, 1H), 7.54 (s, 1H), 7.29-7.22 (m, 4H), 4.10 (s, 3H), 3.84 (d, J=6.2 Hz, 2H), 2.96 (s, 3H), 2.06-1.99 (m, 1H), 1.86 (s, 6H), 0.97 (d, J=6.7 Hz, 6H). $^{19}$F NMR (376.6 MHz, METHANOL-$d_4$): δ ppm=−113.46. LCMS: (ES+) m/z=601.2 (M+H)$^+$. Column-Ascentis Express C18 (50×2.1 mm-2.7 μm). M phase A: 10 mM Ammonium Formate in Water: MeCN (98:2). M phase B: 10 mM Ammonium Formate in Water:MeCN (2:98). Flow: 1 ml/Min., Rt min: 2.38, wavelength: 220 nm., and gradient:

| Time | % A | % B |
|---|---|---|
| 0.0 | 100.0 | 0.0 |
| 1.7 | 0.0 | 100.0 |
| 3.4 | 0.0 | 100.0 |

HPLC Method: COLUMN: SUNFIRE C18 (150×4.6 mm) 3.5 micron. Mobile Phase A: 0.05% TFA in Water: Acetonitrile (95:5). Mobile Phase B: Acetonitrile: 0.05% TFA in Water (95:5). Flow: 1.0 ml/min. Wavelength: 254 nm, Rt min: 22.43. Wavelength: 220 nm, Rt min: 22.43. HPLC Method: COLUMN:)(Bridge Phenyl (150×4.6 mm) 3.5 micron SC/749. Mobile phase A: 0.05% TFA in Water: Acetonitrile (95:5). Mobile phase B: Acetonitrile:0.05% TFA in Water (95:5). Flow: 1.0 ml\min. Wavelength: 254 nm. Rt min: 19.04. Wavelength: 220 nm. Rt min: 19.04.

HPLC Method: SUNFIRE C18 (150×4.6 mm) 3.5 micron

| Time | B % |
| --- | --- |
| 0 | 10 |
| 25 | 100 |
| 30 | 100 |

HPLC Method:)(Bridge Phenyl (150×4.6 mm) 3.5 micron SC/749

| Time | B % |
| --- | --- |
| 0 | 10 |
| 25 | 100 |
| 30 | 100 |

Example 27

5-(3-((2-(1,2,4-oxadiazol-3-yl)propan-2-yl)carbamoyl)-4-(methoxy-d₃)phenyl)-6-ethoxy-2-(4-fluorophenyl)-N-methylbenzofuran-3-carboxamide

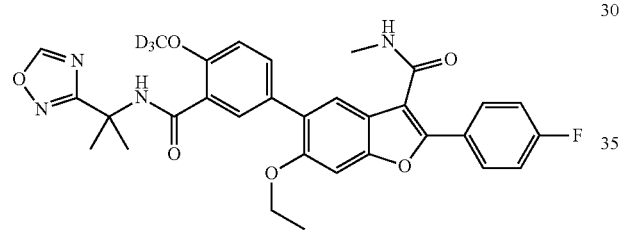

To a solution of 5-(6-ethoxy-2-(4-fluorophenyl)-3-(methylcarbamoyl)benzofuran-5-yl)-2-(methoxy-d₃)benzoic acid (0.04 g, 0.086 mmol), DIPEA (0.045 mL, 0.257 mmol) and HATU (0.033 g, 0.086 mmol) in DMF (4 mL) at 0° C. was added 2-(1,2,4-oxadiazol-3-yl)propan-2-amine hydrochloride (0.017 g, 0.103 mmol). The reaction was stirred at 25° C. for 4 hours. The reaction mixture was diluted with ice-cold water, the solid filtered and dried under suction. The crude product was submitted for reverse phase prep HPLC purification to give 5-(3-((2-(1,2,4-oxadiazol-3-yl)propan-2-yl)carbamoyl)-4-(methoxy-d₃)phenyl)-6-ethoxy-2-(4-fluorophenyl)-N-methylbenzofuran-3-carboxamide. Preparative HPLC Method: Column: Inertsil ODS (250×4.6 mm, 5 μm). Mobile phase A: 10 mM Ammonium Acetate in Water pH 4.6 adjusted with acetic acid. Mobile phase B: MeCN, Flow: 1.0 ml/min., Rt: 15.89 min. wavelength $^1$H NMR (400 MHz, METHANOL-$d_4$) δ ppm=9.18 (s, 1H) 8.06 (d, J=2.38 Hz, 1H) 7.93 (m, 2H) 7.73 (dd, J=8.63, 2.42 Hz, 1H) 7.53 (s, 1H) 7.25 (m, 4H) 4.12 (q, J=6.96 Hz, 2H) 2.96 (s, 3H) 1.86 (s, 6H) 1.37 (t, J=6.96 Hz, 3H). $^{19}$F NMR (376.6 MHz, METHANOL-$d_4$): δ ppm=−113.42. LCMS: for (ES+) m/z=576.2 (M+H)$^+$. Column-Ascentis Express C18 (50×2.1 mm-2.7 μm) M phase A: 2% MeCN-98% H₂O-10 mM NH₄COOH, M phase B: 98% MeCN-2% H₂O-10 mM NH₄COOH. Flow: 1 ml/min. Rt min: 2.23, wavelength: 254 nm., and gradient:

| Time | % A | % B |
| --- | --- | --- |
| 0.0 | 100 | 0.0 |
| 1.7 | 0.0 | 100.0 |
| 3.4 | 0.0 | 100.0 |

HPLC Method: COLUMN: SUNFIRE C18 (150×4.6 mm) 3.5 micron. Mobile Phase A: 0.05% TFA in Water: Acetonitrile (95:5). Mobile Phase B: Acetonitrile: 0.05% TFA in Water (95:5). Flow: 1.0 ml/min. Wavelength: 254 nm, Rt min: 19.46. Wavelength: 220 nm, Rt min: 19.46. HPLC Method:)(Bridge Phenyl (150×4.6 mm) 3.5 micron. Mobile Phase A: 0.05% TFA in water: Acetonitrile (95:5). Mobile Phase B: Acetonitrile: 0.05% TFA in water (95:5). Flow: 1.0 ml/min. Wavelength: 254 nm. Rt min: 10.79. Wavelength: 220 nm. Rt min: 10.79.

HPLC Method: SUNFIRE C18 (150×4.6 mm) 3.5 micron

| Time | B % |
| --- | --- |
| 0 | 10 |
| 25 | 100 |
| 30 | 100 |

HPLC Method:)(Bridge Phenyl (150×4.6 mm) 3.5 micron

| Time | B % |
| --- | --- |
| 0 | 10 |
| 12 | 100 |
| 15 | 100 |

Example 28

5-(3-((2-cyanopropan-2-yl)carbamoyl)-4-(methoxy-d₃)phenyl)-6-ethoxy-2-(4-fluorophenyl)-N-methylbenzofuran-3-carboxamide

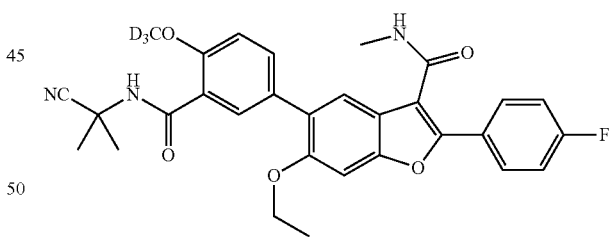

To a solution of 5-(6-ethoxy-2-(4-fluorophenyl)-3-(methylcarbamoyl)benzofuran-5-yl)-2-(methoxy-d₃)benzoic acid (0.04 g, 0.086 mmol), DIPEA (0.045 mL, 0.257 mmol) and HATU (0.033 g, 0.086 mmol) in DMF (4 mL) at 0° C. was added 2-amino-2-methylpropanenitrile hydrochloride (0.012 g, 0.103 mmol). The reaction mixture was stirred at 25° C. for 4 hours. The reaction mixture was diluted with ice-cold water, the solid filtered and dried under suction. The crude product was submitted for reverse phase prep HPLC purification to obtain 5-(3-((2-cyanopropan-2-yl)carbamoyl)-4-(methoxy-d₃)phenyl)-6-ethoxy-2-(4-fluorophenyl)-N-methylbenzofuran-3-carboxamide. Preparative HPLC Method: Inertsil ODS (250×4.6 mm, 5 um). Mobile phase A: 10 mM Ammonium Acetate in Water pH 4.6 adjusted with acetic acid. Mobile phase B: MeCN. Flow: 1.0 ml/min. Rt: 15.97 min. wavelength. $^1$H NMR (400 MHz, METHANOL-$d_4$) δ ppm 8.09 (d, J=2.38 Hz, 1H), 7.96-7.92 (m, 2H), 7.75 (dd, J=8.63, 2.42 Hz, 1H), 7.56 (s, 1H), 7.31 (s, 1H), 7.27-7.22 (m, 3H), 4.15 (q, J=6.96 Hz, 2H), 2.97 (s, 3H), 1.82 (s, 6H) 1.39 (t, J=6.96 Hz, 3H). $^{19}$F NMR (376.6 MHz, METHANOL-$d_4$): δ ppm=-113.40. LCMS: (ES+) m/z=533.4 (M+H)$^+$. Column-ACQUITY UPLC BEH C8 (50×2.1 mm; 1.7 μm). Buffer: 10 mM AmmoniumAcetate pH-5 adjusted with HCOOH. M phase A: Buffer:MeCN (95:5). M phase B: Buffer:MeCN (5:95). Flow: 0.8 ml/min., Method: % B: 0 min-5%:1.1 min-95%:1.7 min-95%. Rt min: 1.11, wavelength: 220 nm., and gradient:

| Time | % A | % B |
|---|---|---|
| 0 | 95 | 5 |
| 1.1 | 5 | 95 |
| 1.7 | 5 | 95 |

HPLC Method: COLUMN: SUNFIRE C18 (150×4.6 mm) 3.5 micron. Mobile Phase A: 0.05% TFA in Water: Acetonitrile (95:5). Mobile Phase B: Acetonitrile: 0.05% TFA in Water (95:5). Flow: 1.0 ml/min. Wavelength: 254 nm, Rt min: 20.28. Wavelength: 220 nm, Rt min: 20.28. HPLC Method:)(Bridge Phenyl (150×4.6 mm) 3.5 micron. Mobile Phase A: 0.05% TFA in water: Acetonitrile (95:5). Mobile Phase B: Acetonitrile: 0.05% TFA in water (95:5) Flow: 1.0 ml/min. Wavelength: 254 nm. Rt min: 10.91. Wavelength: 220 nm. Rt min: 10.91.

HPLC Method: SUNFIRE C18 (150×4.6 mm) 3.5 micron.

| Time | B % |
|---|---|
| 0 | 10 |
| 25 | 100 |
| 30 | 100 |

HPLC Method:)(Bridge Phenyl (150×4.6 mm) 3.5 micron

| Time | B % |
|---|---|
| 0 | 10 |
| 12 | 100 |
| 15 | 100 |

Example 29

5-(2-(4-Fluorophenyl)-3-(methylcarbamoyl)-6-(2,2,2-trifluoroethoxy)benzofuran-5-yl)-2-methoxy-N-(1-(pyrimidin-2-yl)cyclopropyl)nicotinamide

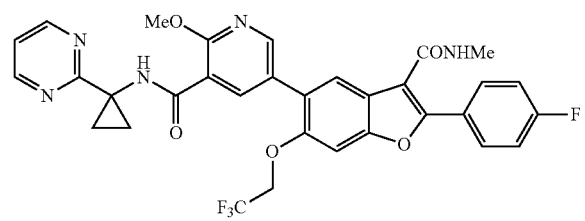

To a stirred mixture of 5-(2-(4-fluorophenyl)-3-(methylcarbamoyl)-6-(2,2,2-trifluoroethoxy)benzofuran-5-yl)-2-methoxynicotinic acid (25 mg, 0.048 mmol), 1-(pyrimidin-2-yl)cyclopropanamine, HCl (8.28 mg, 0.048 mmol) in DMF (2 ml) at 10° C. was added DIPEA (0.033 mL, 0.193 mmol) and HATU (21.99 mg, 0.058 mmol). The mixture was stirred at room temperature for 3 hr. After completion of the reaction, ice-cold water was added to the reaction mixture, and the solid precipitated out was filtered. The crude product and purified by preparative TLC using CHCl$_3$: MeOH (9:1) to afford 5-(2-(4-fluorophenyl)-3-(methylcarbamoyl)-6-(2,2,2-trifluoroethoxy)benzofuran-5-yl)-2-methoxy-N-(1-(pyrimidin-2-yl)cyclopropyl)nicotinamide. Yield: 16 mg (53%). $^1$H NMR (400 MHz, METHANOL-$d_4$) δ ppm 1.50-1.59 (m, 2H), 1.76-1.88 (m, 2H), 2.97 (s, 3H), 4.21 (s, 3H), 4.68 (q, J=8.37 Hz, 2H), 7.16-7.33 (m, 3H), 7.51 (s, 1H), 7.68 (s, 1H), 7.96 (dd, J=9.04, 5.27 Hz, 2H), 8.47-8.57 (m, 2H), 8.67 (d, J=4.96 Hz, 2H), $^{19}$F NMR (376.6 MHz, METHANOL-$d_4$) δ ppm: -112.81 and -75.34. LCMS: (ES+) m/z=636.8 (M+H)$^+$, Column-Ascentis Express C18 (50×2.1 mm-2.7 μm), M phase A: 2% MeCN-98% H$_2$O-10 mM NH$_4$COOH, M phase B: 98% MeCN-2% H$_2$O-10 mM NH$_4$COOH, Flow=1 mL/min, Time (min.): Rt min: 2.28, wavelength: 220 nm.

| Time | % B |
|---|---|
| 0.0 | 0.0 |
| 1.7 | 100.0 |
| 3.0 | 100.0 |
| 3.2 | 0.0 |

HPLC Method: SUNFIRE (150×4.6 mm) 3.5 micron, Buffer: 0.05% TFA in water pH 2.5, Mobile Phase A: Buffer:MeCN (95:5), Mobile Phase B: MeCN: Buffer (95:5), Flow: 1.0 ml/min, Wavelength: 254 nm, Rt: 18.55 min, Wavelength: 220 nm, Rt: 18.55 min. HPLC Method:)(Bridge Phenyl (150×4.6 mm) 3.5 micron SC/749, Buffer: 0.05% TFA in water pH 2.5, Mobile Phase A: Buffer:MeCN (95:5), Mobile Phase B: Buffer:MeCN (5:95), Flow: 1.0 ml/min, Wavelength: 254 nm, Rt: 16.34 min, Wavelength: 220 nm, Rt: 16.34 min.

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 30

N-(Bicyclo[1.1.1]pentan-1-yl)-5-(2-(4-fluorophenyl)-3-(methylcarbamoyl)-6-(2,2,2-trifluoroethoxy)benzofuran-5-yl)-2-methoxynicotinamide

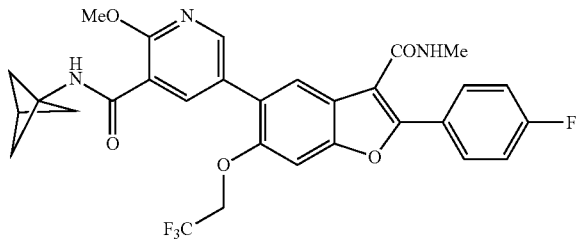

To a stirred solution of 5-(2-(4-fluorophenyl)-3-(methylcarbamoyl)-6-(2,2,2-trifluoroethoxy)benzofuran-5-yl)-2-methoxynicotinic acid (25 mg, 0.048 mmol), bicyclo[1.1.1]pentan-1-amine, HCl (5.77 mg, 0.048 mmol) in DMF (2 ml) was added DIPEA (0.033 mL, 0.193 mmol) and HATU (21.99 mg, 0.058 mmol). The mixture was stirred at room temperature for overnight. After completion of the reaction ice-cold water was added to the reaction mixture. The solid precipitated out was filtered and purified by preparative TLC using CHCl$_3$:MeOH (9:1) to afford N-(bicyclo[1.1.1]pentan-1-yl)-5-(2-(4-fluorophenyl)-3-(methylcarbamoyl)-6-(2,2,2-trifluoroethoxy)benzofuran-5-yl)-2-methoxynicotinamide. Yield: 6.0 mg (21%). $^1$H NMR (400 MHz, METHANOL-d$_4$) δ ppm 2.23 (s, 6H), 2.52 (s, 1H), 2.97 (s, 3H), 4.15 (s, 3H), 4.68 (q, J=8.4 Hz, 2H), 7.25-7.29 (m, 2H), 7.50 (s, 1H), 7.66 (s, 1H), 7.94-7.98 (m, 2H), 8.395 (d, J=2.8 Hz, 1H), 8.473 (d, J=2.4 Hz, 1H), $^{19}$F NMR (376.6 MHz, METHANOL-d$_4$) δ ppm: −112.80 and −75.38, LCMS: (ES+) m/z=584.2 (M+H)$^+$, Column-Ascentis Express C18 (50×2.1 mm-2.7 μm), M phase A: 2% MeCN-98% H$_2$O-10 mM NH$_4$COOH, M phase B: 98% MeCN-2% H$_2$O-10 mM NH$_4$COOH, Flow=1 ml/min, Time (min.): RT min: 2.31, wavelength: 220 nm.

| Time | % B |
|---|---|
| 0.0 | 0.0 |
| 1.7 | 100.0 |
| 3.4 | 100.0 |

HPLC Method: SUNFIRE (150×4.6 mm) 3.5 micron, Buffer: 0.05% TFA in water pH 2.5, Mobile Phase A: Buffer:MeCN (95:5), Mobile Phase B: MeCN: Buffer (95:5), Flow: 1.0 ml/min, Wavelength: 254 nm, Rt: 21.75 min, Wavelength: 220 nm, Rt: 21.75 min. HPLC Method:)(Bridge Phenyl (150×4.6 mm) 3.5 micron, SC/749, Buffer: 0.05% TFA in water pH 2.5, Mobile Phase A: Buffer:MeCN (95:5), Mobile Phase B: Buffer:MeCN (5:95), Flow: 1.0 ml/min, Wavelength: 254 nm, Rt: 18.35 min, Wavelength: 220 nm, Rt: 18.35 min.

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 31

N-(2-(1,2,4-Oxadiazol-3-yl)propan-2-yl)-5-(2-(4-fluorophenyl)-3-(methylcarbamoyl)-6-(2,2,2-trifluoroethoxy)benzofuran-5-yl)-2-methoxynicotinamide

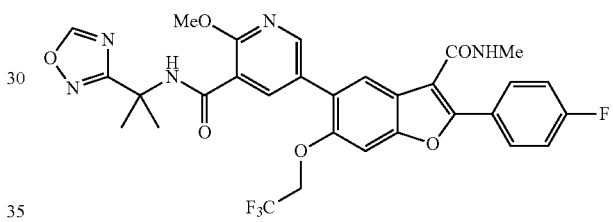

N-(2-(1,2,4-Oxadiazol-3-yl)propan-2-yl)-5-(2-(4-fluorophenyl)-3-(methylcarbamoyl)-6-(2,2,2-trifluoroethoxy)benzofuran-5-yl)-2-methoxynicotinamide was prepared from the coupling of 5-(2-(4-fluorophenyl)-3-(methylcarbamoyl)-6-(2,2,2-trifluoroethoxy)benzofuran-5-yl)-2-methoxynicotinic acid with 2-(1,2,4-oxadiazol-3-yl)propan-2-amine hydrochloride in a similar manner as described for 5-(2-(4-fluorophenyl)-3-(methylcarbamoyl)-6-(2,2,2-trifluoroethoxy)benzofuran-5-yl)-2-methoxy-N-(1-(pyrimidin-2-yl)cyclopropyl)nicotinamide. $^1$H NMR (400 MHz, METHANOL-d$_4$) δ ppm 9.18 (s, 1H), 8.50 (d, J=2.4 Hz, 1H), 8.39 (d, J=2.8 Hz, 1H), 7.97-7.94 (m, 2H), 7.65 (s, 1H), 7.49 (s, 1H), 7.29-7.25 (m, 2H), 4.67 (q, J=8.4 Hz, 2H), 4.21 (s, 3H), 2.96 (s, 3H), 1.86 (s, 6H), $^{19}$F NMR (376.6 MHz, METHANOL-d$_4$) δ ppm: −112.80 and −75.38. LCMS: (ES+) m/z observed=629.2 (M+H)$^+$, Column-Ascentis Express C18 (50×2.1 mm-2.7 μm), M phase A: 2% MeCN-98% H$_2$O-10 mM NH$_4$COOH, M phase B: 98% MeCN-2% H$_2$O-10 mM NH$_4$COOH, Flow=1 mL/min, Time (min.): Rt min: 2.22, wavelength: 254 nm.

| Time | % B |
|---|---|
| 0.0 | 0.0 |
| 1.7 | 100.0 |
| 3.4 | 100.0 |

HPLC Method: SUNFIRE (150×4.6 mm) 3.5 micron, Buffer: 0.05% TFA in water pH 2.5, Mobile Phase A: Buffer:MeCN (95:5), Mobile Phase B: MeCN: Buffer (95:

5), Flow: 1.0 ml/min, Wavelength: 254 nm, Rt: 19.79 min, Wavelength: 220 nm, Rt: 19.79 min. HPLC Method:) (Bridge Phenyl (150×4.6 mm) 3.5 micron SC/749, Buffer: 0.05% TFA in water pH 2.5, Mobile Phase A: Buffer:MeCN (95:5), Mobile Phase B: Buffer:MeCN (5:95), Flow: 1.0 ml/min, Wavelength: 254 nm, Rt: 17.38 min, Wavelength: 220 nm, Rt: 17.38 min.

HPLC Method: SUNFIRE C18 (150×4.6 mm) 3.5 micron

| Time | B % |
| --- | --- |
| 0 | 10 |
| 25 | 100 |
| 30 | 100 |

HPLC Method:)(Bridge Phenyl (150×4.6 mm) 3.5 micron SC/749

| Time | B % |
| --- | --- |
| 0 | 10 |
| 25 | 100 |
| 30 | 100 |

Example 32

5-(3-((2-(3H-imidazo[4,5-c]pyridin-2-yl)propan-2-yl)carbamoyl)phenyl)-6-ethoxy-2-(4-fluorophenyl)-N-methylbenzofuran-3-carboxamide

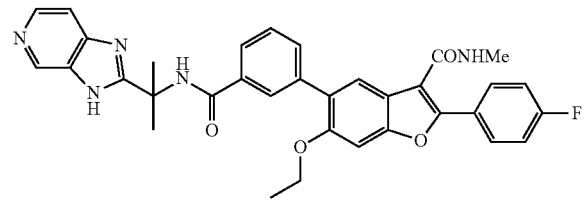

To a stirred solution of 3-(6-ethoxy-2-(4-fluorophenyl)-3-(methylcarbamoyl)benzofuran-5-yl)benzoic acid (40 mg, 0.092 mmol), 2-(3H-imidazo[4,5-c]pyridin-2-yl)propan-2-amine (16.26 mg, 0.092 mmol, assumed free base) in DMF (3 mL) at 10° C. was added DIPEA (47.6 mg, 0.369 mmol) followed by HATU (0.00 mg, 0.111 mmol). The resulting reaction mixture was stirred at room temperature for overnight. After completion of the reaction, the mixture was poured into ice-cold water. The solid precipitated out was filtered, and purified by Preparative HPLC to afford 5-(3-((2-(3H-imidazo[4,5-c]pyridin-2-yl)propan-2-yl)carbamoyl)phenyl)-6-ethoxy-2-(4-fluorophenyl)-N-methylbenzofuran-3-carboxamide. Preparative HPLC method: Column dimensions:Inertsil ods (20 mm*250 mm) 5 um, Mobile phase A: 0.1% TFA, Mobile phase B: MeCN, Flow: 18 ml/min Rt=7.7 min. Yield: 12 mg. $^1$H NMR (400 MHz, DMSO-$d_6$) δ ppm 13.71 (bs, 1H), 9.34 (bs, 1H), 8.94 (s, 1H), 8.51 (d, J=6.40 Hz, 1H), 8.43-8.41 (m, 1H), 8.04 (s, 1H), 7.95-7.92 (m, 3H), 7.87 (d, J=8.00 Hz, 1H), 7.71 (d, J=8.00 Hz, 1H), 7.54-7.50 (m, 1H), 7.52 (s, 1H), 7.47 (s, 1H), 7.40-7.35 (m, 2H), 4.15 (q, J=6.96 Hz, 2H), 2.82 (d, J=4.58 Hz, 3H), 1.82 (s, 6H), 1.29 (t, J=6.93 Hz, 3H). $^{19}$F NMR (376.6 MHz, DMSO-$d_6$) δ ppm: −73.49. LCMS: (ES+) m/z=592.2 (M+H)$^+$, Column-Ascentis Express C18 (50×2.1 mm-2.7 μm), M phase A: 2% MeCN-98% H$_2$O-10 mM NH$_4$COOH, M phase B: 98% MeCN-2% H$_2$O-10 mM NH$_4$COOH, Flow=1 mL/min, Time (min.): Rt min: 2.03, wavelength: 220 nm.

| Time | % B |
| --- | --- |
| 0.0 | 0.0 |
| 1.7 | 100.0 |
| 3.4 | 100.0 |

HPLC Method: SUNFIRE (150×4.6 mm) 3.5 micron, Buffer: 0.05% TFA in water pH 2.5, Mobile Phase A: Buffer:MeCN (95:5), Mobile Phase B: MeCN: Buffer (95:5), Flow: 1.0 ml/min, Wavelength: 254 nm, Rt: 7.39 min, Wavelength: 220 nm, Rt: 7.39 min. HPLC Method:)(Bridge Phenyl (150×4.6 mm) 3.5 micron, Buffer: 0.05% TFA in water pH 2.5, Mobile Phase A: Buffer:MeCN (95:5), Mobile Phase B: Buffer:MeCN (5:95), Flow: 1.0 ml/min, Wavelength: 254 nm, Rt: 8.32 min, Wavelength: 220 nm, Rt: 8.32 min.

HPLC Method: SUNFIRE C18 (150×4.6 mm) 3.5 micron

| Time | B % |
| --- | --- |
| 0 | 10 |
| 12 | 100 |
| 15 | 100 |

HPLC Method:)(Bridge Phenyl (150×4.6 mm) 3.5 micron

| Time | B % |
| --- | --- |
| 0 | 10 |
| 12 | 100 |
| 15 | 100 |

Example 33

5-(3-((2-(1,2,4-thiadiazol-3-yl)propan-2-yl)carbamoyl)-4-(methoxy-$d_3$)phenyl)-6-ethoxy-2-(4-fluorophenyl)-N-methylbenzofuran-3-carboxamide

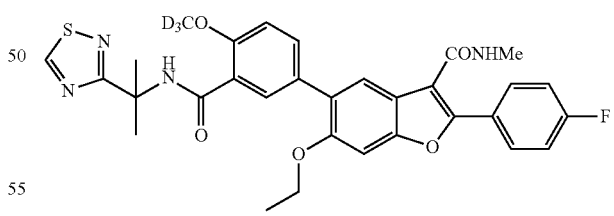

To a stirred solution of 5-(6-ethoxy-2-(4-fluorophenyl)-3-(methylcarbamoyl)benzofuran-5-yl)-2-(methoxy-$d_3$)benzoic acid (25 mg, 0.054 mmol) and 2-(1,2,4-thiadiazol-3-yl)propan-2-amine hydrobromide (50 mg, 0.223 mmol) in DMF (2 mL) was added DIPEA (0.037 mL, 0.214 mmol) and HATU (0.00 mg, 0.080 mmol). The mixture was stirred at room temperature for 4 hr. After completion of the reaction, the mixture was poured into ice-cold water. The solid obtained was filtered and dried, and then purified by Preparative HPLC to afford 5-(3-((2-(1,2,4-thiadiazol-3-yl)

propan-2-yl)carbamoyl)-4-(methoxy-d₃)phenyl)-6-ethoxy-2-(4-fluorophenyl)-N-methylbenzofuran-3-carboxamide. Preparative HPLC method: Preparative column dimensions: Sunfire C-18 (19*150 mm) 5 um, Mobile phase A: 10 mM Ammonium acetate, Mobile phase B: Acetonitrile, Flow: 16.0 ml/min, Gradient: T(min)/% B: 0/30, 10/90, Rt=10.18 min. Yield: 10 mg (31%). ¹H NMR (400 MHz, DMSO-d₆) δ ppm: 10.22 (s, 1H), 9.11 (s, 1H), 8.42-8.41 (m, 1H), 7.97-7.92 (m, 3H), 7.68-7.65 (m, 1H), 7.43 (d, J=4.0 Hz, 2H), 7.40-7.34 (m, 2H), 7.24 (d, J=8.4 Hz, 1H), 4.13 (q, J=7.01 Hz, 2H), 2.81 (d, J=4.4 Hz, 3H), 1.80 (s, 6H), 1.27 (t, J=6.96 Hz, 3H). ¹⁹F NMR (376.6 MHz, DMSO-d₆) δ ppm: −111.54. LCMS: (ES+) m/z=592.2 (M+H)⁺, Column-Ascentis Express C18 (50×2.1 mm) 2.7 um, M phase A: 2% MeCN-98% H₂O-10 mM NH₄COOH, M phase B: 98% MeCN-2% H₂O-10 mM NH₄COOH, Flow: 1.0 ml/min. Rt: 2.31 min, wavelength: 220 nm.

| Time | % A | % B |
|---|---|---|
| 0.0 | 100 | 0.0 |
| 1.7 | 0.0 | 100.0 |
| 3.4 | 0.0 | 100.0 |

HPLC Method: SUNFIRE (150×4.6 mm) 3.5 micron, Buffer: 0.05% TFA in water, Mobile Phase A: Buffer:MeCN (95:5), Mobile Phase B: MeCN: Buffer (95:5), Flow: 1.0 ml/min, Wavelength: 254 nm, Rt: 20.61 min, Wavelength: 220 nm, Rt: 20.61 min. HPLC Method:)(Bridge Phenyl (150×4.6 mm) 3.5 micron SC/749, Buffer: 0.05% TFA in water, Mobile Phase A: Buffer:MeCN (95:5), Mobile Phase B: Buffer:MeCN (5:95), Flow: 1.0 ml/min, Wavelength: 254 nm, Rt: 17.83 min, Wavelength: 220 nm, Rt: 17.83 min.

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Example 34

5-(3-((2-(1,2,4-Oxadiazol-3-yl)propan-2-yl)carbamoyl)-4-methoxyphenyl)-2-(4-fluorophenyl)-6-(2-hydroxyethoxy)-N-methylbenzofuran-3-carboxamide

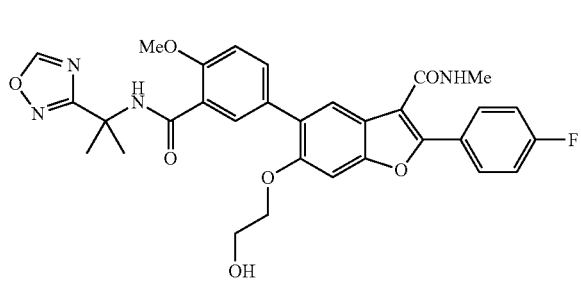

5-(3-((2-(1,2,4-Oxadiazol-3-yl)propan-2-yl)carbamoyl)-4-methoxyphenyl)-2-(4-fluorophenyl)-6-(2-hydroxyethoxy)-N-methylbenzofuran-3-carboxamide was prepared in a manner similar to that described in Scheme 6. ¹H NMR (400 MHz, DMSO-d₆) δ ppm 9.46 (s, 1H), 8.62 (s, 1H), 8.43-8.39 (m, 1H), 7.96-7.92 (m, 2H), 7.87 (d, J=2.4 Hz, 1H), 7.74 (dd, J=8.6, 2.4 Hz, 1H), 7.45 (d, J=9.6 Hz, 2H), 7.38-7.34 (m, 2H), 7.22 (d, J=8.8 Hz, 1H), 4.78-4.75 (m, 1H), 4.11-4.09 (m, 2H), 3.99 (s, 3H), 3.71-3.67 (m, 2H), 2.81 (d, J=4.80 Hz, 3H), 1.72 (s, 6H), ¹⁹F NMR (376.6 MHz, DMSO-d₆) δ ppm: −111.52. LCMS: (ES+) m/z observed=589.2 (M+H)⁺, Column-Ascentis Express C18 (50×2.1 mm-2.7 μm), M phase A: 0.1% HCOOH in water, M phase B: MeCN, Flow=1 mL/min, Time (min.): Rt min: 2.05, wavelength: 220 nm.

| Time | % B |
|---|---|
| 0.0 | 0.0 |
| 1.7 | 100.0 |
| 3.2 | 100.0 |

HPLC Method: SUNFIRE (150×4.6 mm) 3.5 micron, Buffer: 0.05% TFA in water, Mobile Phase A: Buffer:MeCN (95:5), Mobile Phase B: MeCN: Buffer (95:5), Flow: 1.0 ml/min, Wavelength: 254 nm, Rt: 15.64 min, Wavelength: 220 nm, Rt: 15.64 min. HPLC Method:)(Bridge Phenyl (150×4.6 mm) 3.5 micron SC/749, Buffer: 0.05% TFA in water, Mobile Phase A: Buffer:MeCN (95:5), Mobile Phase B: Buffer:MeCN (5:95), Flow: 1.0 ml/min, Wavelength: 254 nm, Rt: 14.28 min, Wavelength: 220 nm, Rt: 14.28 min.

HPLC Method: SUNFIRE C18 (150×4.6 mm) 3.5 micron

| Time | B % |
|---|---|
| 0 | 10 |
| 25 | 100 |
| 30 | 100 |

HPLC Method:)(Bridge Phenyl (150×4.6 mm) 3.5 micron SC/749

| Time | B % |
|---|---|
| 0 | 10 |
| 25 | 100 |
| 30 | 100 |

Biological Methods

HCV NS5B RdRp Cloning, Expression, and Purification.

The cDNA encoding NS5B proteins of HCV genotype 1b (Con1), a genotype 1b variant with amino acid 316 mutated from cysteine to asparagine, and genotype 2a (JFH-1), were cloned into the pET21a expression vector. Each untagged protein was expressed with an 18 amino acid C-terminal truncation to enhance the solubility. The *E. coli* competent cell line BL21(DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/mL and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/mL lysozyme, 10 mM $MgCl_2$, 15 ug/mL deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 30 minutes at 4° C. and filtered through a 0.2 µm filter unit (Corning).

The protein was purified using two sequential chromatography steps: Heparin sepharose CL-6B and polyU sepharose 4B. The chromatography buffers were identical to the lysis buffer but contained no lysozyme, deoxyribonuclease I, $MgCl_2$ or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

HCV NS5B RdRp Enzyme Assay.

An on-bead solid phase homogeneous assay was used in a 384-well format to assess NS5B inhibitors (WangY-K, Rigat K, Roberts S, and Gao M (2006) Anal Biochem, 359: 106-111). The biotinylated oligo $dT_{12}$ primer was captured on streptavidin-coupled imaging beads (GE, RPNQ0261) by mixing primer and beads in 1× buffer and incubating at room temperature for three hours. Unbound primer was removed after centrifugation. The primer-bound beads were resuspended in 3× reaction mix (20 mM Hepes buffer, pH 7.5, dT primer coupled beads, poly A template, $^3$H-UTP, and RNAse inhibitor (Promega N2515)). Compounds were serially diluted 1:3 in DMSO and aliquoted into assay plates. Equal volumes (5 µL) of water, 3× reaction mix, and enzyme in 3× assay buffer (60 mM Hepes buffer, pH 7.5, 7.5 mM $MgCl_2$, 7.5 mM KCl, 3 mM DTT, 0.03 mg/mL BSA, 6% glycerol) were added to the diluted compound on the assay plate. Final concentration of components in 384-well assay: 0.36 nM template, 15 nM primer, 0.29 µM $^3$H-UTP (0.3 µCi), 1.6 U/4 RNAse inhibitor, 7 nM NS5B enzyme, 0.01 mg/mL BSA, 1 mM DTT, and 0.33 µg/µL beads, 20 mM Hepes buffer, pH 7.5, 2.5 mM $MgCl_2$, 2.5 mM KCl, and 0.1% DMSO.

Reactions were allowed to proceed for 24 hours at 30° C. and terminated by the addition of 50 mM EDTA (5 µL). After incubating for at least 15 minutes, plates were read on an Amersham LEADseeker multimodality imaging system.

$IC_{50}$ values for compounds were determined using ten different [I]. $IC_{50}$ values were calculated from the inhibition using the four-parameter logistic formula $y=A+((B-A)/(1+((C/x)^D)))$, where A and B denote minimal and maximal % inhibition, respectively, C is the $IC_{50}$, D is hill slope and x represents compound concentration.

Cell Lines.

The cell lines used to evaluate compounds consist of a human hepatocyte derived cell line (Huh-7) that constitutively expresses a genotype 1b (Con-1) HCV replicon or a genotype 1b (Con-1) HCV replicon with an asparagine replacing the cysteine at amino acid 316, or a genotype 2a (JFH-1) replicon, containing a Renilla luciferase reporter gene. These cells were maintained in Dulbecco's modified Eagle medium (DMEM) containing 10% FBS, 100 U/mL penicillin/streptomycin and 1.0 mg/mL G418.

HCV Replicon Luciferase Assay.

To evaluate compound efficacy, titrated compounds were transferred to sterile 384-well tissue culture treated plates, and the plates were seeded with HCV replicon cells (50 µL at a density of $2.4\times10^3$ cells/well) in DMEM containing 4% FBS (final DMSO concentration at 0.5%). After 3 days incubation at 37° C., cells were analyzed for *Renilla* Luciferase activity using the EnduRen substrate (Promega cat #E6485) according to the manufacturer's directions. Briefly, the EnduRen substrate was diluted in DMEM and then added to the plates to a final concentration of 7.5 µM. The plates were incubated for at least 1 h at 37° C. then read on a Viewlux Imager (PerkinElmer) using a luminescence program. The 50% effective concentration ($EC_{50}$) was calculated using using the four-parameter logistic formula noted above.

To assess cytotoxicity of compounds, Cell Titer-Blue (Promega) was added to the EnduRen-containing plates and incubated for at least 4 h at 37° C. The fluorescence signal from each well was read using a Viewlux Imager. All $CC_{50}$ values were calculated using the four-parameter logistic formula.

1b enzyme and replicon data for the Examples are reported in Table 2.

TABLE 2

| Example | Structure | IC$_{50}$ (µM) | EC$_{50}$ (µM) |
| --- | --- | --- | --- |
| Example 1 | 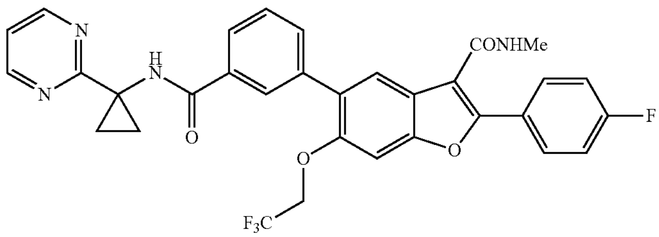 | 7.42E−03 | 0.01 |
| Example 2 | 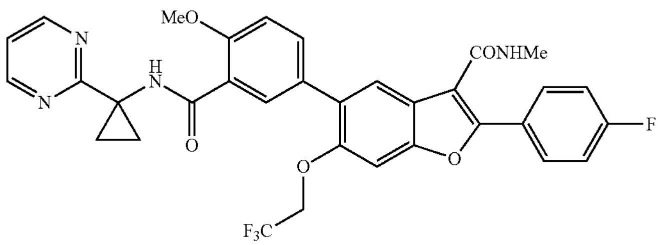 | 4.15E−03 | 6.24E−03 |
| Example 3 | 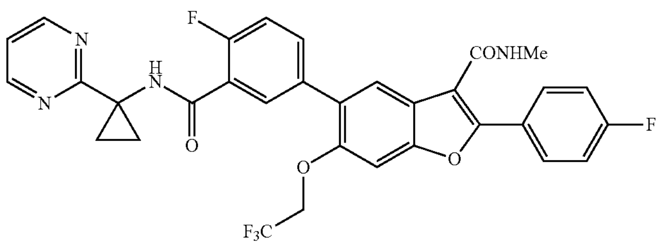 | 4.38E−03 | 6.70E−03 |
| Example 4 | 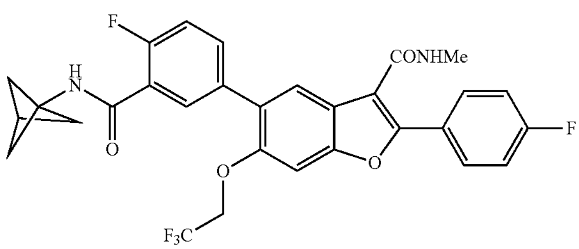 | 3.88E−03 | 8.61E−03 |
| Example 5 | 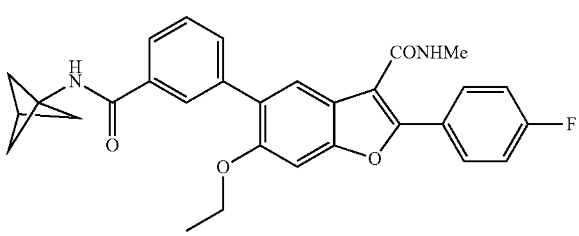 | 4.30E−03 | 6.50E−03 |
| Example 6 | 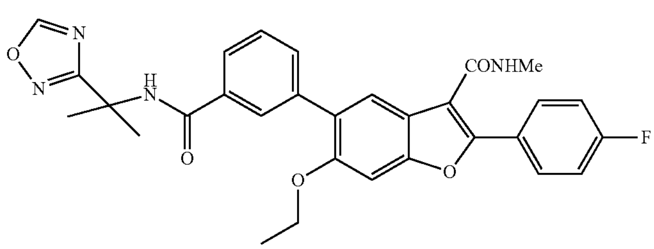 | 3.31E−03 | 6.88E−03 |

TABLE 2-continued

| Example | Structure | IC$_{50}$ (µM) | EC$_{50}$ (µM) |
|---|---|---|---|
| Example 7 | 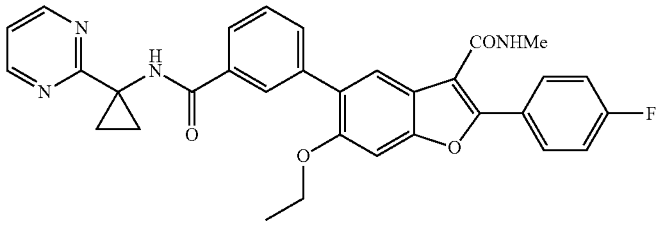 | 5.78E−03 | 0.01 |
| Example 8 | 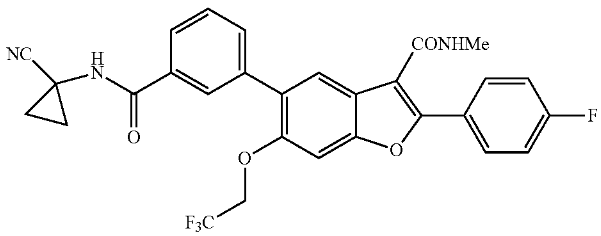 | 4.97E−03 | 0.02 |
| Example 9 | 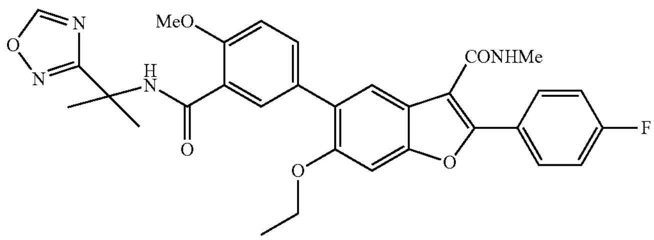 | 6.03E−04 | 1.97E−03 |
| Example 10 | 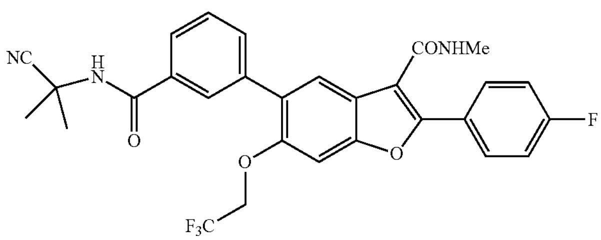 | 3.02E−03 | 5.01E−03 |
| Example 11 | 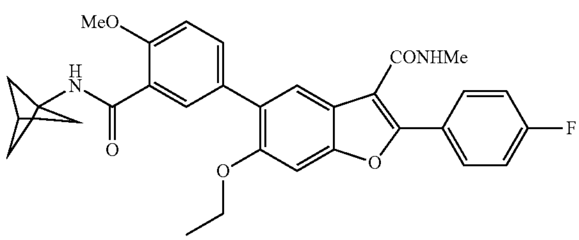 | | 9.63E−03 |
| Example 12 | 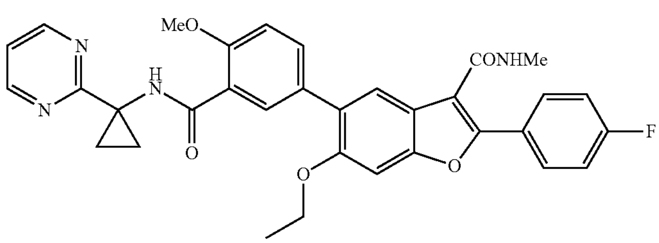 | 1.89E−03 | 4.20E−03 |

TABLE 2-continued

| Example | Structure | IC$_{50}$ (µM) | EC$_{50}$ (µM) |
|---|---|---|---|
| Example 13 | 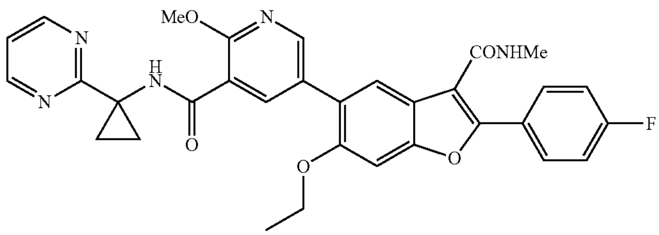 | 2.72E−03 | 3.67E−03 |
| Example 14 | 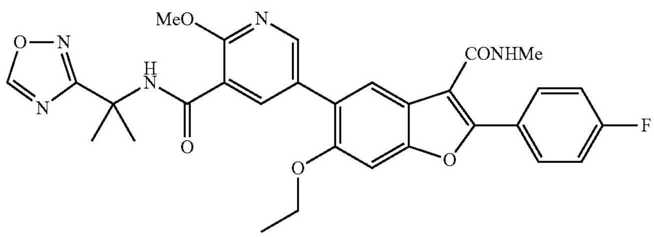 | 1.52E−03 | 3.20E−03 |
| Example 15 | 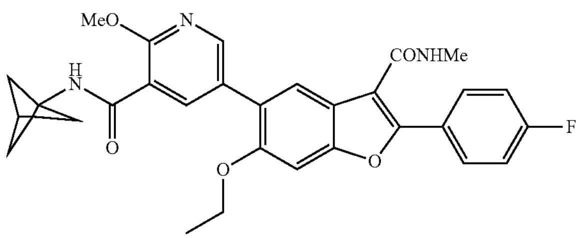 | 2.48E−03 | 7.03E−03 |
| Example 16 | 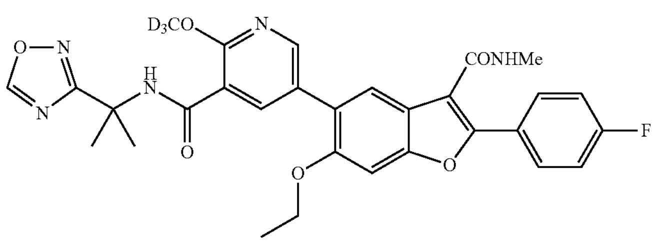 | 2.73E−03 | 2.95E−03 |
| Example 17 | 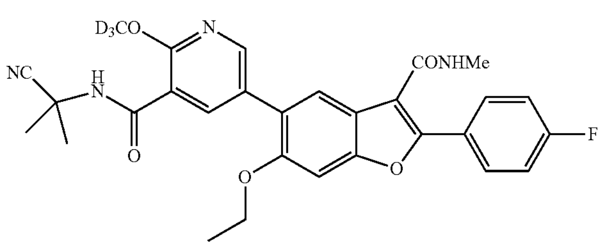 | 1.84E−03 | 2.80E−03 |
| Example 18 | 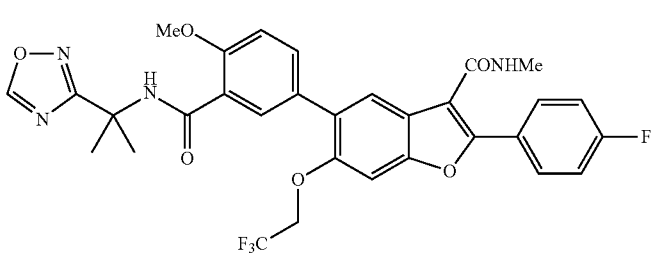 | 2.83E−03 | 2.85E−03 |

TABLE 2-continued

| Example | Structure | IC$_{50}$ (µM) | EC$_{50}$ (µM) |
| --- | --- | --- | --- |
| Example 19 | 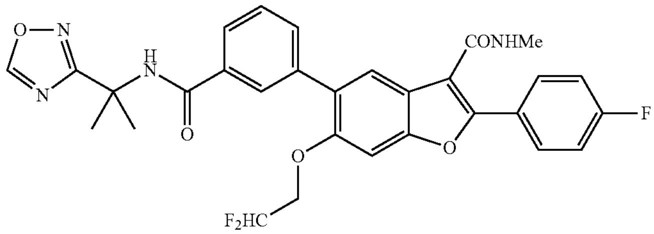 | 4.20E−03 | 7.41E−03 |
| Example 20 | 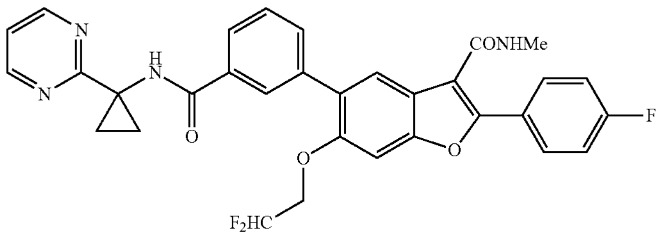 | 4.54E−03 | 6.79E−03 |
| Example 21 | 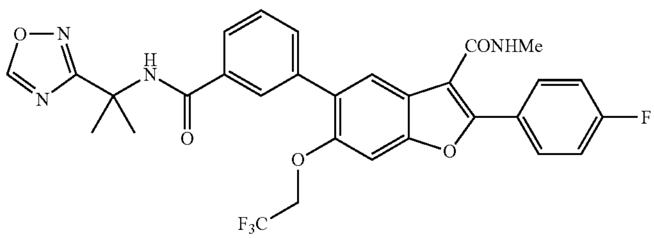 | 4.49E−03 | 0.01 |
| Example 22 | 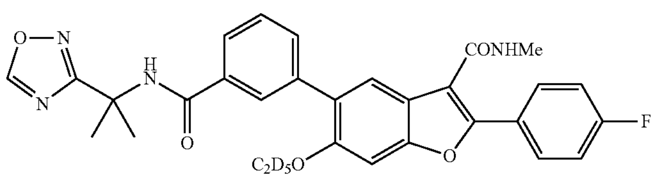 | 5.05E−03 | 8.36E−03 |
| Example 23 | 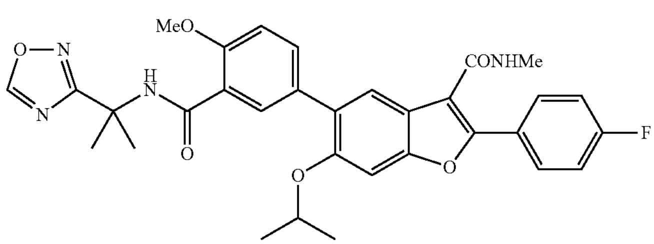 | 7.14E−03 | 0.01 |
| Example 24 | 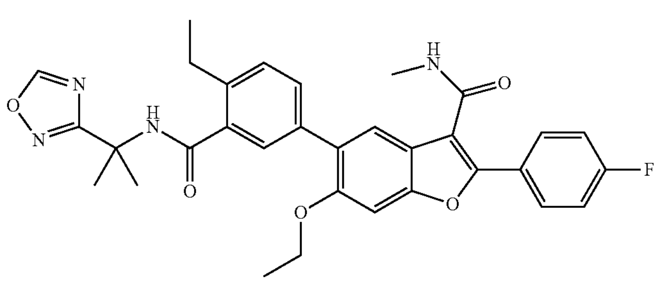 [SMILES: CCOc1cc2oc(-c3ccc(F)cc3)c(C(=O)NC)c2cc1-c1ccc(CC)c(C(=O)NC(C)(C)c2ncon2)c1] | >2.5 | 0.28 |

TABLE 2-continued
| Example | Structure | IC$_{50}$ (μM) | EC$_{50}$ (μM) |
|---|---|---|---|
| Example 25 | 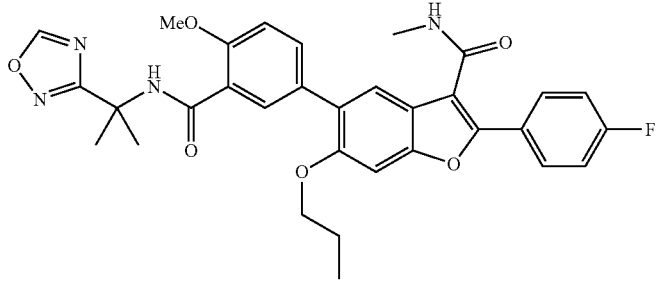 [SMILES: CCCOc1cc2oc(-c3ccc(F)cc3)c(C(=O)NC)c2cc1-c1ccc(OC)c(C(=O)NC(C)(C)c2ncon2)c1] | 2.48E−03 | 6.23E−03 |
| Example 26 | 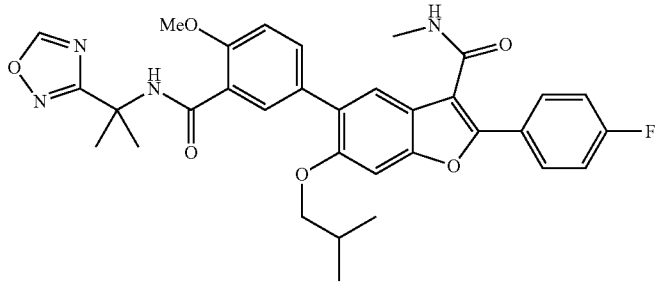 [SMILES: CNC(=O)c1c(-c2ccc(F)cc2)oc2cc(OCC(C)C)c(-c3ccc(OC)c(C(=O)NC(C)(C)c4ncon4)c3)cc12] | 0.03 | 0.08 |
| Example 27 | 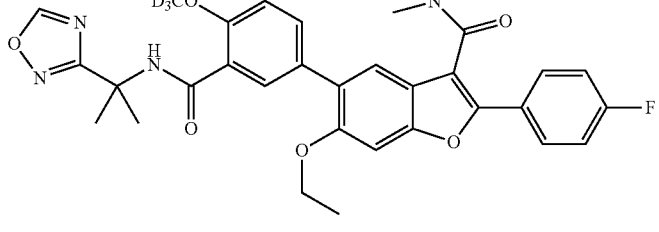 | 2.22E−03 | 2.38E−03 |
| Example 28 | 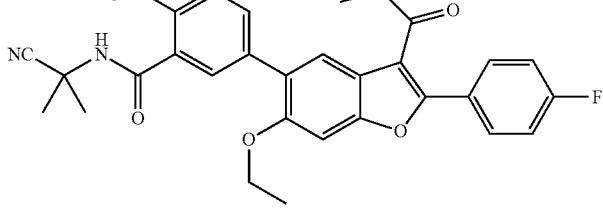 | 2.04E−03 | 2.01E−03 |
| Example 29 | 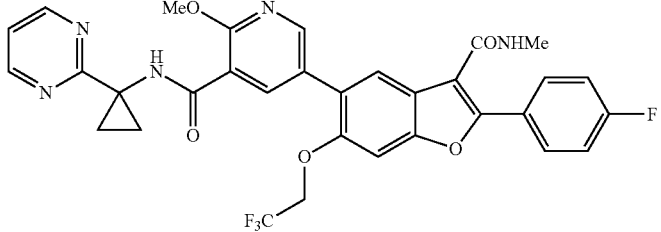 | 2.95E−03 | 4.57E−03 |
| Example 30 | 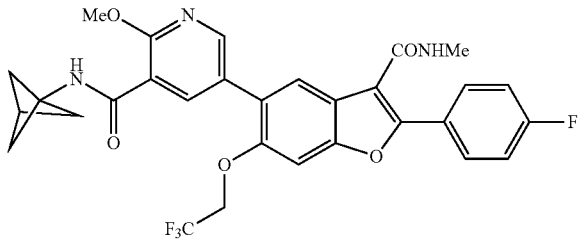 |  | 0.01 |

TABLE 2-continued

| Example | Structure | IC$_{50}$ (μM) | EC$_{50}$ (μM) |
|---|---|---|---|
| Example 31 | 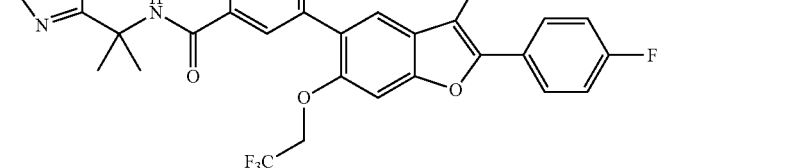 | | 3.21E−03 |
| Example 32 | 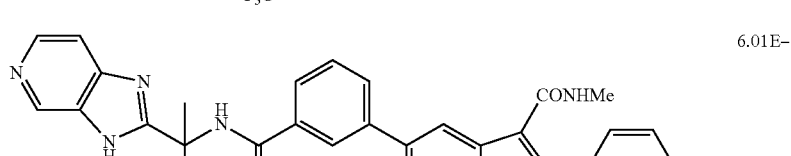 | 6.01E−03 | 0.01 |
| Example 33 | 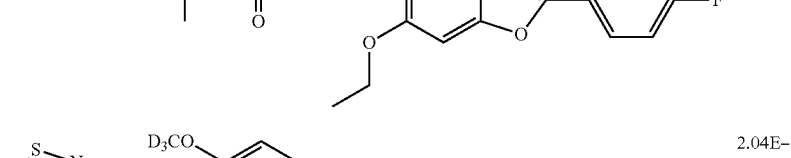 | 2.04E−03 | 2.49E−03 |
| Example 34 | 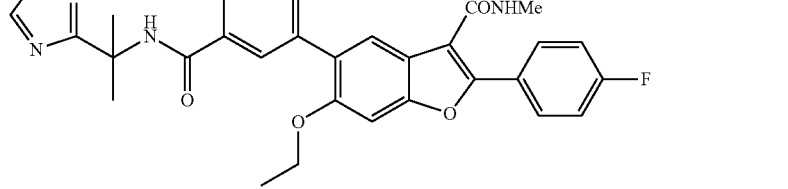 | 3.89E−03 | 8.31E−03 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of selected from the group consisting of

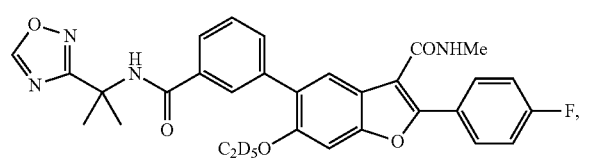

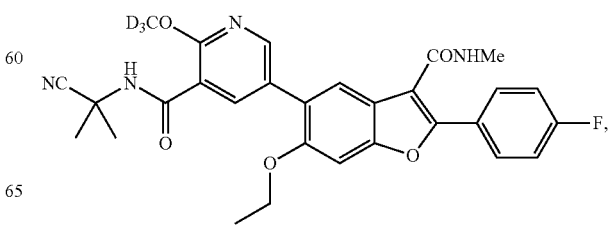

-continued
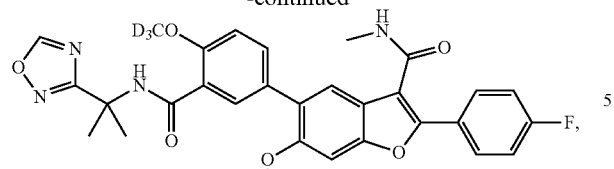
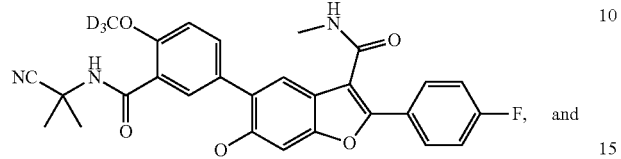
and
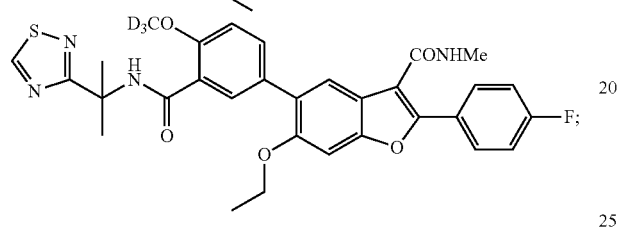
or a pharmaceutically acceptable salt thereof.
* * * * *

UNITED STATES PATENT AND TRADEMARK OFFICE
CERTIFICATE OF CORRECTION

PATENT NO. : 10,150,747 B2
APPLICATION NO. : 15/551017
DATED : December 11, 2018
INVENTOR(S) : Yeung et al.

It is certified that error appears in the above-identified patent and that said Letters Patent is hereby corrected as shown below:

In the Claims

<u>Column 119</u>
Line 58, Claim 1, after "compound" delete "of".

Signed and Sealed this
Twenty-fourth Day of November, 2020

Andrei Iancu
*Director of the United States Patent and Trademark Office*